United States Patent
Gordon et al.

(10) Patent No.: US 9,464,135 B2
(45) Date of Patent: Oct. 11, 2016

(54) EPITHELIAL MEMBRANE PROTEIN-2 (EMP2) AND PROLIFERATIVE VITRORETINOPATHY (PVR)

(75) Inventors: Lynn K. Gordon, Tarzana, CA (US); Shawn A. Morales, Pasadena, CA (US); David Telander, Carmichael, CA (US); Jonathan Braun, Tarzana, CA (US)

(73) Assignees: THE REGENTS OF THE UNIVERSITY OF CALIFORNIA, Oakland, CA (US); THE UNITED STATES OF AMERICA DEPARTMENT OF VETERAN AFFAIRS, Washington, DC (US)

( * ) Notice: Subject to any disclaimer, the term of this patent is extended or adjusted under 35 U.S.C. 154(b) by 0 days.

(21) Appl. No.: 13/510,877

(22) PCT Filed: Nov. 18, 2010

(86) PCT No.: PCT/US2010/057296
§ 371 (c)(1),
(2), (4) Date: Sep. 6, 2012

(87) PCT Pub. No.: WO2011/063161
PCT Pub. Date: May 26, 2011

(65) Prior Publication Data
US 2013/0004493 A1   Jan. 3, 2013

Related U.S. Application Data

(60) Provisional application No. 61/263,228, filed on Nov. 20, 2009.

(51) Int. Cl.
| | | |
|---|---|---|
| A61K 39/395 | (2006.01) | |
| A61K 9/48 | (2006.01) | |
| A61K 47/48 | (2006.01) | |
| A61K 9/51 | (2006.01) | |
| C07K 16/28 | (2006.01) | |
| A61K 9/00 | (2006.01) | |
| A61K 39/00 | (2006.01) | |

(52) U.S. Cl.
CPC .............. *C07K 16/28* (2013.01); *A61K 9/0048* (2013.01); *A61K 9/0051* (2013.01); *A61K 2039/505* (2013.01)

(58) Field of Classification Search
CPC .............. C07K 16/28; C07K 2317/21; C07K 2317/24; C07K 2317/34; C07K 2317/52; C07K 2317/54; C07K 2317/55; C07K 2317/56; C07K 2317/626; C07K 2317/73; C07K 2317/76; C07K 2317/96; A61K 9/0048; A61K 9/0051
See application file for complete search history.

(56) References Cited

U.S. PATENT DOCUMENTS

| | | |
|---|---|---|
| 5,264,188 A | 11/1993 | Lew |
| 5,270,163 A | 12/1993 | Gold et al. |
| 5,288,514 A | 2/1994 | Ellman |
| 5,475,096 A | 12/1995 | Gold et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,593,853 A | 1/1997 | Chen et al. |
| 5,786,362 A | 7/1998 | Krongrad |
| 6,413,245 B1 | 7/2002 | Yaacobi et al. |
| 6,506,781 B1 | 1/2003 | Cobb et al. |
| 6,750,015 B2 | 6/2004 | Horwitz et al. |
| 6,794,378 B2 | 9/2004 | Iino et al. |
| 7,229,770 B1 | 6/2007 | Price et al. |
| 7,288,531 B2 | 10/2007 | Pal et al. |
| 7,304,042 B2 | 12/2007 | Pal et al. |
| 7,345,027 B2 | 3/2008 | Tolentino et al. |
| 7,504,385 B2 | 3/2009 | Binetti et al. |
| 7,511,025 B2 | 3/2009 | Wyatt et al. |
| 7,517,865 B2 | 4/2009 | Meyers |
| 7,521,431 B2 | 4/2009 | Reich et al. |
| 7,585,848 B2 | 9/2009 | Masuda et al. |
| 7,592,325 B2 | 9/2009 | Jimenez et al. |
| 7,629,323 B2 | 12/2009 | Surmeier et al. |
| 7,638,482 B2 | 12/2009 | LaVallie et al. |
| 8,318,906 B2 * | 11/2012 | Braun et al. ............... 530/387.1 |
| 2003/0228305 A1 | 12/2003 | Frantz et al. |
| 2004/0175385 A1 | 9/2004 | Marks et al. |
| 2005/0244463 A1 | 11/2005 | Huang et al. |
| 2006/0062785 A1 | 3/2006 | Freson et al. |
| 2006/0200097 A1 * | 9/2006 | Humayun et al. ........ 604/288.01 |
| 2007/0065889 A1 | 3/2007 | Roberts et al. |
| 2008/0181889 A1 * | 7/2008 | Braun et al. ............... 424/133.1 |
| 2008/0213274 A1 * | 9/2008 | Sabbadini et al. ......... 424/141.1 |
| 2010/0272732 A1 * | 10/2010 | Braun et al. ............... 424/158.1 |
| 2012/0020983 A9 * | 1/2012 | Braun et al. ............... 424/158.1 |
| 2012/0264620 A1 * | 10/2012 | Braun et al. ....................... 506/4 |
| 2013/0004493 A1 | 1/2013 | Gordon et al. |

FOREIGN PATENT DOCUMENTS

| | | |
|---|---|---|
| EP | 0430539 A2 | 6/1991 |
| EP | 0488401 A1 | 6/1992 |

(Continued)

OTHER PUBLICATIONS

Yu et al., Investigative Ophthalmology & Visual Science 49(2): 522-527, Feb. 2008.*

(Continued)

*Primary Examiner* — Phuong Huynh
(74) *Attorney, Agent, or Firm* — Morgan, Lewis & Bockius LLP; Jeffry S. Mann

(57) ABSTRACT

Methods of preventing retinal detachment associated with proliferative vitreoretinopathy are provided by administering agents which antagonize the activity or function of EMP2 to subjects at risk of the detachment.

20 Claims, 23 Drawing Sheets

(56) References Cited

FOREIGN PATENT DOCUMENTS

| JP | 2009-531463 A | 9/2009 |
| JP | 2013-511543 A | 4/2013 |
| WO | WO 91/19735 | 12/1991 |
| WO | WO 91/19813 | 12/1991 |
| WO | WO 92/00091 | 1/1992 |
| WO | WO 93/20242 | 10/1993 |
| WO | WO 03/057160 | 7/2003 |
| WO | WO 2005/055808 | 6/2005 |
| WO | WO 2006/094014 | 9/2006 |
| WO | WO 2007/115045 | 10/2007 |
| WO | WO 2009048980 | * 4/2009 |
| WO | WO 2011/063161 | 5/2011 |

OTHER PUBLICATIONS

Witte et al., Cancer and Metastasis Reviews 17: 155-161, 1998.*
Sathish et al., Nature medicine 12: 306-324, Apr. 2013.*
Rudikoff et al., Proc. Natl. Acad. Sci. USA 1982 vol. 79: 1979.*
Colman et al., In Research in Immunology (145(1):33-35, 1994.*
Dufner et al., Trends Biotechnol 24(11): 523-529, 2006.*
Boiko et al, Vestn Oftalmol 124(5): 52-5, Abstract only Sep.-Oct. 2008.*
Abrami, L. et al., "Cross-talk between Caveolae and Glycosylphosphatidylinositol-rich Domains", Journal of Biological Chemistry, vol. 276, No. 33, pp. 30729-30736 (2001).
Agrawal et al., "Antisense therapeutics: is it as simple as complementary base recognition?" Molecular Medicine Today, vol. 6, pp. 72-81 (2000).
Amarzguioui, M. et al., "An algorithm for selection of functional siRNA sequences," Biochemical and Biophysical Research Communications, 316:1050-1058 (2004).
Anderson, E.M. et al., "Experimental validation of the importance of seed complement frequency to SiRNA specificity," RNA, 14:853-861 (2008).
Bersinger, N.A., et al., "Production of endometrial placental protein 14 and prolactin by cultured endometrial explants after collagenase and freeze/thaw treatment, and in response to progesterone", Early Pregnancy: Biology and Medicine, vol. 1, pp. 134-140 (1995).
Birmingham, A. et al., "3' UTR seed matches, but not overall identity, are associated with RNAi off-targets," Nature Methods, 3(3):199-204 (2006).
Carey, A.J. and Beagley, K.W., "Chlamydia trachomatis, a Hidden Epidemic: Effects on Femal Reproduction and Options for Treatment", Am. J. Reprod. Immunol., Abstract only (2010).
Chen, Y. et al., "RNAi for Treating Hepatitis B Viral Infection", Pharmaceutical Research, vol. 25, No. 1, pp. 72-86 (2008).
Colman, "Effects of amino acid sequence changes on antibody-antigen interactions" Research in Immunology, vol. 145, pp. 33-36 (1994).
Cui, W. et al., "OptiRNAi, an RNAi design tool," Computer Methods and Programs in Biomedicine, 75:67-73 (2004).
Delevoye, C. et al., "SNARE Protein Mimicry by an Intracellular Bacterium", PLOS Pathogens, vol. 4, Issue 3, (2008).
Dudek, P., et al., TROD: T7 RNAi Oligo Designer, Nucleic Acids Research 32:W121-W123 (2004).
Elbashir, S.M. et al., "Analysis of gene function in somatic mammalian cells using small interfering RNAs," Methods 26:199-213 (2002).
Flynn, M. A. et al., Efficient delivery of small interfering RNA for inhibition of IL-12p40 expression in vivo, Journal of Inflammation 1:4 (2004).
Ge, Q. et al., "Use of siRNAs to prevent and treat influenza virus infection", Virus Research, vol. 102, pp. 37-42 (2004).
Gura, "Systems for Identifying New Drugs Are Often Faulty" Science, vol. 278, pp. 1041-1042 (1997).
Henschel, A. et al., DEQOR: a web-based tool for the design and quality control of siRNAs, Nucleic Acids Research 32:W113-W120 (2004).

Hsieh, A. C. et al., "A library of siRNA duplexes targeting the phosphoinositide 3-kinase AT pathway: determinants of gene silencing for use in cell-based screens," Nucleic Acids Research 32(3):893-901 (2004).
Jackson, A. L., et al., "Position-specific chemical modification of siRNAs reduces 'off- target' transcript silencing," RNA 12:1197-1205 (2006).
Jain, "Barriers to Drug Delivery in Solid Tumors" Scientific American, July, pp. 58-65 (1994).
Jen et al., "Suppression of Gene Expression by Targeted Disruption of Messenger RNA: Available Options and Current Strategies" Stem Cells, vol. 18, pp. 307-319 (2000).
Kim, B. et al., Inhibition of Ocular Angiogenesis by siRNA Targeting Vascular Endothelial Growth Factor Pathway Genes, American Journal of Pathology 165(6):2177-2185 (2004).
Lane, B. Josh et al., "Chlamydial Entry Involves TARP Binding of Guanine Nucleotide Exchange Factors", PLOS Pathogens, vol. 4, Issue 3 (2008).
Leitinger and Hogg, "The involvement of lipid rafts in the regulation of integrin function", Journal of Cell Science, vol. 115, pp. 963-972 (2002).
Levenkova, N. et al., "Gene specific siRNA selector," Bioinformatics 20(3): 430-432 (2004).
Luo, K. Q. et al., "The gene-silencing efficiency of siRNA is strongly dependent on the local structure of mRNA at the targeted region," Biochemical and Biophysical Research Communications 318:303-310 (2004).
Ma, Z. et al., Cationic lipids enhance siRNA-mediated interferon response in mice, Biochemical and Biophysical Research Communications 330:755-759 (2005).
Melkonian, K., et al., "Role of Lipid Modifications in Targeting Proteins to Detergent-resistant Membrane Rafts", The Journal of Biological Chemistry, vol. 274, No. 6, pp. 3910-3917 (1999).
Milhavet, O. et al., "RNA Interference in Biology and Medicine," Pharmacol Rev 55:629-648 (2003).
Moffett, S. et al., "Lipid-dependent Targeting of G Proteins into Rafts", The Journal of Biological Chemistry, vol. 275, No. 3, pp. 2191-2198 (2000).
Mohan et al., "Characterization of the Epithelial Membrane Protein 2 in the Progression of Endometrial Adenocarcinoma" Modem Pathology, Jan. 18 (Supp.1), p. 196A (2005).
Morales, S.A. et al., "FAK Activation and the Role of Epithelial Membrane Protein 2 (EMP2) in Collagen Gel Contraction", Investigative Ophthalmology & Visual Science, vol. 50, No. 1, pp. 462-469 (2009).
Morales, S.A., "Functional Consequences of Interactions between FAK and Epithelial Membrane Protein 2 (EMP2)," IOVS, 50(10):4949-4956 (2009).
Morrissey, D. V. et al., "Activity of Stabilized Short Interfering RNA in a Mouse Model of Hepatitis B Virus Replication," Hepatology 41(6):1349-1356 (2005).
Morrissey, D. V. et al., Potent and persistent in vivo anti-HBV activity of chemically modified siRNAs, Nature Biology 23(8):1002-1007 (2005).
MSNBC News Services, "Mixed results on new cancer drug" Nov. 9, pp. 1-4 (2000).
Naito, Y. et al., "siDirect: highly effective, target-specific siRNA design software for mammalian RNA interference," Nucleic Acids Research, 32:W124-W129 (2004).
Nichols, B. et al., "Rapid Cycling of Lipid Raft Markers between the Cell Surface and Gogli Complex", The Journal of Cell Biology, vol. 153, No. 3, pp. 529-541 (2001).
Niu et al., "Restricted expression pattern of the putative tumor suppressor gene, Epithelial Membrane Protein 2 in the eye" Invest Ophthalmol Vis. Sci. E-Abstract 2419 (2002).
Opalinska et al., "Nucleic-Acid Therapeutics: Basic Principles and Recent Applications" Nature Reviews Drug Discovery, vol. 1, pp. 503-514 (2002).
Pancoskca, P. et al., "Efficient RNA interference depends on global context of the target BF sequence: quantitative analysis of silencing efficiency using Eulerian graph representation of siRNA," Nucleic Acids Research, 32(4):1469-1479 (2004).

(56) References Cited

OTHER PUBLICATIONS

Pareek et al., "Detection and Processing of Peripheral Myelin Protein PMP22 in Cultured Schwann Cells" *Journal Biol. Chemistry*, vol. 268, No. 14, pp. 10372-10379 (1993).
Paul, Ed., "Fv Structure and Diversity in Three Dimensions" *Fundamental Immunology, Third Edition*, Raven Press, New York, Chapter 8, pp. 292-295 (1993).
Reich, S. J. et al., "Small interfering RNA (siRNA) targeting VEGF effectively inhibits ocular neovascularization in a mouse model," *Molecular Vision*, 9:210-216 (2003).
Reynolds, A. et al., "Rational siRNA design for RNA interference," *Nature Biology* 22(3):326-330 (2004).
Rossi, J.J. et al., "A practical siRNA microbicide?" *Gene Therapy*, vol. 13, pp. 1493-1494 (2006).
Rudikoff et al., "Single amino acid substitution altering antigen-binding specificity" *Proc. Natl. Acad. Sci.*, vol. 79, No. 6, pp. 1979-1983 (1982).
Schiffelers, R. M. et al., "Cancer siRNA therapy by tumor selective delivery with ligand-targeted sterically stabilized nanoparticle," *Nucleic Acids Research*, 32(19):e149 (2004).
Schubert, S. et al., "Local RNA Target Structure Influences siRNA Efficacy: Systematic Analysis of Intentionally Designed Binding Regions", *J. Mol. Biol.*, vol. 348, pp. 883-893 (2005).
Shimazaki, K. et al., "Blockade of epithelial membrane protein 2 (EMP2) abrogates infection of *Chlamydia muridarum* murine genital infection model," *FEMS Immunol Med Microbiol* 1-10 (2008).
Shimazaki, K. et al., Epithelial membrane protein 2 modulates infectivity of *Chlamydia muridarum* (MoPn), *Microbes and Infection* 9:1003-1010 (2007).
Shimazaki et al., "Diabodies Targeting Epithelial Membrane Protein 2 Reduce Tumorigencity of Human Endometrial Cancer Cell Lines" *Clin. Cancer Res.*, vol. 14, No. 22, pp. 7367-7377 (2008).
Soutschek, J. et al., "Therapeutic silencing of an endogenous gene by systemic administration of modified siRNAs," *Nature*, 432:173-178 (2004).
Swanson, K. et al., "Chlamydia trachomatis Species-Specific Induction of Ezrin Tyrosine Phosphorylation Functions in Pathogen Entry", *Infection and Immunity*, vol. 75, No. 12, pp. 5669-5677 (2007).
Takasaki, S. et al., "An Effective Method for Selecting siRNA Target Sequences in Mammalian Cells," *Cell Cycle* 3(6):790-795 (2004).
Taxman, D. J. et al., "Criteria for effective design, construction, and gene knockdown by shRNA vectors," *BMC Biotechnology* 6:7 (2006).
Taylor et al., "Epithelial membrane protein-2 and epithelial membrane protein-3: two novel members of the peripheral myelin protein 22 gene family" *Gene*, vol. 175, pp. 115-120 (1996).
Ui-Tei, K. et al., "Guidelines for the selection of highly effective siRNA sequences for mammalian and chick RNA interference," *Nucleic Acids Research* 32(3):936-948 (2004).
Verma, U. N. et al., "Small Interfering RNAs Directed against β-Catenin Inhibit the in Vitro and in Vivo Growth of Colon Cancer Cells," Clinical Cancer Research, 9:1291-1300 (2003).
Wadehra, M. et al., "The Tetraspan Protein Epithelial Membrane Protein-2 Interacts with $β_1$ Integrins and Regulates Adhesion", *The Journal of Biological Chemistry*, vol. 277, pp. 41094-41100 (2002).
Wadehra, M. et al., "Characterization of the Biology and Pathobiology of Epithelial Membrane Protein-2", University of California Los Angeles Dissertation, ProQuest Information and Learning Company, Ann Arbor Michigan (2002).
Wadehra, M. et al., "Epithelial membrane protein-2 is expressed in discrete anatomical regions of the eye", *Experimental and Molecular Pathology*, vol. 74, Issue 2, pp. 106-112 (2003).
Wadehra, M. et al., "The tetraspan protein EMP2 increases surface expression of class I major histocompatibility complex proteins and susceptibility to CTL-mediated cell death", *Clinical Immunology*, vol. 107, pp. 129-136 (2003).
Wadehra, M. et al., "The Tetraspan Protein EMP2 Modulates the Surface Expression of Caveolins and Glycosylphosphatidyl Inositol-linked Proteins", *Molecular Biology of the Cell*, vol. 15, pp. 2073-2083 (2004).
Wadehra, M. et al., "Epithelial membrane protein-2 regulates surface expression of alphavbeta3 integrin in the endometrium", *Developmental Biology*, vol. 287, Issue 2, pp. 336-345 (2005).
Wadehra, M. et al., "Expression of Epithelial Membrane Protein-2 is Associated with Endometrial Adenocarcinoma of Unfavorable Outcome", *Cancer*, vol. 107(1): pp. 90-98 (2006).
Wang, L., et al., "A Web-based design center for vector-based siRNA and siRNA cassette," *Bioinformatics* 20( 11 ): 1818-1820 (2004).
Xia, H. et al., "siRNA-mediated gene silencing in vitro and in vivo," *Nature Biotechnology*, 20:1006-1010 (2002).
Yano, J. et al., "Antitumor Activity of Small Interfering RNA/ Cationic Liposome Complex in Mouse Models of Cancer," *Clinical Cancer Research* 10:7721-7726 (2004).
Yuan, B. et al., "siRNA Selection Server: an automated siRNA oligonucleotide prediction server," *Nucleic Acids Research*, 32:W130-W134 (2004).
Zhang, Y. et al., "Intravenous RNA Interference Gene Therapy Targeting the Human Epidermal Growth Factor Receptor Prolongs Survival in Intracranial Brain Cancer," *Clinical Cancer Research*, 10:3667-3677 (2004).
Morales et al., "Collagen gel contraction by ARPE-19 cells is mediated by a FAK-Src dependent pathway", *Experimental Eye Research*, 85:790-798 (2007).
Morales et al., "FAK Activation and the role of epithelial membrane protein 2 (EMP2) in collagen gel contaction," *Ophthalmol. Vix.Sci.*, 50(1): 462-469 (2009).
Shimazaki et al., "Epithelial membrane protein 2 modulates infectivity of *Chlamydia muridarum* (MoPn)," *Microbes and Infection*, 9:1003-1010 (2007).
Shimazaki et al., "Diabodies Targeting Epithelial Membrane Protein 2 Reduce Tumorigenicity of Human Endometrial Cancer Cell Lines," *Clinical Cancer Research*, 14(22): 7367-7377 (2008).
Altshul, S. et al., "Basic Local Alignment Tool", *J. Mol. Biol.*, 215:403-410 (1990).
Altschul, S. et al., "Gapped BLAST and PSI-BLAST: a new generation of protein database search programs", *Nucleic Acids Research*, 25:17 3389-3402 (1997).
Ambati, J., et al. "Age-related macular degeneration: etiology, pathogenesis, and therapeutic strategies." *Surv Ophthalmol*. 48:257-293 (2003).
Batzer, M. et al., "Enhanced evolutionary PCR using oligonucleotides with inosine at the 3'-terminus", *Nucleic Acids Res.*, 19:18 5081 (1991).
Campbell et al., "Phosphate Ester Synthesis Using a Modified Mitsunobu Condensation", *J. Org. Chem.*, 59: 658 (1994).
Chen, C. et al., "'Analogous' organic synthesis of small compound libraries: Validation of combinatorial chemistry in small-molecule synthesis", *J. Am. Chem. Soc.*, 116: 2661-2662 (1994).
Cho, C. et al., "An unnatural biopolymer", *Science* 261: 1303 (1993).
Connolly, D. et al., "Tumor vascular permeability factor stimulates endothelial cell growth and angiogenesis", J. Clin. Invest. 84: 1470-1478 (1989).
Connolly, D. et al., "Human vascular permeability factor. Isolation from U937 cells", J. Biol. Chem., 264: 20017-20024 (1989).
De Witt, S. Hobbs et al., "'Diversomers': An approach to nonpeptide, nonoligomeric chemical diversity", *Proc. Natl., Acad. Sci*. USA, 90: 6909-6913 (1993).
Dvorak, H.F., "Tumors: wounds that do not heal. Similarities between tumor stroma generation and wound healing", *N. Engl. Journ. Med.*, 315: 1650-1659 (1986).
Friedlander, M. et al., "Definition of Two Angiogenic Pathways by Distict $α_v$ Integrins", Science, vol. 270, pp. 1500-1502 (1995).
Gerhardinger et al., "Expression of vascular endothelial growth factor in the human retina and in nonproliferative diabetic retinopathy", *Am. J. Pathol*. 152: 1453-1462 (1998).
Hagihara, M. et al., "Vinylogous polypeptides: an alternative peptide backbone", *J. Am. Chem. Soc.*, 114: 6568 (1992).

(56) References Cited

OTHER PUBLICATIONS

Henikoff S. and Henikoff, J., "Amino acid substitution matrices from protein blocks", *Proc. Natl., Acad. Sci.*, USA, 89: 10915-10919 (1992).
Hirschmann, R. et al., "Nonpeptidal peptidomimetics with beta-D-glucose scaffolding. A partial somatostatin against bearing a close structural relationship to a potent, selective substance P antagonist." *J. Am. Chem. Soc.*, 114: 9217-9218 (1992).
Hughes, L. and Maurice, D., "A Fresh Look at Iontophoresis", Arch Ophthalmol, vol. 102, pp. 1825-1829 (1984).
Husain, D. et al. "Photodynamic therapy and digital angiography of experimental iris neovascularization using liposomal benzoporphyrin derivative", *Opthamology* 104: 1242-12450 (1997).
Kim, I. et al., "Constitutive expression of VEGF, VEGFR-1, and VEGFR-2 in normal eyes", *Invest. Opthalmol. Vis. Sci.* 40: 2115-2121 (1999).
Kliffen, M. et al., "Increased expression of angiogenic growth factors in age-related maculopathy", Br. J Opthalmol. 81: 154-162 (1997).
Kvanta, A. et al., "Subfoveal fibrovascular membranes in age-related macular degeneration express vascular endothelial growth factor", *Invest. Opthalmol. Vis. Sci.* 37: 1929-1934 (1996).
Lee, V. H. L. et al., "Review: Topical Ocular Drug Delivery: Recent Developments and Future Challenges", *Journal of Ocular Pharmacology*, vol. 2, No. 1, pp. 67-108 (1986).
Leung, D.W. et al., "Vascular endothelial growth factor is a secreted angiogenic mitogen", *Science* 246:1306-1309 (1989).
Liang et al. "Parallel Synthesis and Screening of a Solid Phase Carbohydrate Library," *Science* 274:1520-1522 (1996).
Lopez, P. et al., "Transdifferentiated retinal pigment epithelial cells are immunoreactive for vascular endothelial growth factor in surgically excised age-related macular degeneration-related choroidal neovascular membranes", *Invest. Opthalmol. Vis. Sci.* 37: 855-868 (1996).
McCafferty, J. et al., "Phage antibodies: filamentous phage displaying antibody variable domains", *Nature*, 348: 552-554 (1990).
McConnell, V. et al., "Assessment of a putative locus for exudative age-related macular degeration on chromosome 16p", *J. Med. Genet.* 41: Supplement 1 (2004).
Miller, J.W. et al., "Vascular endothelial growth factor in ocular neovascularization and proliferative diabetic retinopathy", *Diabetes Metab. Rev.* 13: 37-50 (1997).
Morales, S. et al., "FAK Activation and the Role of Epithelial Membrane Protein 2 (EMP2) in Collagen Gel Contraction", IOVS, 50: 462-469 (2009).
Morales, S. et al., "Epithelial Membrane Protein 2 Controls VEGF Expression in ARPE-19 Cells", *IVOS*, 54: 2367-2372 (2013).
Ohtsuka, E. et al., "An Alternative Approach to Deoxyoligonucleotieds as Hybridization Probes by Insertion of Deoxyinosine at Ambiguous Codon Positions", *The Journal of Biol. Chem.*, 260:5 2605-2608 (1985).
Olsen, T.W. et al., "Human scleral permeability. Effects of age, cryotherapy, transscleral diode laser, and surgical thinning", Invest. Ophthalmol. Vis. Sci. 36: 1893-1903 (1995).
Plouet, J. et al., "Isolation and characterization of a newly identified endothelial cell mitogen produced by AtT-20 cells", EMBO J., 8:3801-3806 (1989).
Rossolini, G. et al., "Use of deoxyinosine-containing primers vs degenerate primers for polymerase chain reaction based on ambiguous sequence information", *Mol. Cell. Probes*, 8:91-98 (1994).
Schwesinger, C. et al., "Intrachoroidal neovascularization in transgenic mice overexpressing vascular endothelial growth factor in the retinal pigment epithelium", Am. J. Pathol. 158: 1161-1172 (2001).
Sorbera, L.A. et al. "Treatment of Age-Related Macular Degeneration Humanized Monoclonal Anti-VEGF Antibodiy Angiogenesis Inhibitor", *Drugs of the Future*, 28: 541-545 (2003).
Sundaresan, G. et al., "$^{124}$I-Labeled Engineered Anti-CEA Minibodies and Diabodies Allow High-Contrast, Antigen-Specific Small-Animal PET Imaging of Xenografts in Athymic Mice", *Journal of Nuclear Medicine*, 44:12, 1962-1969 (2003).
Vaughan et al. "Human Antibodies with Sub-nanomolar Affinities Isolated from a Large Non-immunized Phage Display Library," *Nature Biotechnology* 14(3):309-314 (1996).
Wang, C. et al., "Epithelial membrane protein 2,a 4-transmembrane protein that suppresses B-ceillymphoma tumorigenicity," *Blood*, 97(12):3890-3895 (2001).
Wu, A. and Senter, P., "Arming antibodies: prospects and challenges for immunoconjugates", *Nature Biotech*, 23:1, 1137-1146 (2005).
Yi, X. et al., "Vascular endothelial growth factor expression in choroidal neovascularization in rats", *Graefes Arch Clin Exp Opthalmol* 235: 313-319 (1997).
Chan, A. et al., "Epithelial Membrane Protein 2 (EMP2) Modulates Hypoxia-Inducible Factor 1α(Hif-1α and VEGF Expression by ARPE-19 Cells", *Invest. Opthalmol Vis. Sci.*, 53:Abstract 4776 (2012).
Harrison, C. "Eye Diseases, Convenient leakage reduction", *Nature Reviews*, vol. 7 (2008).
Mitra, S.K. and Schlaepfer, D.D., "Integrin-regulated FAK-Src signaling in normal and cancer cells", *Current Opinion of Cell Biology*, 18:516-523 (2008).
Rosenthal, R. et al., "$Ca^{2+}$ channels in retinal pigment epithelial cells regulate vascular endothelial growth factor secretion raates in health and disease", *Molecular Vision*, 13:443-456 (2007).
Scheppke, L. et al., "Retinal vascular permeability suppression by topical application of a novel VEGFR2/Src kinase inhibitor in mice and rabbits", *The Journal of Clinical Investigation*, vol. 118, No. 6, pp. 2337-2346 (2008).
Morales, S.A. et al., "Collagen gel contraction by ARPE-19 cells is mediated by a FAK-Src dependent pathway", Experimental Eye Research, vol. 85, pp. 790-798 (2007).
Morales, S.A. et al., "Novel Therapies to Reduce Proliferative Vitreoretinopathy, Evidence From an in vitro Model", *IOVS*, vol. 50, Abstract 2713 (2009).
Shimazaki, K. et al., "Expression of Epithelial Membrane Protein 2 (EMP-2) Controls Chlamydia Infectivity", *IOVS*, vol. 46, Abstract 5074 (2005).
Ellis, Lee M. et al., "Down-regulation of Vascular Endothelial Growth Factor in a Human Colon Carcinoma Cell Line Transfected with an Antisense Expression Vector Specific for c-src.", *The Journal of Biological Chemistry*, vol. 273, No. 2, pp. 1052-1057 (1998).

\* cited by examiner

FIG. 8
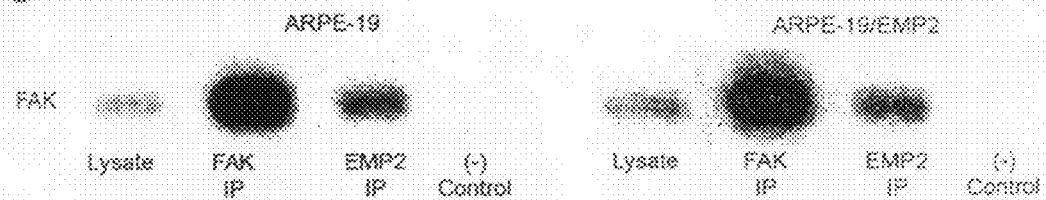
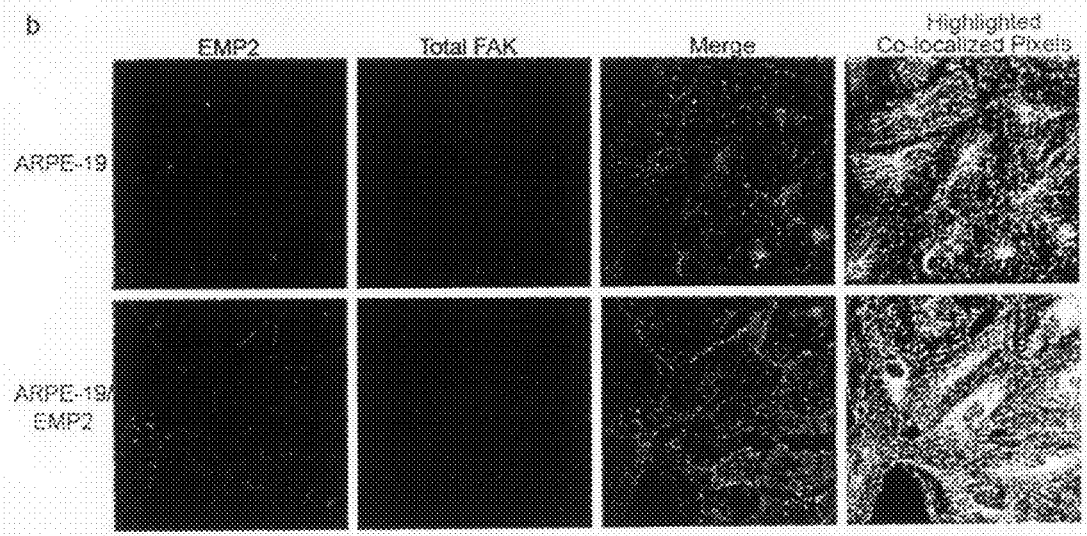
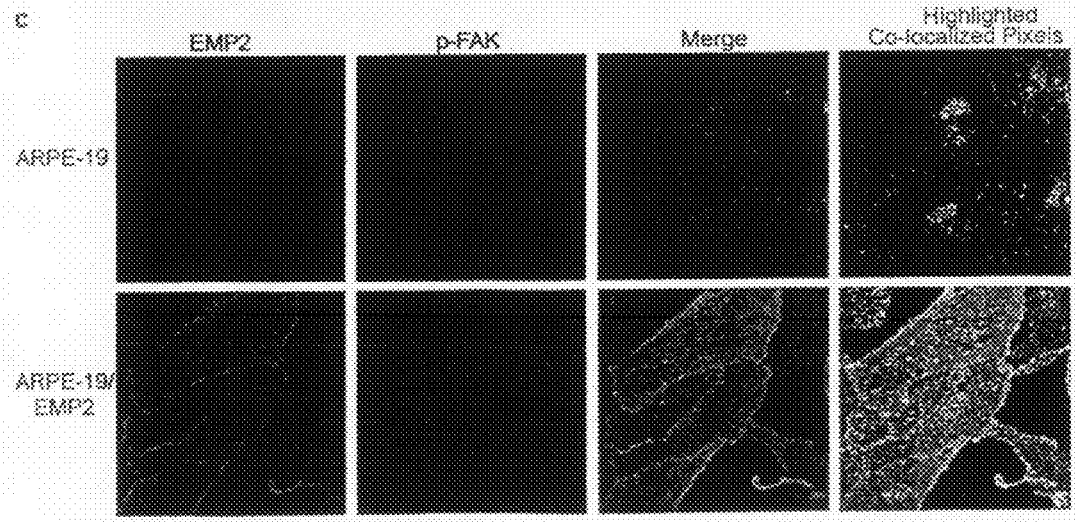

FIG. 11
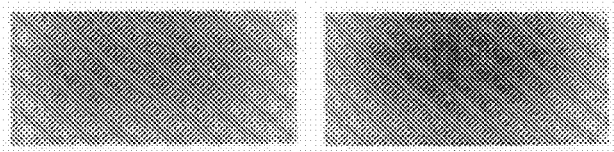
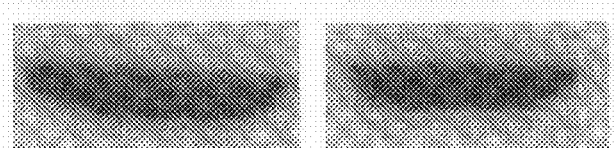
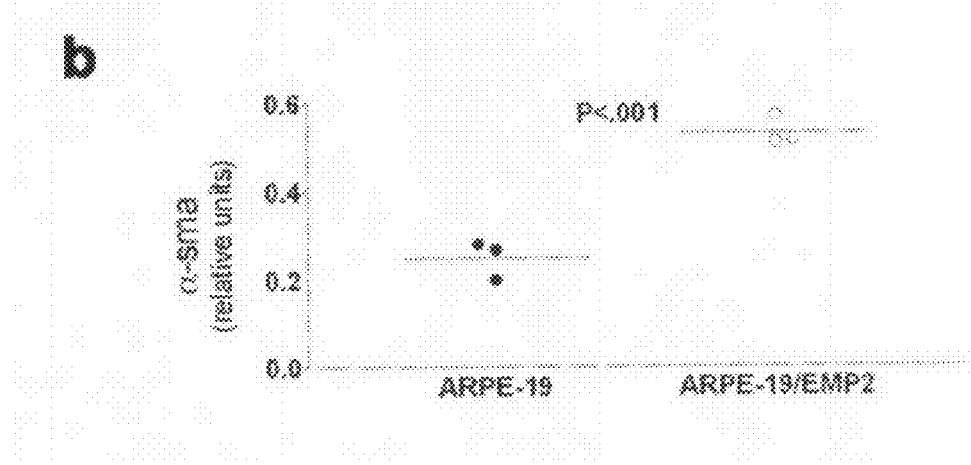

FIG. 20A

KS49 heavy chain:
MAQVQLVQSGGGVVQPGRSLRLSCAASGFTFSSYAMHWVRQAPGKGLEWVAVIS
                                    CDR-H1

YDGSNKYYADSVKGRFTISRDNSKNTLYLQMNSLRAEDTAVYYCARDRRGRKSA
    CDR-H2                                       CDR-H3

GIDYWGQGTLVTVSS
CDR-H3

KS49 light chain:
DIQMTQSPSSLSASVGDRVTITCQASQDISNYLNWYQQKPGKAPKLLIYAASSL
                          CDR-L1                  CDR-L2

QSGVPSRFSGSGSGTDFTLTISSLQPEDFATYYCLQDYNGWTFGQGTKVDIKRA
                                     CDR-L3

AAEQKLISEEDLNGAA

FIG. 20B

KS83 heavy chain:
MAQVQLVESGGGLVQPGGSLRLSCAASGFTFS SYAMH WVRQAPGKGLEWVAVIS
                                 ─────                    ─────
                                 CDR-H1

YDGSNKYYADSVKGRFTISRDNSKNTLYLQMNSLRAEDTAVYYCAR TVGATGAF
─────────────                                   ────────
   CDR-H2                                        CDR-H3

DIWGQGTMVTVSSS

KS83 light chain:
DIVMTQSPSTVSASVGDRVIIPC RASQSIGKWLA WYQQKPGKAPKLLIY KASSL
                        ───────────                 ─────
                           CDR-L1                   CDR-L2

EGWVPSRFSGSGSGTEFSLTISSLQPDDSATYVC QQSHNFPPT FGGGTKLEIKR
                                   ─────────
                                     CDR-L3

AAAEQKLISEEDLNGAA

FIG. 20C

KS41 Heavy Chain:
MAQVQLVQSGGGLVQPGRSLRLSCAASGFSFSEYPMHWVRQAPGRGLESVAVIS
                                   ‾‾‾‾‾‾‾‾‾‾‾‾‾‾‾‾‾‾
                                         CDR-H1

YDGEYQKYADSVKGRFTISRDDSKSTVYLQMNSLRPEDTAVYYCARTINNGMDV
‾‾‾‾‾‾‾‾‾‾‾‾‾‾                                ‾‾‾‾‾‾‾‾‾
    CDR-H2                                      CDR-H3

WGQGTTVTVSS

KS41 Light Chain:
DIVMTQSPSSLSASVGDRVTITCRASQGIRNDLGWYQQKPGKAPELLIYGASSL
                        ‾‾‾‾‾‾‾‾‾‾‾‾‾             ‾‾‾‾‾
                            CDR-L1                CDR-L2

QSGVPSRFSGSGSGTDFTLTISSLQPEDSATYYCLQDYNGWTFGQGTKLEIKRA
‾                                ‾‾‾‾‾‾‾‾‾
                                   CDR-L3

AAEQKLISEEDLNGAA

FIG. 20D

KS89 Heavy Chain:
MAQVQLVQSGGGLVQPGRSLRLSCAASGFSFS EYPMH WVRQAPGRGLESVAVIS
                                 —CDR-H1—

YDGEYQKYADSVKG RFTISRDDSKSTVVYLQMNSLRPEDTAVYYC ARTINNGMDV
               —————CDR-H2—————                 ——CDR-H3——

WGQGTTVTVSS

KS89 Light Chain:
DIVMTQSPSSLSASVGDRVTITC RASQGIRNDLG WYQQKPGKAPELLIY GASSL
                        ———CDR-L1———                 CDR-L2

QSGVPSRFSGSGSGTDFTLTISSLQPEDSATYYC LQDYNGWT FGQGTKLEIKRA
                                   ——CDR-L3——

AAEQKLISEEDLNGAA

EPITHELIAL MEMBRANE PROTEIN-2 (EMP2) AND PROLIFERATIVE VITRORETINOPATHY (PVR)

CROSS-REFERENCES TO RELATED APPLICATIONS

This application claims the benefit of U.S. Provisional Application Ser. No. 61/263,228, filed Nov. 20, 2009, the contents of which are incorporated herein by reference in its entirety. This application also contains subject matter that relates to U.S. patent application Ser. No. 11/868,788, filed Oct. 8, 2007, and U.S. patent application Ser. No. 11/884,806, filed Oct. 9, 2008, the contents of each of which are incorporated herein by reference in its entirety.

STATEMENT AS TO RIGHTS TO INVENTIONS MADE UNDER FEDERALLY SPONSORED RESEARCH AND DEVELOPMENT

This work was supported by the U.S. Department of Veterans Affairs, and the Federal Government has certain rights in the invention.

REFERENCE TO A "SEQUENCE LISTING," A TABLE, OR A COMPUTER PROGRAM LISTING APPENDIX SUBMITTED ON A COMPACT DISK

The sequence listing contained in the file named "008074-5031-US", created on Aug. 8, 2013 and having a size of 22.3 kilobytes, has been submitted electronically herewith via EFS-Web, and the contents of the txt file are hereby incorporated by reference in their entirety.

BACKGROUND OF THE INVENTION

The most common reason for failure in the therapy of retinal detachment or open globe injuries is the proliferation and contraction of cellular membranes that form in the vitreous cavity, termed proliferative vitreoretinopathy (PVR) (Pastor, J. C. *Surv Ophthalmol* 43:3-18 (1998)). It is estimated that PVR occurs as a complication of up to 5-20% of cases of rhegmatogenous retinal detachment (Pastor, J. C. *Surv Ophthalmol* 43:3-18 (1998); Pastor, J. C. et al., *Prog Retin Eye Res* 21:127-44 (2002)). In ocular trauma, the risk of PVR is very high. A review of veterans who had suffered ocular trauma with intraocular foreign bodies in Iraq during the years 2003-2005 revealed PVR as the cause for poor vision in 21% of the patients. (Colyer M. H. et al., Ophthalmology. 2007 August; 114(8):1439-47).

Clinical studies have identified multiple risk factors for the development of PVR, including vitreous hemorrhage, intraocular gas, large or long-standing retinal detachments, and surgical failures, especially if they are associated with extensive use of cryotherapy or photocoagulation (Pastor, J. C. *Surv Ophthalmol* 43:3-18 (1998); Pastor, J. C. et al., *Prog Retin Eye Res* 21:127-44 (2002)). It is possible that the extent of ocular/retinal damage leads to increased cytokine production or other signaling to cause increased PVR. Proinflammatory cytokines (for example IL-8 and MCP-1) and IL-1, IL-6, TNF-α, and IFN-γ have been found to be increased in PVR, however, cytokine levels do not directly correlate with PVR severity (Asaria, R. H. Compr Ophthalmol Update 7:179-85 (2006)).

The retinal pigment epithelium (RPE) is believed to be one of the critical cell types implicated in PVR. Pathogenesis underlying PVR is complex; however it is likely that, following trauma or retinal detachment, RPE cells are released into the vitreous or are stimulate to migrate from their subretinal location. These cells then migrate, proliferate, de-differentiate, and undergo an epithelial to mesenchymal transformation (EMT), to help create the preretinal membranes of PVR (Asaria, R. H. Compr Ophthalmol Update 7:179-85 (2006)). It is likely that the RPE cells produce membrane contraction that generates a tractional force that often lead to recurrent retinal detachments and additional vision loss (Pastor, J. C. et al., *Prog Retin Eye Res* 21:127-44 (2002); Kroll, P. et al., *Ophthalmologica* 221:78-94 (2007)).

While EMP2 has been found to be highly expressed in RPE cells, its function is only beginning to be understood (Wadehra, M. et al., *Exp Mol Pathol* 74:106-12 (2003)). As a member of the tetraspanin family (CD9, CD53, CD81, CD82) modulation of integrin and other cell surface receptors is common. EMP2 has been previously shown to be important in regulating cellular contractile capacity through facilitating the activation of the FAK.Src signaling complex (Morales, S. A. et al., *Exp Eye Res* 85:790-8 (2007); Morales, S. A. et al., *Invest Ophthalmol Vis Sci* 50:462-9 (2009)). In addition, activation of the FAK/Src complex has been proven to be through the physical association between EMP2 and the FAK/Src complex (Morales, S. A. et al., *Invest Ophthalmol Vis Sci* 50:462-9 (2009)). These in vitro studies found that EMP2 and the FAK/Src signaling complex were critical components in RPE mediated gel contraction.

Although we report here that the RPE cells are concordant in both in vivo and in vitro studies, there are many potential differences between the previously reported observations and the present investigation. First, the in vitro studies use collagen as scaffold for the RPE cells where as the RPE cells in the in vivo vitreous is exposed to hyaluronic acid and many collagen types including II, V/XI, and IX. In addition, there are many cell types that contribute to the PVR membrane in vivo including inflammatory cells, Mueller cells, fibroblast etc. (Pastor, J. C. *Surv Ophthalmol* 43:3-18 (1998); Pastor, J. C. et al., *Prog Retin Eye Res* 21:127-44 (2002); Asaria, R. H. Compr Ophthalmol Update 7:179-85 (2006); Kim, I. K. et al. *Ophthalmol Clin. North Am* 15:81-6 (2002)). In vivo, during PVR membrane formation, the cells are known to be exposed to many cytokines, and pre-retinal membranes have been found to contain cytokines including: vascular endothelial growth factor (VEGF), (PDGF), IL-6, IL-8, TNF-alpha, TGF-beta etc. (Harada, C. et al., *Prog Retin Eye Res* 25:149-64 (2006)). These cells and the milieu of cytokines made by these cells will certainly influence the cell and membrane behavior.

Today, despite surgical advances, patients too frequently lose vision secondary to PVR and tractional pre-retinal membranes. This invention meets a need for the treatment and/or prevention of retinal detachments associated with PVR.

BRIEF SUMMARY OF THE INVENTION

In one aspect, the present invention provides methods of treating proliferative vitreoretinopathy or retinal detachment in a subject. In some embodiments, the method comprises administering to the subject an anti-EMP2 agent that reduces EMP2 activity in the eye.

In some embodiments, the subject is a human. In some embodiments, the anti-EMP2 agent is locally administered. In some embodiments, the anti-EMP2 agent is systemically administered. In some embodiments, the anti-EMP2 agent is administered directly to the eye. In some embodiments, the anti-EMP2 agent is administered intraocularly. In some embodiments, the anti-EMP2 agent is administered into the vitreous humor of the eye.

In some embodiments, administration of the anti-EMP2 agent reduces the risk of a retinal detachment. In some embodiments, administration of the anti-EMP2 agent reduce the extent of a retinal detachment.

In some embodiments, the anti-EMP2 agent is formulated for injection into the eye. In some embodiments, the anti-EMP2 agent is formulated for local administration external to the eye.

In some embodiments, the vitreoretinopathy is rhegmatogenous vitreoretinopathy. In some embodiments, prior to administration of the anti-EMP2 agent, the eye suffered a traumatic injury or a surgery contributing to the risk of retinal detachment.

In another aspect, the present invention provides methods of decreasing contractile capacity of a retinal pigment epithelial cell in a biological sample. In some embodiments, the method comprises contacting the biological sample with an anti-EMP2 agent that reduces EMP2 activity in the retinal pigment epithelial cell.

In some embodiments, the biological sample is a tissue sample. In some embodiments, the tissue sample is eye tissue.

In some embodiments, the anti-EMP2 agent is an antibody or fragment thereof that specifically binds to an EMP2 polypeptide having at least 70% amino acid sequence identity to SEQ ID NO:1, SEQ ID NO:2, or SEQ ID NO:30. In some embodiments, the antibody comprises a heavy chain comprising an amino acid sequence having at least 70% amino acid sequence identity to SEQ ID NO:4, SEQ ID NO:6, SEQ ID NO:8, or SEQ ID NO:10. In some embodiments, the antibody comprises a light chain comprising an amino acid sequence having at least 70% amino acid sequence identity to SEQ ID NO:5, SEQ ID NO:7, SEQ ID NO:9, or SEQ ID NO:11. In some embodiments, the antibody comprises (1) a heavy chain selected from the group consisting of SEQ ID NO:4, SEQ ID NO:6, SEQ ID NO:8, and SEQ ID NO:10; and (2) a light chain selected from the group consisting of SEQ ID NO:5, SEQ ID NO:7, SEQ ID NO:9, and SEQ ID NO:11. In some embodiments, the antibody has at least 70% amino acid sequence identity to SEQ ID NO:27, SEQ ID NO:28 or SEQ ID NO:29. In some embodiments, the antibody has the amino acid sequence of SEQ ID NO:27, SEQ ID NO:28, or SEQ ID NO:29.

In some embodiments, the antibody is a monoclonal antibody. In some embodiments, the antibody is a humanized monoclonal antibody. In some embodiments, the antibody is a polyclonal antibody. In some embodiments, the antibody fragment is provided as a diabody or a minibody. In some embodiments, the antibody fragment is a Fv, F(ab') or F(ab)$_2$ fragment. In some embodiments, the antibody is a chimeric antibody having a murine antigen-binding site and a humanized region that regulates effector function. In some embodiments, the antibody or fragment thereof is coupled to a cytotoxic agent.

In some embodiments, the anti-EMP2 agent is an siRNA that is capable of reducing the expression of a nucleic acid encoding an EMP2 protein having at least 70% amino acid sequence identity to the polypeptide of SEQ ID NO:1. In some embodiments, the siRNA comprises a nucleic acid sequence having at least 70% nucleotide sequence identity to at least 15 contiguous nucleotides of the nucleic acid sequence of SEQ ID NO:3 or its complement. In some embodiments, the siRNA comprises at least 15 contiguous nucleotides of the nucleic acid sequence of SEQ ID NO:3 or its complement.

In some embodiments, the anti-EMP2 agent is a hammerhead ribozyme which is capable of cleaving an EMP2 polynucleotide sequence having at least 70% nucleotide sequence identity to the nucleic acid sequence of SEQ ID NO:3.

In some embodiments, the anti-EMP2 agent is a progesterone receptor antagonist. In some embodiments, the anti-EMP2 agent is Mifepristone.

BRIEF DESCRIPTION OF THE DRAWINGS

As shown in FIG. 5, pre-retinal PVR membranes were most prominent in wild-type and pre-immune rabbit groups than in those pre-treated with anti-EMP2 antibody. This figure shows EMP2 expression (violet) in the pre-retinal PVR membranes from in all three groups of rabbits: Wt (A), pre-immune (B) and anti-EMP2 antibody (C).

FIG. 8. Association of FAK and EMP2. (A) Lysates from ARPE-19 and ARPE-19/EMP2 ($10^7$ cells) were immunoprecipitated using antibody to FAK, EMP2, or irrelevant rabbit antibody (—control). SDS-PAGE was performed with aliquots of the immunoprecipitates or of the original lysate ($10^6$ and $10^5$ cell equivalents, respectively), and Western blots were analyzed for FAK. Cognate immunoprecipitation of FAK and EMP2 (data not shown) were comparably efficient (50-60%). EMP2 co-immunoprecipitated 25% and 30% of total FAK in ARPE-19 and ARPE-19/EMP2, respectively. Data are representative of three or more experiments. (B) ARPE-19 and ARPE-19/EMP2 cells were stained with antibodies to EMP2 followed by secondary FITC-conjugated donkey anti-rabbit IgG (green) and FAK followed by secondary Texas Red-conjugated donkey anti-goat (red). The merge of these two channels is shown (center-right), as well as a merge in which highlighted colocalized pixels are displayed (right). At least 6 fields were randomly chosen for analysis for each sample and percent association is an average value generated from the multiple fields. Multiple slices per field were captured, presented is a single slice of the bottom surface of the cell, which contacts the slide and contains focal adhesions. In ARPE-19 and ARPE-19/EMP2, 68% and 96% of total FAK colocalized with EMP2, respectively. (C) To assess the association between EMP2 and phosphorylated FAK, ARPE-19 and ARPE-19/EMP2 cells were stained with antibodies against EMP2 and against p576/577-FAK. Bound antibody against EMP2 is identified using a FITC-conjugated secondary antibody whereas bound antibody against p-FAK (Y576/577) staining is shown with a Texas Red-conjugated secondary antibody. A merge of these two channels is shown (white) and colocalized pixels are observed and quantified. At least 6 fields were randomly chosen for analysis for each sample and percent association is an average value generated from the multiple fields. Multiple slices per field were captured, presented is a single slice of the bottom surface of the cell, which contacts the slide and contains focal adhesions. In the ARP-19 cells 31% of phosphorylated FAK is colocalized with EMP2. In the ARPE-19/EMP2 cells 97% of phosphorylated FAK is colocalized with EMP2. Increasing EMP2 levels results in increased phosphorylated FAK-EMP2 association.

FIG. 11. Increased EMP2 expression resulted in increased α-smooth muscle actin expression. (A) Steady state protein levels of α-smooth muscle actin (α-sma) in the ARPE-19 and ARPE-19/EMP2 cells were measured by Western blot analysis; β-actin was used as a loading control. (B) The amount of α-sma was calculated for each sample relative to β-actin. At least three independent experiments were performed and the results are presented numerically. Differences in expression levels were evaluated using a student's t-test (unpaired, one-tail).

FIG. 20. Sequences of antibodies KS49, KS83, KS41, and KS89. A. Amino acid sequence of KS49 heavy chain (SEQ ID NO:4) and KS49 light chain (SEQ ID NO:5). CDR-H1 (SEQ ID NO:12), CDR-H2 (SEQ ID NO:13), CDR-H3 (SEQ ID NO:14), CDR-L1 (SEQ ID NO:15), CDR-L2 (SEQ ID NO:16), and CDR-L3 (SEQ ID NO:17) are underlined. B. Amino acid sequence of KS83 heavy chain (SEQ ID NO:6) and KS49 light chain (SEQ ID NO:7). CDR-H1 (SEQ ID NO:12), CDR-H2 (SEQ ID NO:13), CDR-H3 (SEQ ID NO:18), CDR-L1 (SEQ ID NO:19), CDR-L2 (SEQ ID NO:20), and CDR-L3 (SEQ ID NO:21) are underlined. C. Amino acid sequence of KS41 heavy chain (SEQ ID NO:8) and KS41 light chain (SEQ ID NO:9). CDR-H1 (SEQ ID NO:22), CDR-H2 (SEQ ID NO:23), CDR-H3 (SEQ ID NO:24), CDR-L1 (SEQ ID NO:25), CDR-L2 (SEQ ID NO:26), and CDR-L3 (SEQ ID NO:17) are underlined. D. Amino acid sequence of KS89 heavy chain (SEQ ID NO:10) and KS89 light chain (SEQ ID NO:11). CDR-H1 (SEQ ID NO:22), CDR-H2 (SEQ ID NO:23), CDR-H3 (SEQ ID NO:24), CDR-L1 (SEQ ID NO:25), CDR-L2 (SEQ ID NO:26), and CDR-L3 (SEQ ID NO:17) are underlined.

DETAILED DESCRIPTION OF THE INVENTION

I. Definitions

Figure 1:
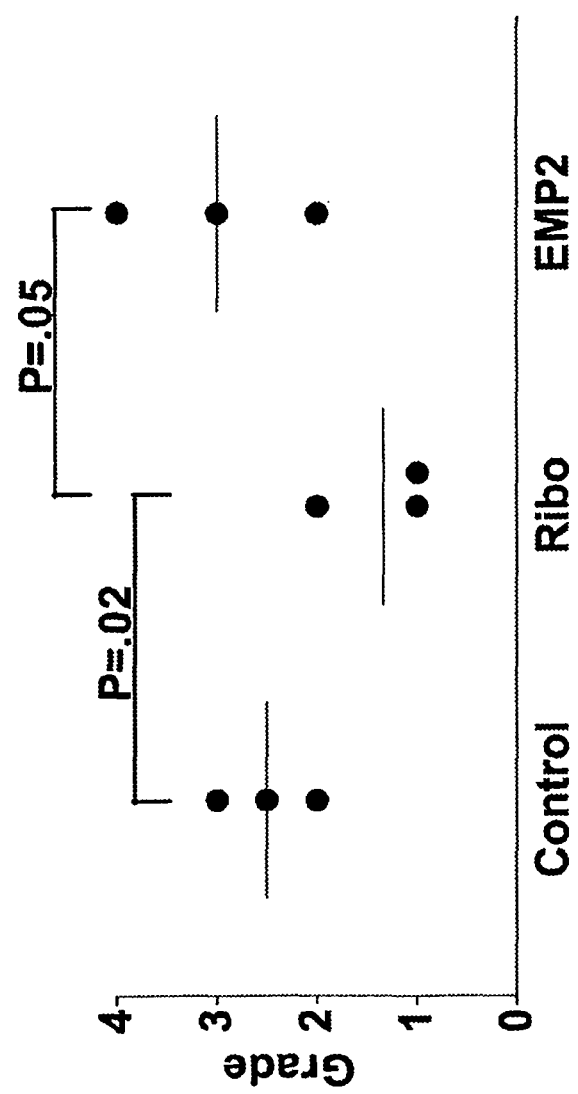
FIG. 1. Rabbit PVR model graded according to the Fastenburg system as shown in Table 1. 3 rabbits were in each group: Control—rabbits that received ARPE19 cells transfected with the vector alone; Ribo—rabbits that received ribozyme-transfected cells with lower expression of EMP2; and EMP2—rabbits that received cells transfected to overexpress EMP2. The rabbits that received cells overexpressing EMP2 had increased rates of PVR formation whereas the animals that received the cells with lower levels of EMP2 expression by ribozyme knockdown (Ribo) had decreased degrees of PVR formation. The results presented were obtained 5 weeks after cell injection. Student T-test p values shown above compared groups.

It is noted here that as used in this specification and the appended claims, the singular forms "a," "an," and "the" include plural reference unless the context clearly dictates otherwise.

"Epithelial membrane protein 2" or "EMP2" refers to refers to nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity, over a region of at least about 25, 50, 100, 200, 500, 1000, or more amino acids, to a polypeptide encoded by a respectively referenced nucleic acid or an amino acid sequence described herein, for example, as depicted in GenBank Accession Nos. NM_001424 (EMP2 mRNA) and P54851 (EMP2 protein); specifically bind to antibodies, e.g., polyclonal antibodies, raised against an immunogen comprising a referenced amino acid sequence as depicted in GenBank Accession No. P54851 (EMP2 protein), immunogenic fragments respectively thereof, and conservatively modified variants respectively thereof; (3) specifically hybridize under stringent hybridization conditions to a nucleic acid encoding a referenced amino acid sequence as depicted in GenBank Accession No. P54851 (EMP2 protein) and conservatively modified variants respectively thereof; (4) have a nucleic acid sequence that has greater than about 95%, preferably greater than about 96%, 97%, 98%, 99%, or higher nucleotide sequence identity, preferably over a region of at least about 15, 20, 25, 50, 100, 150, 200, 250, 500, 1000, or more nucleotides, to a reference nucleic acid sequence as shown in GenBank Accession No. NM_001424 (EMP2 mRNA). A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules.

An "anti-EMP2 agent" or "EMP2 inhibitor" is an agent which interferes with the function, activity, or tissue levels of a cellular EMP2 (e.g., an EMP2 having the amino acid sequence of SEQ ID NO:1) mediating the contracture involved in retinal detachment. A EMP2 inhibitor can be EMP2 polypeptide; an anti-EMP2 antibody (e.g., a recombinant antibody, polyclonal antibody, monoclonal antibody, chimeric antibody, human monoclonal antibody, humanized or primatized monoclonal antibody, or antibody fragment); an EMP2 siRNA molecule; an EMP2-ribozyme; a compound which competes with binding to EMP2 or the binding of EMP2, or an agent or compound which inhibits the expression, transcription, or translation of EMP2 nucleic acids in a host cell. In some embodiments, the EMP2 inhibitors are provided in a composition also comprising a sterile carrier and/or physiologically acceptable carrier.

"Modulators" are agents which can increase or decrease a referenced activity. Modulators include both inhibitors and "activators," which have effects opposite to inhibitors (e.g., increase, stimulate, augment, enhance, accelerate) with respect to a referenced activity or entity.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "complementarity-determining region" or "CDR" refers to the hypervariable regions of $V_L$ and $V_H$. The CDRs are the target protein-binding site of the antibody chains that harbors specificity for such target protein. There are three CDRs (CDR1-3, numbered sequentially from the N-terminus) in each human $V_L$ or $V_H$, constituting about 15-20% of the variable domains. The CDRs are structurally complementary to the epitope of the target protein and are thus directly responsible for the binding specificity. The remaining stretches of the $V_L$ or $V_H$, the so-called framework regions, exhibit less variation in amino acid sequence (Kuby, Immunology, 4th ed., Chapter 4. W.H Freeman & Co., New York, 2000).

The positions of the CDRs and framework regions are determined using various well known definitions in the art, e.g., Kabat, Chothia, international ImMunoGeneTics database (IMGT) (on the worldwide web at imgt.cines.fr/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M.J.E. (ed.), Protein Structure Prediction, Oxford University Press, Oxford, 141-172 (1996).

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$. a dimer of Fab which itself is a light chain joined to V$_H$-C$_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

Accordingly, the term antibody also embraces minibodies, diabodies, triabodies, and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., *J Nucl Med* 44:1962-9 (2003). In addition, these antibodies are advantageous because they can be engineered if necessary as different types of antibody fragments ranging from a small single chain Fv to an intact IgG with varying isoforms (Wu & Senter, *Nat. Biotechnol.* 23:1137-1146 (2005)). In some embodiments, the antibody fragment is part of a diabody. In some embodiments, the invention provides high avidity antibodies for use according to the invention.

Diabodies, first described by Hollinger et al., PNAS (USA) 90(14): 6444-6448 (1993), may be constructed using heavy and light chains disclosed herein, as well as by using individual CDR regions disclosed herein. Typically, diabody fragments comprise a heavy chain variable domain (V$_H$) connected to a light chain variable domain (V$_L$) by a linker which is too short to allow pairing between the two domains on the same chain. Accordingly, the V$_H$ and V$_L$ domains of one fragment are forced to pair with the complementary V$_H$ and V$_L$ domains of another fragment, thereby forming two antigen-binding sites. Triabodies can be similarly constructed with three antigen-binding sites. An Fv fragment contains a complete antigen-binding site which includes a V$_L$ domain and a V$_H$ domain held together by non-covalent interactions. Fv fragments embraced by the present invention also include constructs in which the V$_H$ and V$_L$ domains are crosslinked through glutaraldehyde, intermolecular disulfides, or other linkers. The variable domains of the heavy and light chains can be fused together to form a single chain variable fragment (scFv), which retains the original specificity of the parent immunoglobulin. Single chain Fv (scFv) dimers, first described by Gruber et al., *J. Immunol.* 152 (12):5368-74 (1994), may be constructed using heavy and light chains disclosed herein, as well as by using individual CDR regions disclosed herein. Many techniques known in the art can be used to prepare the specific binding constructs of the present invention (see, U.S. Patent Application Publication No. 20070196274 and U.S. Patent Application Publication No. 20050163782, which are each herein incorporated by reference in their entireties for all purposes, particularly with respect to minibody and diabody design).

Bispecific antibodies can be generated by chemical cross-linking or by the hybrid hybridoma technology. Alternatively, bispecific antibody molecules can be produced by recombinant techniques (see: bispecific antibodies). Dimersation can be promoted by reducing the length of the linker joining the VH and the VL domain from about 15 amino acids, routinely used to produce scFv fragments, to about 5 amino acids. These linkers favor intrachain assembly of the VH and VL domains. A suitable short linker is SGGGS but other linkers can be used. Thus, two fragments assemble into a dimeric molecule. Further reduction of the linker length to 0-2 amino acids can generate trimeric (triabodies) or tetrameric (tetrabodies) molecules.

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4:72 (1983); Cole et al., in *Monoclonal Antibodies and Cancer Therapy*, Alan R. Liss, Inc., pp. 77-96 (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

As an example, polyclonal antibodies to EMP2 may be obtained using glutathione-S-transferase-EMP2 fusion proteins. Antibodies can be generated against the first extracellular region of the gene (from amino acid 16 to 64) constructed as a glutathione-S-transferase (GST)-EMP2 fusion protein. The EMP2 peptide can be cloned by PCR using the following primers: CGC GGATCCTCTACCATTGACAATGCCTGG (SEQ ID NO: 31) (forward; BamH1 underlined); CCG GAATTCTTACGCCTGCATCACAGAATAACC (SEQ ID NO: 32) (reverse, EcoR1 underlined). The PCR product can be directionally cloned into the BamHI and EcoRI sites of the pGEX-4T-1 vector that contains the GST gene (Pharmacia). The EMP2 fragment is cloned in frame with the GST to create a fusion protein. The insert can be confirmed by sequencing. The GST fusion protein can be produced as previously described (see, Smith D B et al., Gene 67:31-40 (1988)). Bacteria in log phase ($OD_{600}$ 0.6 to 0.9) can be induced for 2.5 to 3 hours at 37° C. with 1 mM isopropyl-1-thio-β-D-galactopyranoside. Bacteria are lysed, and the soluble fraction loaded onto a glutathione-Sepharose column (Pierce, Rockford, Ill.). The columns are washed with 10 bed volumes of phosphate-buffered saline (PBS)/EDTA. The fusion protein elutes from the column using 20 mM reduced glutathione (Sigma, St Louis, Mo.) in 50 mM Tris-Cl, pH 8.0. For antibody preparation, rabbits are immunized twice with the GST-EMP2 fusion protein, and serum is collected, starting 2 weeks after the last immunization (Research Genetics, Huntsville, Ala.).

Fully human monoclonal antibodies to EMP2 can be produced using recombinant phage-display technology from a human antibody phage-display gene library. Such monoclonal antibodies to human EMP2 can be used for diagnostic purposes, and for prevention or treatment of retinal detachments as in PVR.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher et al., *J. Biol. Chem.* 273(52):35095-35101 (1998).

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length.

The design and making of siRNA molecules and vectors are well known to those of ordinary skill in the art. For instance, an efficient process for designing a suitable siRNA is to start at the AUG start codon of the mRNA transcript (e.g., see, FIG. 5) and scan for AA dinucleotide sequences (see, Elbashir et al., EMBO J. 20:6877-6888 (2001)). Each AA and the 3' adjacent nucleotides are potential siRNA target sites. The length of the adjacent site sequence will determine the length of the siRNA. For instance, 19 adjacent sites would give a 21 Nucleotide long siRNA siRNAs with 3' overhanging UU dinucleotides are often the most effective. This approach is also compatible with using RNA pol III to transcribe hairpin siRNAs. RNA pol III terminates transcription at 4-6 nucleotide poly(T) tracts to create RNA molecules having a short poly(U) tail. However, siRNAs with other 3' terminal dinucleotide overhangs can also effectively induce RNAi and the sequence may be empirically selected. For selectivity, target sequences with more than 16-17 contiguous base pairs of homology to other coding sequences can be avoided by conducting a BLAST search (see, www.ncbi.nlm.nih.gov/BLAST).

The siRNA can be administered directly or an siRNA expression vectors can be used to induce RNAi. A vector can have inserted two inverted repeats separated by a short spacer sequence and ending with a string of T's which serve to terminate transcription. The expressed RNA transcript is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary. A preferred order of the siRNA expression cassette is sense strand, short spacer, and antisense strand. Hairpin siRNAs with these various stem lengths (e.g., 15 to 30) are suitable. The length of the loops linking sense and antisense strands of the hairpin siRNA can have varying lengths (e.g., 3 to 9 nucleotides, or longer). The vectors may contain promoters and expression enhancers or other regulatory elements which are operably linked to the nucleotide sequence encoding the siRNA.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. These control elements may be designed to allow the clinician to turn off or on the expression of the gene by adding or controlling external factors to which the regulatory elements are responsive.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, including EMP2 polynucleotides and EMP2 polypeptides, refer to two or more sequences or subsequences that are the same or have a specified percentage of amino acid residues or nucleotides that are the same (i.e., about 60% identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al.

(1990) *PCR Protocols, A Guide to Methods and Applications*, Academic Press, Inc. N.Y.).

The EMP2 antibody or EMP2 polypeptide according to the invention can have a label or detectable moiety attached thereto. A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "biological sample" includes sections of tissues such as biopsy and autopsy samples, and frozen sections taken for histological purposes. Such samples include blood and blood fractions of products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, or mouse; rabbit; bird; reptile; or fish.

The terms "treating" or "treatment" include:
(1) preventing the disease, i.e., causing the clinical symptoms of the disease not to develop in a mammal that may be exposed to the organism but does not yet experience or display symptoms of the disease;
(2) inhibiting the disease, i.e., arresting or reducing the development of the disease or its clinical symptoms. This includes reducing the extent of the detachment observed or the numbers of subjects or risk of a subject having a detachment; and/or
(3) relieving the disease, i.e., causing regression of the disease or its clinical symptoms.

By "therapeutically effective dose or amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy,* 20th Edition, Gennaro, Editor (2003), and Pickar, *Dosage Calculations* (1999)).

A "patient" or "subject" refers to humans and non-human animals, e.g., mammals (e.g., primates, cows, horses, cats, dogs, rabbits, mice, and rats). Thus the methods of the present invention are applicable to both human therapy and veterinary applications.

A "pharmaceutically acceptable salt" is meant to include salts of the active compounds which are prepared with relatively nontoxic acids or bases, according to the route of administration. When inhibitors of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Aside from biopolymers such as nucleic acids and polypeptides, certain compounds of the present invention possess asymmetric carbon atoms (optical centers) or double bonds; the racemates, diastereomers, geometric isomers and individual isomers are all intended to be encompassed within the scope of the present invention. In preferred embodiments, wherein the compound comprises amino acids or nucleic acids, the amino acids and nucleic acids are each the predominant naturally occurring biological enantiomer.

As used herein, the term "carrier" refers to a typically inert substance used as a diluent or vehicle for an active agent to be applied to a biological system in vivo or in vitro.

(e.g., drug such as a therapeutic agent). The term also encompasses a typically inert substance that imparts cohesive qualities to the composition.

II. Anti-EMP2 Compositions

The present invention provide compositions for inhibiting the activity of an EMP2 polypeptide, said compositions having use in methods of treating proliferative vitreoretinopathy or retinal detachment in an eye of a subject. Without being bound to a particular theory, it is believed that EMP2 positively modulates cellular contraction, which in retinal pigment epithelium cells may lead to retinal detachment and vision loss. Accordingly, the present invention provides methods of preventing and/or treating cellular contraction and retinal detachment by providing an anti-EMP2 agent.

In some embodiments, the anti-EMP2 agent comprises an anti-EMP2 antibody or fragment thereof. In some embodiments, the anti-EMP2 agent comprises an EMP2 inhibitory oligonucleotide, e.g., an anti-EMP2 siRNA or an anti-EMP2 ribozyme.

A. Anti-EMP2 Antibodies

The present invention identifies antibody sequences encoding high-avidity antibodies specific for human (KS49, KS83) and mouse (KS83) EMP2 polypeptide. The identified sequences are useful for producing recombinant anti-EMP2 antibodies (e.g., monoclonal antibodies, polyclonal antibodies, minibodies, dibodies, and tribodies) or fragments thereof for imaging, diagnostic methods, or in vivo therapy.

In some embodiments, an anti-EMP2 antibody or fragment thereof is one that is capable of specifically binding to an EMP2 polypeptide that is substantially identical (i.e., has greater than about 60%, 65%, 70%, 75%, 80%, 85%, 90%, 91%, 92%, 93%, 94%, 95%, 96%, 97%, 98% or 99% or greater amino acid sequence identity, over a region of at least about 15, 20, 25, 50, 100, 200, 500, 1000, or more amino acids) to SEQ ID NO:1, SEQ ID NO:2, or SEQ ID NO:30. In some embodiments, an anti-EMP2 antibody or fragment thereof is capable of specifically binding to an EMP2 polypeptide having the amino acid sequence of SEQ ID NO:1, SEQ ID NO:2, or SEQ ID NO:30.

In some embodiments, an anti-EMP2 antibody or fragment thereof comprises a heavy chain comprising an amino acid sequence with at least 60%, 65%, 70%, 75%, 80%, 85%, 90%, 91%, 92%, 93%, 94%, 95%, 96%, 97%, 98% or 99% sequence identity to KS49 heavy chain (SEQ ID NO:4) and/or a light chain comprising an amino acid sequence with at least 60%, 65%, 70%, 75%, 80%, 85%, 90%, 91%, 92%, 93%, 94%, 95%, 96%, 97%, 98% or 99% sequence identity to KS49 light chain (SEQ ID NO:5). In some embodiments, an anti-EMP2 antibody comprises a heavy chain having the amino acid sequence of SEQ ID NO:4 and/or a light chain having the amino acid sequence of SEQ ID NO:5.

In some embodiments, an anti-EMP2 antibody or fragment thereof comprises a heavy chain comprising an amino acid sequence with at least 60%, 65%, 70%, 75%, 80%, 85%, 90%, 91%, 92%, 93%, 94%, 95%, 96%, 97%, 98% or 99% sequence identity to KS83 heavy chain (SEQ ID NO:6) and/or a light chain comprising an amino acid sequence with at least 60%, 65%, 70%, 75%, 80%, 85%, 90%, 91%, 92%, 93%, 94%, 95%, 96%, 97%, 98% or 99% sequence identity to KS83 light chain (SEQ ID NO:7). In some embodiments, an anti-EMP2 antibody comprises a heavy chain having the amino acid sequence of SEQ ID NO:6 and/or a light chain having the amino acid sequence of SEQ ID NO:7.

In some embodiments, an anti-EMP2 antibody or fragment thereof comprises a heavy chain comprising an amino acid sequence with at least 60%, 65%, 70%, 75%, 80%, 85%, 90%, 91%, 92%, 93%, 94%, 95%, 96%, 97%, 98% or 99% sequence identity to KS41 heavy chain (SEQ ID NO:8) and/or a light chain comprising an amino acid sequence with at least 60%, 65%, 70%, 75%, 80%, 85%, 90%, 91%, 92%, 93%, 94%, 95%, 96%, 97%, 98% or 99% sequence identity to KS41 light chain (SEQ ID NO:9). In some embodiments, an anti-EMP2 antibody comprises a heavy chain having the amino acid sequence of SEQ ID NO:8 and/or a light chain having the amino acid sequence of SEQ ID NO:9.

In some embodiments, an anti-EMP2 antibody or fragment thereof comprises a heavy chain comprising an amino acid sequence with at least 60%, 65%, 70%, 75%, 80%, 85%, 90%, 91%, 92%, 93%, 94%, 95%, 96%, 97%, 98% or 99% sequence identity to KS89 heavy chain (SEQ ID NO:10) and/or a light chain comprising an amino acid sequence with at least 60%, 65%, 70%, 75%, 80%, 85%, 90%, 91%, 92%, 93%, 94%, 95%, 96%, 97%, 98% or 99% sequence identity to KS89 light chain (SEQ ID NO:11). In some embodiments, an anti-EMP2 antibody comprises a heavy chain having the amino acid sequence of SEQ ID NO:10 and/or a light chain having the amino acid sequence of SEQ ID NO:11.

In some embodiments, the present invention provides anti-EMP2 sequences comprising CDR regions of an antibody selected from KS49, KS83, KS41, and KS89. The CDR regions provided by the invention may be used to construct an anti-EMP-2 antibody or fragment thereof, including but not limited to an antibody, a scFv, a triabody, a diabody, a minibody, and the like. In some embodiments, an anti-EMP-2 binding protein of the invention comprises at least one CDR region from an antibody selected from KS49, KS83, KS41, and KS89. Anti-EMP-2 binding proteins may comprise, for example, a CDR-H1, a CDR-H2, a CDR-H3, a CDR-L1, a CDR-L2, a CDR-L3, or combinations thereof, from an antibody provided herein. In some embodiments of the invention, an anti-EMP2 antibody or fragment thereof may comprise all three CDR-H sequences of an antibody provided herein, all three CDR-L sequences of an antibody provided herein, or both. Anti-EMP2 CDR sequences may be used on an antibody backbone, or fragment thereof, and likewise may include humanized antibodies, or antibodies containing humanized sequences. These antibodies may be used, for example, to detect EMP2, to detect cells expressing EMP-2 in vivo, or to block EMP2 function. In some embodiments, the CDR regions may be defined using the Kabat definition, the Chothia definition, the AbM definition, the contact definition, or any other suitable CDR numbering system.

In some embodiments, the anti-EMP2 antibody or fragment thereof comprises a heavy chain region comprising a CDR-H1 having an amino acid sequence selected from the group consisting of SYAMH (SEQ ID NO:12) and EYPMH (SEQ ID NO:22); a CDR-H2 having an amino acid sequence selected from the group consisting of VISYDGSNKYY-ADSVKG (SEQ ID NO:13) and VISYDGEYQKYADS-VKG (SEQ ID NO:23); and a CDR-H3 having an amino acid selected from the group consisting of DRRGRKSAG-IDY (SEQ ID NO:14), TVGATGAFDI (SEQ ID NO:18), and TINNGMDV (SEQ ID NO:24).

In some embodiments, the anti-EMP2 antibody or fragment thereof comprises a light chain region comprising a CDR-L1 having an amino acid sequence selected from the group consisting of QASQDISNYLN (SEQ ID NO:15), RASQSIGKWLA (SEQ ID NO:19), and RASQGIRNDLG (SEQ ID NO:25); a CDR-L2 having an amino acid sequence selected from the group consisting of AASSLQS (SEQ ID NO:16), KASSLEG (SEQ ID NO:20), and GASSLQS (SEQ ID NO:26); and a CDR-L3 having an amino acid sequence selected from the group consisting of LQDYNGWT (SEQ ID NO:17) and QQSHNFPPT (SEQ ID NO:21).

In some embodiments, an anti-EMP2 antibody or fragment thereof that is capable of specifically binding to an EMP2 polypeptide comprises an amino acid sequence having at least 60%, 65%, 70%, 75%, 80%, 85%, 90%, 91%, 92%, 93%, 94%, 95%, 96%, 97%, 98% or 99% amino acid sequence identity to an antibody of SEQ ID NOs:27-29.

B. Anti-EMP2 Oligonucleotides

In some embodiments, EMP2 activity is inhibited by administering an anti-EMP2 oligonucleotide. In some embodiments, the anti-EMP2 oligonucleotide is an EMP2 siRNA, wherein the EMP2 siRNA is capable of reducing the expression of a polynucleotide that encodes an EMP2 polypeptide. In some embodiments, the anti-EMP2 oligonucleotide is an EMP2 ribozyme, wherein the EMP2 ribozyme is capable of inhibiting the expression of EMP2 in a cell.

In some embodiments, an EMP2 siRNA comprises an oligonucleotide that specifically hybridizes to a polynucleotide having substantial identity (i.e., having greater than about 60%, 65%, 70%, 75%, 80%, 85%, 90%, 91%, 92%, 93%, 94%, 95%, 96%, 97%, 98% or 99% or greater nucleotide sequence identity) to the nucleic acid sequence of SEQ ID NO:3 or its complement. In some embodiments, an EMP2 siRNA comprises a nucleic acid sequence that is substantially identical to at least 15, 18, 20, 25, 30, 35, 40, 45, 50 contiguous nucleotides or greater of the nucleic acid sequence of SEQ ID NO:3 or a complement thereof.

In some embodiments, the EMP2 inhibitor is an EMP2 ribozyme. Ribozymes are enzymatic RNA molecules capable of catalysing the specific cleavage of RNA. The mechanism of ribozyme action involves sequence specific hybridization of the ribozyme molecule to complementary target RNA, followed by an endonucleolytic cleavage. Within the scope of the invention are engineered hammerhead motif ribozyme molecules that specifically and efficiently catalyse endonucleolytic cleavage of EMP2 mRNA, including mRNA having substantial identity (i.e., having greater than about 60%, 65%, 70%, 75%, 80%, 85%, 90%, 91%, 92%, 93%, 94%, 95%, 96%, 97%, 98% or 99% or greater nucleotide sequence identity) to the nucleic acid sequence of SEQ ID NO:3.

Specific ribozyme cleavage sites within any potential RNA target are initially identified by scanning the target molecule for ribozyme cleavage sites, which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Methods of making ribozymes are well known in the art (see, for instance, U.S. Patent Application Publication No. 20060062785).

Construction of suitable vectors for EMP2 siRNA or EMP2 ribozymes containing the desired EMP2 siRNA or EMP2 ribozyme sequences and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

C. Formulations

The compositions for administration according to the methods of treatment as described herein will commonly comprise an anti-EMP2 agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Suitable formulations for use in the present invention are found in *Remington: The Science and Practice of Pharmacy*, 20th Edition, Gennaro, Editor (2003) which is incorporated herein by reference. Moreover, for a brief review of methods for drug delivery, see, Langer, Science 249:1527-1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the inhibitors for use according to the invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

In some embodiments, a pharmaceutical composition for intravenous administration may provide from about 0.1 to 100 mg per patient per day. Dosages from 0.1 up to about 100 mg per patient per day may be used. Substantially higher dosages are possible in topical administration. Actual methods for preparing parenterally administrable compositions will be known or apparent to those skilled in the art and are described in more detail in such publications as *Remington: The Science and Practice of Pharmacy*, 21st Edition 2005, Lippincott Williams & Wilkins, Publishers.

The pharmaceutical compositions can be administered in a variety of dosage forms and amounts depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, of the polypeptide and nucleic acid EMP2 inhibitors for according to the present invention can be prepared by mixing an antibody or oligonucleotide having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid); preservatives; low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The antibody can be formulated at a concentration of between 0.5-200 mg/ml, or between 10-50 mg/ml.

In some embodiments, the invention provides a composition comprising an EMP2 inhibitor and a physiologically acceptable carrier at the cellular or organismal level. Typically, a physiologically acceptable carrier is present in liquid, solid, or semi-solid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Examples of solid or semi-solid carriers include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. Since physiologically acceptable carriers are determined in part by the particular composition being administered as well as by the particular method used to administer the composition, there are a wide variety of suitable formulations of pharmaceutical compositions of the present invention (see, e.g., *Remington's Pharmaceutical Sciences*, $17^{th}$ ed., 1989). The carriers and compositions are preferably sterile.

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically or physiologically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged platinum-based drug suspended in diluents, e.g., water, saline, or PEG 400; (b) capsules, sachets, or tablets, each containing a predetermined amount of a platinum-based drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

The present invention provides topical pharmaceutical compositions comprising an EMP2 inhibitor according to the invention. In some embodiments, the inhibitor is a small organic compound, an EMP2 polypeptide, or anti-EMP2 antibody. The inhibitor may be in a unit dosage form comprising per unit dosage an amount of a EMP2 inhibitor as provided above which is effective for the condition of interest.

Topical formulations of EMP2 inhibitors may be formulated in combination with a pharmaceutically acceptable carrier. Dosage forms for the topical administration of the compounds of this invention include powders, sprays, foams, jellies, ointments, pastes, creams, lotions, gels, solutions, patches, suppositories and liposomal preparations. The dosage forms may be formulated with mucoadhesive polymers for sustained release of active ingredients at the urogenital area. The active compound may be mixed under sterile conditions with a pharmaceutically acceptable carrier, and with any preservatives, buffers, or propellants, which may be required. Topical preparations can be prepared by combining the inhibitor t with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Lotions may be formulated with an aqueous or oily base and, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or nonaqueous base also comprising one or more dispersing agents, suspending agents, solubilizing agents, and the like.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The EMP2 inhibitor may be present in the composition in unit dosage form effective for the treatment of the condition. The dosage of a EMP2 inhibitor depends upon many factors that are well known to those skilled in the art, for example, the particular compound; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

The invention provides topical sustained and prolonged release pharmaceutical compositions comprising one or more pharmacological compounds described supra, and a pharmaceutically acceptable carrier. Preferably, the compositions are administered in unit dosage form to a subject in need of such treatment. Topical sustained and prolonged release compositions are typically variants which include 1) an absorbent in a hydrophilic base; 2) an absorbent in a hydrophobic base; and 3) coated beads containing an absorbent matrix dispersed in a suitable vehicle.

III. Methods of Treatment

The present invention further relates to methods of treating, preventing, and/or inhibiting retinal detachment in an eye of a subject having retinal detachment or proliferative vitreoretinopathy. The methods generally comprise administering an anti-EMP2 agent (e.g., an anti-EMP2 antibody or fragment thereof, an anti-EMP2 siRNA, or an anti-EMP2 ribozyme) as described herein to the subject under conditions and at a dose sufficient for reducing and/or inhibiting EMP2 activity in the eye.

A physician or veterinarian can start doses of the anti-EMP2 agents of the invention employed in the pharmaceutical composition at levels lower than that required to achieve the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. Single or multiple administrations of the compositions may be administered depending on the dosage and frequency as required and tolerated by the patient.

For administration with an antibody, the dosage ranges from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg. Dosing can be daily, weekly, bi-weekly, monthly, or more or less often, as needed or desired. An exemplary treatment regime entails administration once weekly, once per every two weeks or once a month or once every 3 to 6 months.

In embodiments where the agent is a nucleic acid, typical dosages can range from about 0.1 mg/kg body weight up to and including about 100 mg/kg body weight, e.g., between about 1 mg/kg body weight to about 50 mg/kg body weight. In some embodiments, about 1, 2, 3, 4, 5, 10, 15, 20, 30, 40 or 50 mg/kg body weight.

The anti-EMP2 agents of the present invention and pharmaceutical compositions thereof may be administered by any route of administration (e.g., intravenous, topical, intraperitoneal, parenteral, oral, intravaginal, rectal, ocular, intravitreal and intraocular). They may be administered as a bolus or by continuous infusion over a period of time, by intramuscular, intraperitoneal, subcutaneous, oral, topical, or inhalation routes. Intravenous or subcutaneous administration of the antibody is preferred. The administration may be local or systemic. They may be administered to a subject who has been diagnosed with the subject disease, a history of the disease, or is at risk of the disease.

EXAMPLES

The following examples are provided to illustrate, but not to limit the claimed invention.

Example 1

Proliferative vitreoretinopathy (PVR) is thought to result in part from de-differentiation of retinal pigment epithelium (RPE) with cellular migration in the vitreous cavity, membrane formation, and contraction in an aberrant wound-healing strategy. In an in vitro collagen-gel contraction assay, epithelial membrane protein 2 (EMP2), a four transmembrane protein, controls contraction through activation of focal adhesion kinase (FAK) by a retinal pigment epithelium cell line (ARPE-19) was studied. The purpose of this study was to investigate whether the level of EMP-2 expression changed clinical PVR in an in vivo model system.

Methods:

ARPE-19 cell line was obtained from the ATCC, and the levels of EMP2 modulated through stable transfections of an EMP-2 overexpressing construct, EMP2 ribozyme, or vector alone. These stable transfected cell lines were used in a rabbit model of PVR. The severity of PVR was classified by two masked observers. An EMP2 blocking antibody was also used to decrease functional EMP2 in the PVR model. Immunohistochemistry was used to evaluate EMP2 expression in vivo.

Results:

The transfectants with high levels of EMP2 expression induced significantly greater severity of PVR than the low-level EMP2 transfectants (p=0.05). In addition, the transfectants with lower levels of EMP2 had significantly less PVR severity than the degree of PVR induced by wild-type cells. (p=0.02) Blocking EMP2 with a specific antibody significantly decreased the level of PVR severity (p=0.01). PVR membranes were found to positive for EMP2 expression.

Conclusions:

These in vivo studies support a direct correlation between EMP2 expression and severity of PVR. These results validate the potential for controlling RPE biology through a change in EMP2 expression, and provide a potential therapeutic target for this disease.

Control of the RPE and prevention of membrane contraction is a primary goal in the prevention of the devastating PVR response. In an in vitro experimental model, our laboratory identified activation of FAK through ligation of integrins ($\alpha1$, $\alpha2$, and $\alpha3$) as a critical control point for collagen gel contraction (Morales, S. A. et al., Exp Eye Res 85:790-8 (2007)). The tetraspan superfamily are a key class of proteins that determine the types of intracellular trafficking and signaling molecules assembled with integrins and other receptor complexes (Hemler, M. E. T Annu Rev Cell Dev Biol 19:397-422 (2003)). The particular tetraspan family members are highly controlled in individual cell types and states of differentiation or activation. Accordingly, combinatorial expression of tetraspans is an important contributor to integrin deployment and signaling quality. Epithelial membrane protein-2 (EMP2) is a tetraspan family member, which acts to control specific integrin deployment and signaling though FAK (Morales, S. A. et al., Invest Ophthalmol Vis Sci 50:462-9 (2009)). EMP2, highly expressed in RPE (Wadehra, M. et al., Exp Mol Pathol 74:106-12 (2003)), is a member of the growth arrest specific gene 3/peripheral myelin protein 22 (GAS3/PMP22) 4-TM protein family with distinctive biochemical and physiological roles (Wadehra, M. et al., Exp Mol Pathol 74:106-12 (2003); Forbes, A. et al., J Biol Chem 282:26542-51 (2007); Wadehra, M. et al., Mol Biol Cell 15:2073-83 (2004); Wadehra, M. et al., J Biol Chem 277:41094-100 (2002); Wadehra, M. et al., Reprod Biol Endocrinol 6:15 (2008); Wadehra, M. et al., Clin Immunol 107:129-36 (2003); Wang, C. X. et al., Blood 97:3890-5 (2001)).

In this study, we used the rabbit model of PVR to study the role EMP2 expression plays in the development and progression of PVR and retinal detachment. We found that decreased expression of EMP2 or blocking EMP2 by antibodies resulted in decreased PVR formation.

Methods and Materials

Cell Lines:

Stable ARPE-19 Cell line, ARPE-19 is a spontaneously arising human retinal pigment epithelia (RPE) obtained from ATCC(CRL-2302). ARPE-19 cells were transfected in with one of the following constructs: pEGFP-N3=vector control, pEGFP-N3-EMP2=EMP2 over expressing construct, pEGFP-N-3-Ribo1=EMP2 reduced expression construct. ARPE-19 cells were plated 24 hours prior to transfection. The cells were transfected with one of the above constructs using FuGENE 6 (Roche Molecular Biochemicals, Indianapolis, Ind.). Stable clones were selected using Geneticin (700 mg/ml, Invitrogen Life Technologies); these stable cell lines are referred to as ARPE-19/V, ARPE-19/EMP2, or ARPE-19/Ribo. Expression of EMP-2 by these cell lines was previously reported (Morales, S. A. et al., Invest Ophthalmol Vis Sci 50:462-9 (2009)).

Growth Media:

ATCC medium #30-2006: A 1:1 mixture of Dulbecco's modified Eagle's medium and Ham's F12 medium containing 1.2 g/L sodium bicarbonate, 2.5 mM L-glutamine, 15 mM HEPES and 0.5 mM sodium pyruvate, 90%; fetal bovine serum #30-2020, 10%.

Animal Model of PVR:

Rabbits used in this study were treated in accordance to institutional guidelines approved by the UCLA Institutional Review Board (IRB). PVR was induced only in the right eye of albino New Zealand rabbits as previously described (Nakagawa, M. et al., Invest Ophthalmol Vis Sci 36:2388-95 (1995)). Briefly, using a 30-gauge needle 0.4 ml of C3F8 gas (100%) was injected into the vitreous cavity 4 mm posterior to the corneal limbus after anesthesia was induced. Anterior paracentesis was performed with a microblade to prevent elevated intraocular pressures. Two days later ARPE-19 cell preparations resuspended in growth media were injected in a volume of 0.1 cc. The left eye served as a control. The rabbits were examined weekly in a masked fashion by indirect ophthalmoscopy for PVR development and inflammation. At 5 weeks the animals were sacrificed using Pentobarbital (100 mg/kg). Globes were placed in 10% formalin and a superior pars plana incision was made with an #11 blade to allow access of the fixative in the intraocular space. The globes were fixed for 3 days, bisected and scored in a masked fashion for gross pathology using the PVR scale established by Fastenberg (Table 1) (Fastenberg, D. M. et al., Am J Ophthalmol 95:663-7 (1983); Fastenberg, D. M. et al., Am J Ophthalmology 93:565-72 (1982)). The globes were embedded in paraffin, sectioned and stained with hematoxylin and eosin. Sections were microscopically evaluated and graded for PVR in a masked fashion.

Statistical Analysis:

A Student's t-test (unpaired, one-tail) was used and a $P<0.05$ was judged to be statistically significant.

TABLE 1

The Fastenberg classification of the five stages of massive preretinal proliferation.

| GRADE | Findings on Retinal Fundus Exam |
|---|---|
| 1 | Intravitreal Membrane |
| 2 | Focal traction, localized vascular changes; hyperemia; engorgement; dilation; blood vessel elevation. |
| 3 | Localized detachment of medullary ray |
| 4 | Extensive retinal detachment; total medullary ray detachment; Peripapillary retinal detachment |
| 5 | Total retinal detachment; retinal folds and holes |

Results

Figure 2:
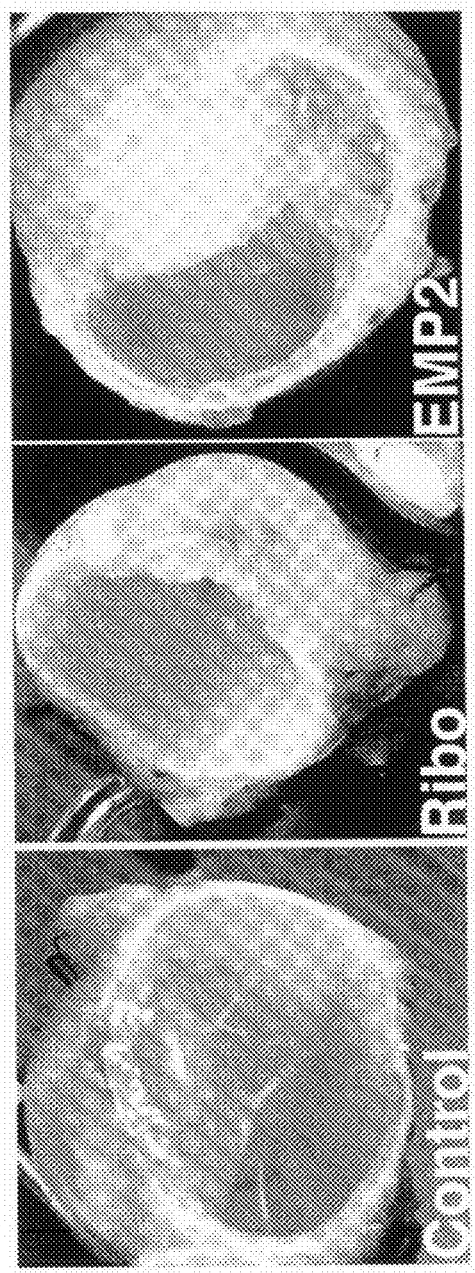
FIG. 2. Gross pathologic sections of globes isolated from the experiment shown in FIG. 1. Degrees of PVR membrane formation can be seen in these images. One globe is shown from each group. As in FIG. 1: Control—rabbits that received ARPE19 cells transfected with the vector alone; Ribo—rabbits that received ribozyme-transfected cells with lower expression of EMP2; EMP2—rabbits that received cells transfected to overexpress EMP2. The rabbits that received cells overexpressing EMP2 had increased rates of PVR membrane formation whereas the animals that received the cells with lower levels of EMP2 expression by ribozyme knockdown (Ribo) had decreased degrees of PVR membrane formation. The results presented were obtained at 5 weeks after cell injection.

Increased PVR Formation with Increased EMP-2 Expression:

Using the well-characterized rabbit model of PVR, we induced PVR with intravitreal injections of ARPE-19 cells as described (Nakagawa, M. et al., *Invest Ophthalmol Vis Sci* 36:2388-95 (1995)). The cells were either wild-type, modified ARPE-19 cells over-expressing EMP2 or under-expressing EMP2 by ribozyme transfection (Morales, S. A. et al., *Invest Ophthalmol Vis Sci* 50:462-9 (2009)). Eyes were graded for the degree of PVR formation by 2 observers at 5 weeks after injection. Initial 3 rabbits were found to have consistent degrees of PVR formation similar to previous reports (data not shown). Rabbits given wild type RPE cells had significantly more severe levels of PVR than those given the EMP2 under-expressing cells (2.5 vs. 1.3 respectively, p=0.02). (FIG. 1) Moreover, the rabbits given the EMP2 over-expressing cells had significantly more PVR formation than those under-expressing EMP-2 (2.9 vs. 1.3 respectively, p=0.05) Increased EMP2 expression was associated with an increased PVR severity and concordantly, decreased EMP2 levels reduced PVR severity. FIG. 2 shows typical gross histologic specimens from the three different groups of rabbits.

Figure 3:
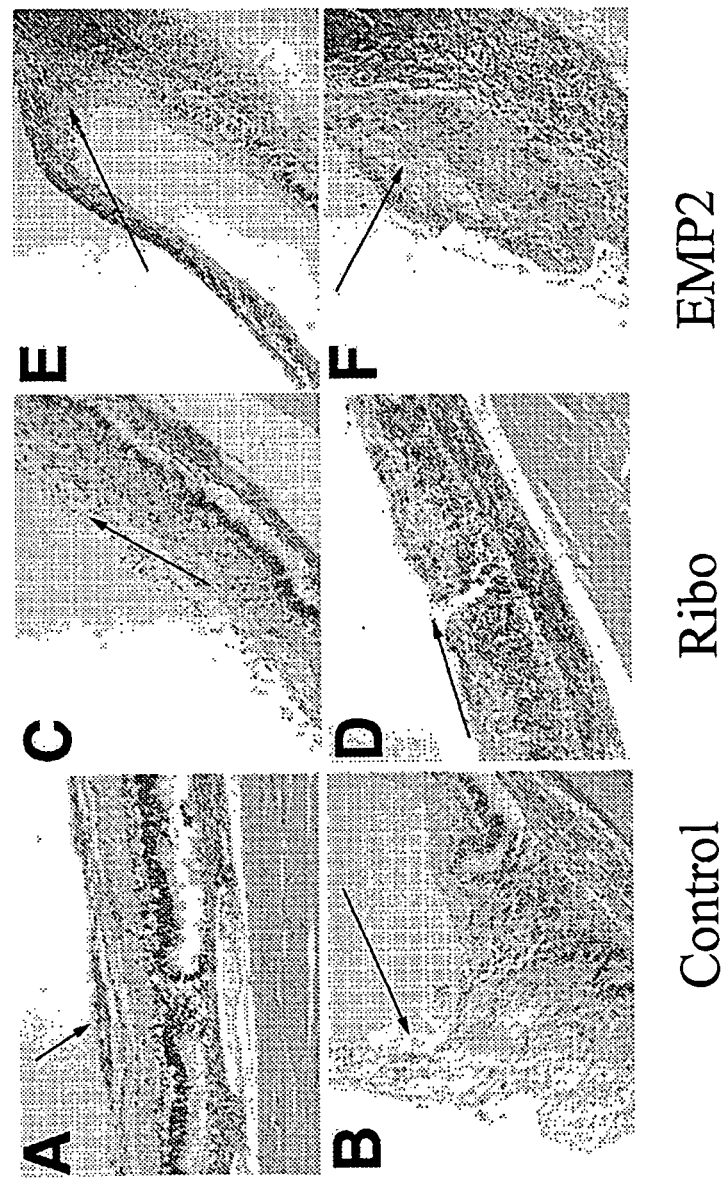
FIG. 3. Histology sections showing pre-retinal membranes from the experiment shown in FIGS. 1 and 2. As in FIGS. 1 and 2: Control—rabbits that received ARPE19 cells transfected with the vector alone (A, B); Ribo—rabbits that received ribozyme-transfected cells with lower expression of EMP2 (C, D); EMP2—rabbits that received cells transfected to overexpress EMP2 (E, F). Arrows point to the preretinal membranes, which were more prominent in control (A, B) and EMP2 (C, D) groups than in Ribo groups (E, F).
Figure 4:
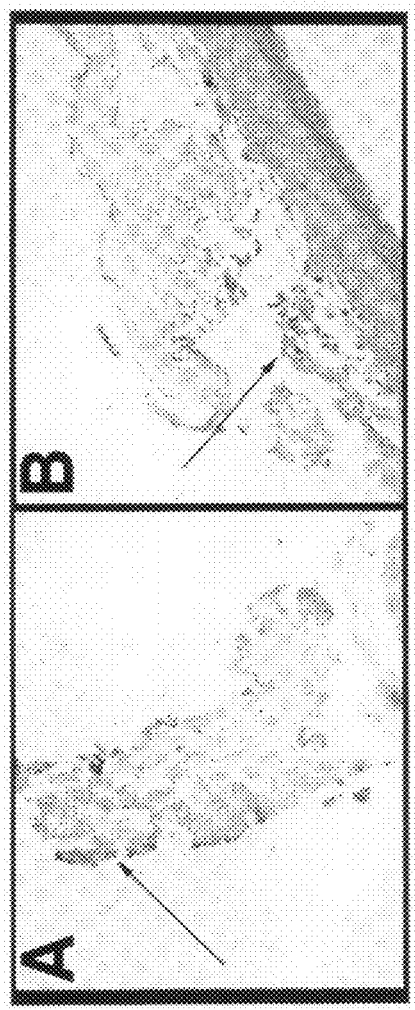
FIG. 4. EMP2 Expression found in pre-retinal membranes. Pre-retinal PVR membranes were most prominent in Control and EMP2 rabbit groups (FIG. 1-3). This figure shows EMP2 expression (violet) from in a control rabbit (A) and from an EMP2 overexpressing rabbit (B).

Increased Fibrosis and Membrane Formation with Increased EMP-2 Expression:

Histologic examination of eyes given EMP2 over-expressing cells confirmed greater PVR membrane formation than both rabbits that received wild-type or low EMP2 expressing (Ribozyme-transfected) cells (FIG. 3). The in vivo PVR membranes were found to be positive for EMP2 expression at 5 weeks by immunohistochemistry (FIG. 4).

Figure 5:
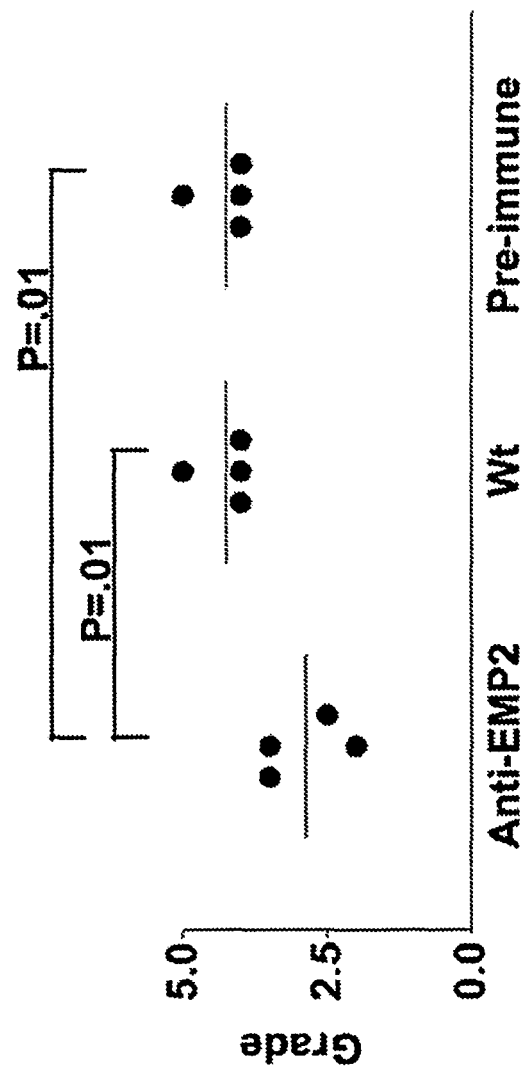
FIG. 5. Rabbit model of PVR shows inhibition of PVR membrane formation when cells pre-incubated with anti-EMP2 polyclonal antibody. 3 rabbits were in each group: Anti-EMP2—rabbits that received ARPE19 cells pre-incubated with polyclonal anti-EMP2 antibody; Wild-type (Wt)—rabbits that received wild-type ARPE19 cells; Pre-immune—rabbits that received ARPE19 cells pre-incubated with polyclonal pre-immune (control) antibody. The results presented were obtained 5 weeks after cell injection. Student T-test p values shown above compared groups.
Figure 6:
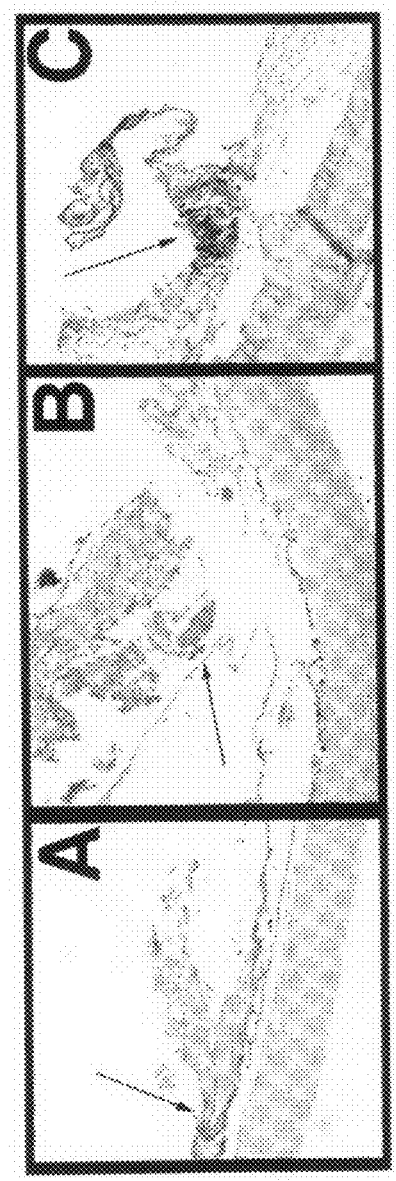
FIG. 6. EMP2 expression found in pre-retinal membranes.

PVR Membrane Formation Blocked with EMP-2 Blocking Antibody:

ARPE-19 cells were pre-incubated with either polyclonal anti-human EMP2 antibody, control antibody (pre-immune sera), or media alone. Eyes were again examined 5 weeks after cell injections. The degree of PVR formation was graded by two masked observers. Blockade of EMP2 in the ARPE-19 cells using the anti-human polyclonal EMP2 antibody decreased PVR severity as compared to untreated cells or cells exposed to the preimmune control antibody (2.6 vs. 4.3 respectively, p=0.01) (FIG. 5). Additionally, histologic evaluation confirmed decreased fibrosis and traction (FIG. 6). EMP2 expression was observed in the remaining membranes as predicted by our prior in vivo work in a mouse model that documented a transient decrease in EMP2 expression following ligation with a specific antibody (Shimazaki, K. et al., *Microbes Infect* 9:1003-10 (2007)).

Discussion

Initially during the development of PVR, RPE cells are thought to bind to the retinal surface, migrate, proliferate and form membranes (Eibl, K. H. et al., *Invest Ophthalmol Vis Sci* 47:364-70 (2006)). This is then followed by membrane contraction and tractional retinal detachment.

In this study, we extend the in vitro evidence that EMP2 plays an important regulatory role in membrane contraction and present evidence for the relevance of EMP2 expression in vivo in the rabbit PVR models. Gel contration assays showed increased contraction of collagen gel with increased EMP2 expression (Morales, S. A. et al., *Invest Ophthalmol Vis Sci* 50:462-9 (2009)). Here we find that the expression levels of EMP2 in the RPE cells causing the PVR correlates with the severity of PVR in the rabbits. Independent evidence for the relevance of EMP2 in PVR was obtained using a blocking antibody against EMP2 which, in contrast to the control antibody, decreased PVR severity.

Example 2

Proliferative vitreoretinopathy (PVR) is an aberrant wound healing that occurs as a complication of severe ocular trauma including penetrating injuries or rhegmatagenous retinal detachments. Epithelial membrane protein 2 (EMP2) regulates collagen gel contraction by the retinal pigment epithelium cell line ARPE-19, an in vitro model for PVR, by modulating FAK activation. The purpose of this study is to investigate the efficacy of an EMP2 specific recombinant diabody in blocking collagen gel contraction by ARPE-19 cells.

Methods

EMP2 diabody was recombinantly constructed using a phage library to select for reactivity against a human EMP2 peptide. In all experiments ARPE-19 cells were pretreated with 20 μg/ml of anti-EMP2 or control diabody for 2 hours. Toxicity, adhesion, and migration were assessed respectively through flow cytometry using Annexin V, binding to collagen type 1, and a wound healing assay. Collagen gel contraction was assessed using an in vitro assay.

Results

No toxicity was observed using the anti-EMP2 diabody. The anti-EMP2 diabody did not significantly alter adhesion or migration. Exposure to anti-EMP2 diabody resulted in a 75% reduction in EMP2 protein levels at 4 hours. EMP2 recovery to pre-treatment levels was seen after 16 hours. Concordant decreases in basal levels of activated FAK were also observed. Collagen stimulated FAK activation was reduced by 25% in ARPE-19 cells treated with anti-EMP2 diabody. Anti-EMP2 diabody treatment significantly reduced collagen gel contraction by the ARPE-19 cells (p<0.001) and was dose dependent.

Conclusions

Anti-EMP2 diabody decreases contractile capacity through down regulation of EMP2 leading to decreased FAK activation and inhibition of collagen gel contraction.

Example 3

Introduction

Focal adhesion kinase (FAK) and its activation through phosphorylation is important for cell cycle progression, proliferation, invasion, migration, survival, and contraction (Schaller M D et al., *Proc Natl Acad Sci USA*, 89:5192-5196 (1992)). FAK phosphorylation can be initiated by integrin receptor ligation to extracellular matrix components. In addition, a number of non-integrin signaling pathways promote FAK activation, including EGF and PDGF ligation through receptor tyrosine kinase signaling, and ligation of receptors for lysophosphatidic acid (LPA), bombesin, and sphingosylphosphorylcholine (SPC) through G-protein linked receptors (Rankin S and Rozengurt E, *J Biol Chem*, 269:704-710 (1994); Seufferlein T and Rozengurt E, *J Biol Chem*, 269:9345-9351 (1994); Seufferlein T and Rozengurt E, *J Biol Chem*, 270:24334-24342 (1995); Sieg D J et al., *Nat Cell Biol*, 2:249-256 (2000); Sinnett-Smith J et al., *J Biol Chem*, 268:14261-14268 (1993)). FAK activation is a complex process requiring phosphorylation at multiple sites. Phosphorylation occurs at Tyr-397 and Tyr-407 (N-terminal domain), Tyr-576 and Tyr-577 (kinase domain activation loop), and Tyr-861 and Tyr-925 (C-terminal domain). The initial step in FAK activation is autophosphorylation at Tyr-397, creating a binding site for the SH2 domain of Src tyrosine kinase, resulting in the activation of the Src kinase domain. The remaining FAK tyrosine phosphorylation sites are preferentially phosphorylated by Src (Calalb M B et al., *Mol Cell Biol*, 15:954-963 (1995); Schlaepfer D D et al., *Prog Biophys Mol Biol*, 71:435-478 (1999); Schlaepfer D D and Hunter T, *Trends Cell Biol*, 8:151-157 (1998)). Phosphorylation of FAK Tyr-576 and Tyr-577 in the activation loop of the kinase domain is required for maximal FAK kinase activity (Calalb M B et al., *Mol Cell Biol*, 15:954-963 (1995); Mitra S K and Schlaepfer D D, *Curr Opin Cell Biol*, 18:516-523 (2006)), and phosphorylation of FAK Tyr-925 creates a SH2 binding site for the Grb2 small adaptor protein (Schlaepfer D D et al., *Nature*, 372:786-791 (1994)). Grb2 binding to FAK is one of several signaling pathways leading to the activation of downstream targets such as the ERK2/MAP kinase cascade. Phosphorylation at Tyr-407 and Tyr-861 has been implicated in epithelial-mesenchymal transdifferentiation (EMT) (Nakatnoto T et al., *Mol Cell Biol*, 17:3884-3897 (1997)). FAK phosphorylation at Tyr-861 has also been implicated in F-actin organization (Lunn J A et al., *J Biol Chem*, 282:10370-10379 (2007)).

Epithelial membrane protein 2 (EMP2) is a tetraspan (4-transmembrane) protein belonging to the growth arrest specific-3/peripheral myelin protein-22 (GAS3/PMP22) family. EMP2 is localized to the skin, lung, uterus, heart, thyroid, and eye (Wang C X et al., *Blood*, 97:3890-3895 (2001)). In the eye, EMP2 is present in multiple epithelial layers including the cornea, ciliary body, and retinal pigment epithelium (RPE) (Wadehra M et al., *Exp Mol Pathol*, 74:106-112 (2003)). EMP2 has been shown to regulate trafficking of integrins, glycosylphosphatidyl inositol-anchored proteins, and MHC class I proteins (Wadehra M et al., *Dev Biol*, 287:336-345 (2005); Wadehra M et al., *Mol Biol Cell*, 15:2073-2083 (2004); Wadehra M et al., *J Biol Chem*, 277:41094-41100 (2002); Wadehra M et al., *Clin Immunol*, 107:129-136 (2003)). EMP2 is physically associated with, and modulates function of certain integrin isoforms in physiologic settings such as blastocyst implantation, and in model settings of cellular proliferation, invasion, adhesion, and metastasis (Wadehra M et al., *Exp Mol Pathol*, 74:106-112 (2003); Wadehra M et al., *Dev Biol*, 287:336-345 (2005); Wadehra M et al., *Mol Biol Cell*, 15:2073-2083 (2004); Wadehra M et al., *J Biol Chem*, 277:41094-41100 (2002); Wadehra M et al., *Clin Immunol*, 107:129-136 (2003); Wadehra M et al., *Dev Biol*, 292:430-441 (2006)).

The biochemical mechanisms involved in EMP2 function are uncertain. However, in other tetraspan proteins a prominent theme is multimeric association with heterologous tetraspans and other membrane proteins involved in signaling pathways (Boucheix C et al., *Cell Mol Life Sci*, 58:1189-1205 (2001); Hemler M E, *J Cell Biol*, 155:1103-1107 (2001)). This suggests that tetraspan proteins act as molecular adaptors supporting the functional assembly of signaling complexes in the membrane (Hong I K et al., *J Biol Chem*, 281:24279-24292 (2006)). Perhaps best defined is a subset of tetraspan proteins shown to recruit PI-4 kinase to specific membrane locations and induce phosphoinositide-dependent signaling (Yauch R L and Hemler M E, *Biochem J*, 351 Pt 3:629-637 (2000)).

EMP2 is known to increase collagen gel contraction of the ARPE-19 cell line through FAK activation measured by phosphorylation at Tyr-576 and 577 (Morales S A et al., *Invest Ophthalmol Vis Sci*, 9:9 (2008)). The purpose of this study was to further explore the relationship of EMP2 and FAK activation. Here we show that EMP2 physically associates with FAK, leading to increased phosphorylation of FAK at multiple sites. This increased phosphorylation of FAK results in functional mechanical cellular alterations leading to an increased cellular contractile capacity. These cellular alterations include increased focal adhesion density, conformational changes in the actin cytoskeleton, actin composition alterations, and increased cellular adhesive capacity. These findings suggest that EMP2 may represent a new role for tetraspans in the functional assembly of membrane signaling complexes important for activation of FAK.

Methods

Cell Line—

ARPE-19, a spontaneously arising retinal pigment epithelial (RPE) cell line which expresses the RPE-specific markers CRALBP and RPE-65, was obtained from the American Type Culture Collection (CRL-2302, ATCC, Manassas, Va.). ARPE-19/EMP2, an EMP2 overexpressing cell line, was produced through stable infection of an EMP2 over expressing retrovirus construct, expressing 75-fold elevated protein level of EMP2 (Morales S A et al., *Invest Ophthalmol Vis Sci*, 9:9 (2008)). ARPE-19 cells were cultured in DMEM-F12 medium, supplemented with 10% fetal bovine serum (FBS) (ATCC, Manassas, Va.) at 37° C. in a humidified chamber with 5% $CO_2$. For all experiments cells were plated and incubated overnight. All cells were about 75% confluent at the initiation of each experiment, unless otherwise noted.

Antibodies—

All antibodies for human FAK were obtained from Santa Cruz Biotechnology (Santa Cruz, Calif.): goat antibody for phosphorylated FAK (p-FAK) (clone Tyr 576/577), and rabbit antibodies for FAK (clone C-20), p-FAK (Tyr 397), (Tyr 407), (Tyr 861), and (Tyr 925). Rabbit antibodies for human p-Src (Tyr 416 and Tyr 527) were from Cell Signaling Technology (Danvers, Mass.). A mouse antibody recognizing human β-actin (clone 2A2.1) was from US Biological (Swampscott, Mass.). A mouse antibody against human α-smooth muscle actin (α-sma) (clone 1A4) was from Sigma (St. Louis, Mo.). Texas Red-X phalloidin (T7471), used to identify F-actin, was from Invitrogen (Carlsbad, Ca). Rabbit antisera against human EMP2 was produced following immunization of animals with a multiple antigen peptide conjugated to the second extracellular loop of human EMP2 (EDIHDKNAKFYPVTREGSYG) (SEQ ID NO: 2) (Research Genetics, Huntsville, Ala.). Horseradish peroxidase-conjugated goat anti-rabbit antibody was obtained from Southern Biotech (Birmingham, Ala.). Horseradish peroxidase-conjugated goat anti-mouse was obtained from BD Biosciences (San Diego, Calif.). Texas Red-conjugated donkey anti-goat (705-075-147) and FITC-conjugated donkey anti-rabbit (711-095-152) antibodies were obtained from Jackson ImmunoResearch Laboratories (West Grove, Pa.).

Western Blot Analysis—

Western analysis was performed as previously described (Morales S A et al., *Experimental Eye Research* (2007)). Briefly, cell protein was isolated using RIPA buffer containing protease and phosphatase inhibitors (Upstate, Charlottesville, Va.) and the protein concentration determined with BCA Protein Assay (Bio Rad, Hercules, Calif.). For EMP2 detection, N-linked glycans were cleaved using PNgase (New England Biolaobs, Beverly, Mass.). Lysates were treated per manufacturer's instructions at 37° C. for 2 hours. A total of 10 μg of protein was loaded in each lane and the proteins fractionated by 4-20% SDS-PAGE gradient gel under reducing conditions. Proteins were transferred to nitrocellulose membranes (Amersham Life Sciences, Buckinghamshire, UK) and the adequacy of transfer confirmed using Ponceau S red staining (Sigma Chemical Co., St. Louis, Mo.).

The membrane was blocked with nonfat milk in TBS Tween (TBST; Upstate, Charlottesville, Va.). Blots were incubated for 1 hour with primary antibody at a dilution of 1:200 for α-sma, FAK and p-FAK (Tyr 576/577), (Tyr 397), (Tyr 407), (Tyr 861), (Tyr 925), 1:1000 for EMP2 and p-Src (Tyr 416), (Tyr 527), and 1:5000 for β-actin. Horseradish peroxidase-conjugated goat anti-rabbit or horseradish peroxidase-conjugated goat anti-mouse was exposed to the blots at a 1:2000 dilution. Blots were developed with ECL (Pierce, Rockford, Ill.) and quantified, by scanning the blots and measuring band density with NIH Image J software. The intensity of either the β-actin or total FAK band was used as an internal control and all bands were analyzed in a linear range for measurement of density by quantification. At least three independent experiments were performed, and were statically evaluated using a Student's t-test (unpaired, one-tail); $p<0.05$ was considered statistically significant. Co-Immunoprecipitation—ARPE 19 and ARPE-19/EMP2 cells were plated in 10 cm dishes (Corning, Corning, N.Y.). Cells were washed 2 times with PBS, lysed (1% Nonidet P-40 containing 10 μg/ml aprotinin, 2 μg/ml pepstatin, 0.1 mM EDTA, 10 mM HEPES, and 10 mM KCl, with Complete Mini Protease Inhibitor Cocktail Tablet from Roche Applied Sciences, Mannheim, Germany) for 30 minutes at 4° C., and then sonicated for 15 seconds. Cell lysates were precleared by incubation with Protein A agarose beads (Santa Cruz Biotechnology, Santa Cruz, Calif.), and then incubated overnight with agarose beads and either anti-FAK polyclonal antibody (Santa Cruz Biotechnology, Santa Cruz, Calif.) or anti-EMP2 rabbit polyclonal antibody. The beads were washed 4 times in the lysis solution, and twice in 62.5 mM Tris, pH 6.8. Immune complexes were eluted from the beads by boiling in Laemmli sample buffer (62.5 mM Tris-Cl, pH 6.8, 10% glycerol, 2% SDS, 0.01% Bromophenol blue, 2% β-mercaptoethanol) for 5 minutes. Samples were analyzed using western blot analysis. For EMP2 detection, N-linked glycans were cleaved using PNgase (New England Bioloabs, Beverly, Mass.). Eluates were treated as per manufacturer's instructions at 37° C. for 2 hours.

The stoichiometry of FAK and EMP2 in coimmunoprecipitation experiments was determined in the following manner. First, titrations of whole cell lysate and cognate immunoprecipitates were quantitated by densitometry. Using this data, we calculated the percent of each protein (per input cell equivalents) in the cognate immunoprecipitate. Second, the co-immunoprecipitates were similarly analyzed, to determine the percent of each protein captured in the co-immunoprecipitate. Finally, we calculated the ratio of these two values (percent cognate and percent co-immunoprecipitate), representing the stoichiometry of the co-immunoprecipitated proteins.

Immunofluorescence—

ARPE-19 and ARPE-19/EMP2 cells were plated overnight onto glass coverslips (Fisher). Cells were fixed with 4% paraformaldehyde for 20 minutes and permeabilized with 0.075% Saponin for 15 minutes. The cells were blocked with 10% normal donkey serum for 30 minutes. Cells were incubated overnight at 4° C. in a humidified chamber with the primary antibody and then washed 3-4 times with PBS plus 0.01% Triton X-100 (PBST). Cells were incubated for 1 hour with fluorescein isothiocyanate (FITC)-conjugated donkey anti-rabbit IgG and Texas Red-conjugated donkey anti-goat at room temperature in a humidified chamber. Cells were washed with PBST, rinsed briefly with double-distilled $H_2O$, and mounted onto microscope slides using VECTASHIELD Mounting Medium (Vector Laboratories, Burlingame, Calif.).

Zeiss LSM 510 laser scanning confocal microscope (Thornwood, N.Y.) was used to assess the distribution and colocalization of proteins. To detect FITC-labeled and Texas Red-labeled cells, samples were excited with argon and krypton lasers at 488 and 568 nm, respectively. LSM software was used for controlling the microscope, scanning and laser modules, image recording, and the analysis of image data.

Colocalization analysis was preformed using LSM software to generate percent association. Highlighted pixels were determined using Image J (NIH software). At least 6 fields were randomly chosen for analysis for each sample and percent association is an average value generated from the multiple fields. Multiple slices per field were evaluated but only a single slice of the bottom surface of the cell, which contacts the slide and contains focal adhesions, was used for quantifying the colocalization of the focal adhesions with EMP2. In all experiments, cells were observed using a 60× oil immersion objective. Each experiment was repeated at least four times.

Adhesion Assay—

ARPE-19 and ARPE-19/EMP2 cells were plated onto either a 24-well collagen coated plate (BD Biosciences, San Diego, Calif.) or a CytoMatrix Screening plate precoated with fibronectin, vitronectin, collagen I, and collagen IV (Millipore, Billerica, Mass.) at a concentration of $2\times10^5$ cells per well. The cells were incubated at 37° C. in a humidified chamber with 5% CO2 for 2 hours. The plate was then washed 3 times with PBS to remove any unattached cells. Bound cells were analyzed for crystal violet uptake and, following solubilization, absorbance was measured at 595 nm by a Bio-Rad microplate reader 550 (Hercules, Calif.). Each experiment included at least eight replicates, and at least three independent experiments were performed with comparable results. A Student's t-test (unpaired, one-tail) was used and a $P<0.05$ was judged to be statistically significant.

Results

Relationship of p-FAK and EMP2 in ARPE-19 Cells.

Figure 7:
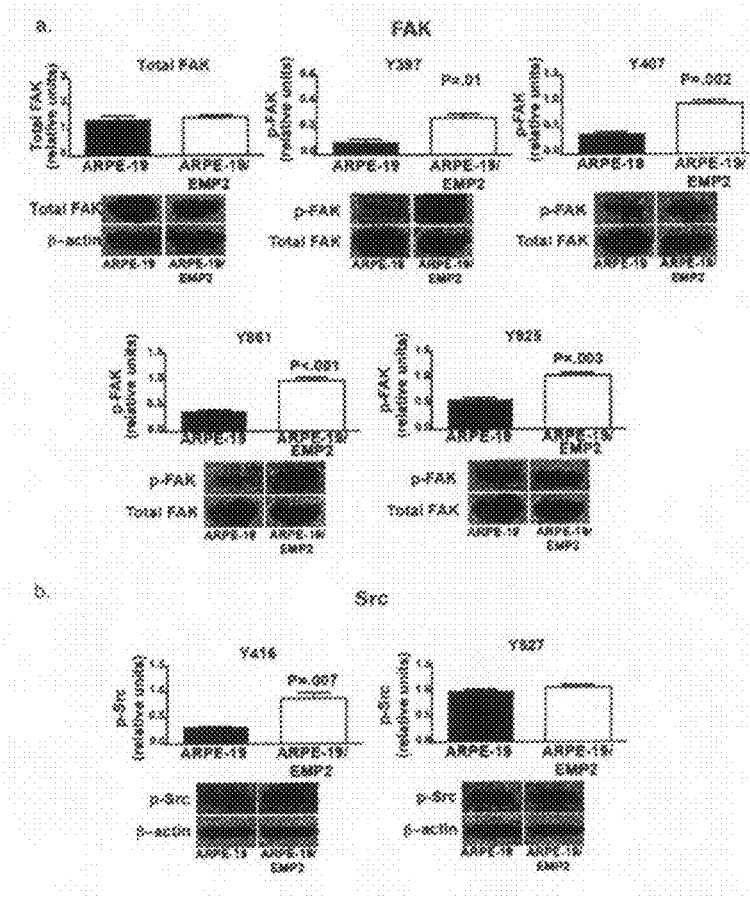
FIG. 7. A. Effect of EMP2 on FAK phosphorylation. Levels of total FAK, p-FAK (Y397, Y407, Y861, and Y925), and β-actin were measured by Western blot in the cell lines ARPE-19 and ARPE-19/EMP2, and quantified by densitometry. B. p-Src (Tyr 416 and Tyr 527), and β-actin were treasured by Western blot in the cell lines ARPE-19 and ARPE-19/EMP2, and quantified by densitometry. Phosphorylation level (mean±S.E.M.) at each site was normalized to total FAK (A) or β-actin (B), and calculated from at least three independent experiments. Representative Western blots are also shown.

FAK phosphorylation, elaborated through Src interaction and mutual phosphorylation events, recruits signaling and adapter proteins that drive a diverse array of cellular responses (Jacamo R O and Rozengurt E., *Biochem Biophys Res Commun,* 334:1299-1304 (2005)). We previously investigated whether EMP2 overexpression in the ARPE-19 cells led to alteration in FAK/Src activity. We showed that total FAK levels were equivalent in both the ARPE-19 and ARPE-19/EMP2 cells (Morales S A et al., *Invest Ophthalmol Vis Sci,* 9:9 (2008)) and confirmed in FIG. 7, however, overexpressing EMP2 demonstrated an almost two-fold increase in the level of activated FAK (Tyr-576/577) as compared to the control ARPE-19 cells. Multiple evaluations, in which each activated FAK was normalized to its own β-actin loading control, showed a statistically significant correlation between increased EMP2 levels and FAK activation (Morales S A et al., *Invest Ophthalmol Vis Sci,* 9:9 (2008)). Other sites of FAK phosphorylation were investigated in the ARPE-19 and ARPE-19/EMP2 cells by quantitative Western blot and normalized to total FAK (FIG. 7A). EMP2 overexpression enhanced phosphorylation of FAK two- to three-fold at Tyr-397, Tyr-407, Tyr-861, and Tyr-925.

Src enzymatic activity is reciprocally regulated by tyrosine phosphorylation at Tyr-416 (augmenting) and Tyr-527 (suppressing) (Harvey R et al., *Mol Cell Biol,* 9:3647-3656 (1989)). Compared to control cells, overexpression of EMP2 was associated with increased Src phosphorylation at Tyr-416 (FIG. 7B). This result was predicted as this activation of the Src kinase domain is associated with phosphorylation of FAK at Tyr-397. Importantly, there was no change in phosphorylation levels at Src Tyr-527, which is not in the kinase domain (FIG. 7B). Taken together, these findings indicate that elevated EMP2 resulted in phosphorylation changes of FAK and Src known to increase mechanical contractility.

EMP2 Physically Associates with FAK.

EMP2 expression is required for efficient integrin-mediated cellular responses, and EMP2 physically associates with certain integrin isoforms (Wadehra M et al., *Dev Biol*, 287:336-345 (2005); Wadehra M et al., *Mol Biol Cell*, 15:2073-2083 (2004); Wadehra Metal., *J Biol Chem*, 277: 41094-41100 (2002); Wadehra M et al., *Clin Immunol*, 107:129-136 (2003)). FAK is an important signaling partner of integrins, a role that includes the physical association of β1 integrin cytoplasmic tail and the N-terminal domain of FAK in vitro (Lyman S et al., *J Biol Chem*, 272:22538-22547 (1997); Schaller M D et al., *J Cell Biol*, 130:1181-1187 (1995)). Therefore, we hypothesized that the positive effect of EMP2 levels on FAK phosphorylation might reflect a physical association between FAK with EMP2. To address to this issue we examined two requirements of physical association, binding either directly or indirectly via immunoprecipitation and localization within the same cellular space via confocal microscopy.

We first evaluated this idea by testing whether EMP2 and FAK are physically associated (FIG. 8A). Immunoprecipitates using an antibody against EMP2 includes readily detectable FAK in both ARPE-19 and ARPE-19/EMP2 cells. To determine the stoichiometry of the association, we used three independent experiments to tabulate quantitated levels of EMP2 and FAK in the immunoprecipitates. First, titrations of whole cell lysate and cognate immunoprecipitates were quantitated by densitometry. Using this data, we calculated the percent of each protein (per input cell equivalents) in the cognate immunoprecipitate. Second, the co-immunoprecipitates were similarly analyzed, to determine the percent of each protein captured in the co-immunoprecipitate. Finally, we calculated the ratio of these two values (percent cognate and percent co-immunoprecipitate), representing the stoichiometry of the co immunoprecipitated proteins. Cognate immunoprecipitation of FAK (FIG. 8A) and EMP2 (data not shown) were comparably efficient (50-60%). The level of FAK in the EMP2 immunoprecipitates was 12% and 15% in ARPE-19 and ARPE-19/EMP2, respectively and calculated that 24% to 30% of total FAK was associated with EMP2 in these two cell lines, respectively.

To evaluate whether EMP2 and FAK localize within the same cellular space, their colocalization in situ was examined by confocal microscopy. Multiple levels per field were evaluated but only a single slice of the bottom surface of the cell, which contacts the slide and contains focal adhesions, was used for quantification. EMP2 (green) and FAK (red) were detected by immunofluorescence, and visualized by confocal microscopy (FIG. 8B). The merge of these two channels is shown, as well as a merge in which highlighted co-localized pixels are displayed as white signal (right). By inspection, EMP2 and FAK were prominently co-localized in both cell types. By pixel quantitation of three independent experiments, 68%±9% and 96%±1% of FAK present at the cell surface contacting the glass slide was colocalized with EMP2 in ARPE-19 and ARPE-19/EMP2 cells respectively. Total FAK levels demonstrated a slight, but not significant increase in the ARPE-19/EMP2 cell line (FIG. 7A). This confirms our previously published data demonstrating that EMP2 levels do not affect Total FAK protein expression (Morales S A et al., *Invest Ophthalmol Vis Sci*, 9:9 (2008)).

To examine whether EMP2 associates with phosphorylated FAK, cells were stained with EMP2 and p576/577-FAK primary antibodies. Multiple slices per field were evaluated but only a single slice of the bottom surface of the cell, which contacts the slide and contains focal adhesions, was used for quantification. EMP2 is detected with FITC, and phosphorylated FAK is detected with Texas Red (FIG. 8C). In ARPE-19, 31%±8% of p-FAK (Y576/577) is co-localized with EMP2. There is a central area within the cells that show co-localization, however identification of this subcellular region would require additional studies. In the ARPE-19/EMP2, 97%±0.4% of p-FAK (Y576/577) is co-localized with EMP2 at this level. EMP2 and FAK (total and p-FAK (Y576/577) are highly co-localized in situ, and elevated EMP2 increases the degree of colocalization. However, given the degree that EMP2 is overexpressed, this may not imply specific enrichment of FAK.

Increased EMP2 Levels Resulted in Altered Distribution of Phosphorylated FAK.

Figure 9:
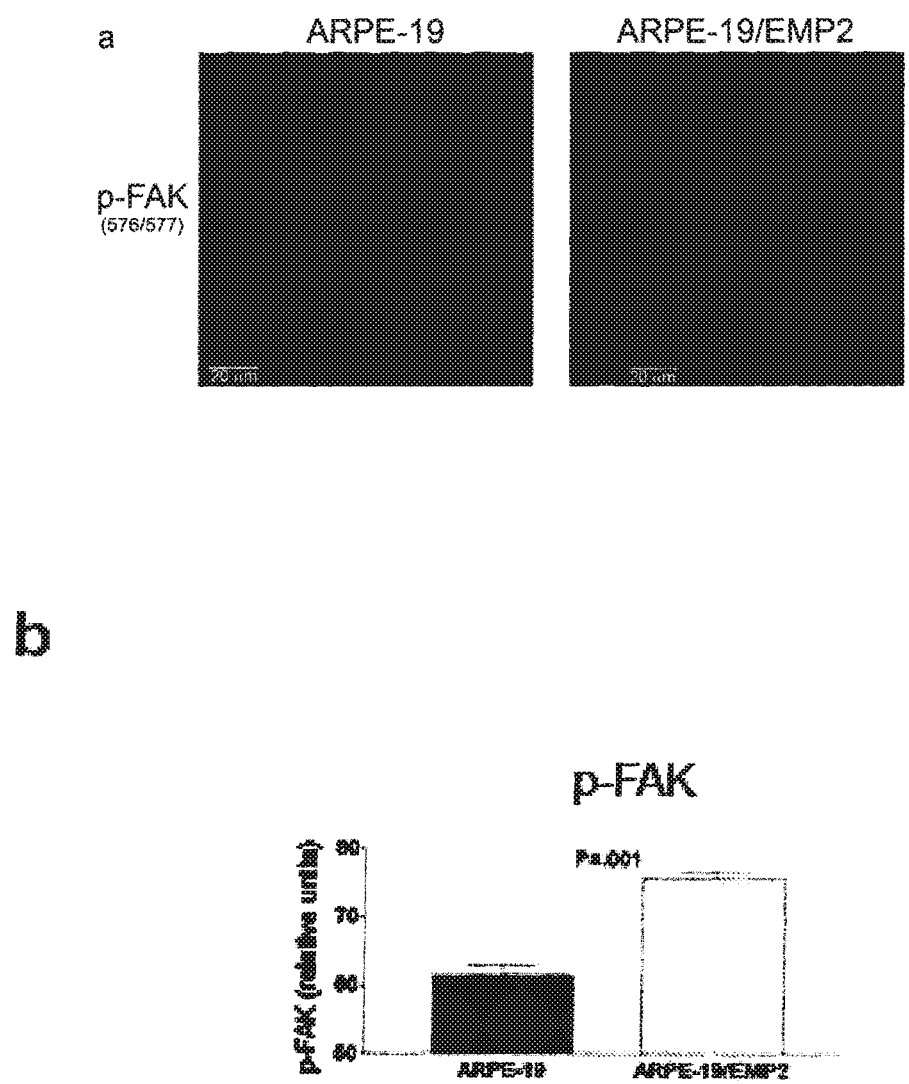
FIG. 9. Modulating EMP2 expression affects FAK phosphorylation and localization. ARPE-19 and ARPE-19/EMP2 cells were stained with p576/577-FAK (A) primary antibody. Cells were incubated with a Texas Red-conjugated donkey anti-goat antibody and observed under fluorescence microscopy. Phosphorylated FAK (B) from at least four separate samples were quantified by calculating pixel intensity (see Methods), and the data was evaluated by a Student's t-test (unpaired, one-tail).

ARPE-19 and ARPE-19/EMP2 (FIG. 9A) cells were stained for phosphorylated FAK (Y576/577) protein. Increased EMP2 levels resulted in altered distribution of phosphorylated FAK. In the ARPE-19 cells, phosphorylated FAK was found mainly on the periphery of the cell (FIG. 9A), while in the ARPE-19/EMP2 cells phosphorylated FAK is found distributed throughout the cell (FIG. 9A). Pixel intensity from at least four separate samples was measured; by student's t-test (unpaired, one-tail), this evaluation, concordant with our prior report using Western blot for protein detection (Morales S A et al., *Invest Ophthalmol Vis Sci*, 9:9 (2008)) also demonstrated a significant increase in phosphorylated FAK in the ARPE-19/EMP2 cells (FIG. 9B).

Increased EMP2 and Phosphorylated FAK Expression Leads to Altered F-Actin Distribution.

Figure 10:
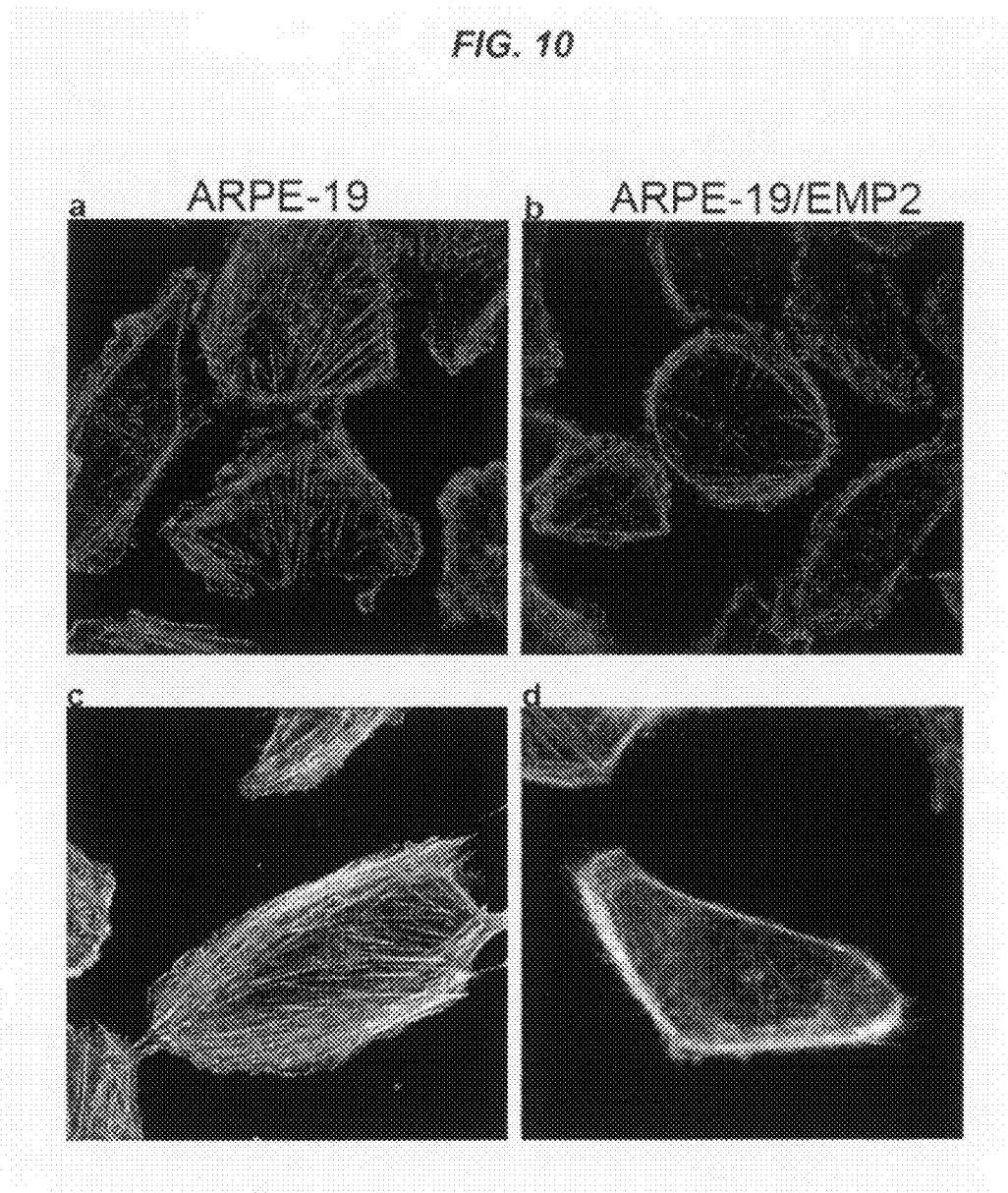
FIG. 10. Increased EMP2 and phosphorylated FAK expression leads to altered F-actin distribution. ARPE-19 (A and C) and ARPE-19/EMP2 (B and D) cells were plated overnight onto glass coverslips. Cells were fixed with paraformaldehyde, permeabilized with saponin, and stained with Texas Red-X phalloidin. A representative picture is shown in color (A and B) and in black and white (C and D).

Increased EMP2 expression leads to increased FAK phosphorylation at multiple sites, including Tyr-861, which has been associated with F-actin organization. Accordingly, we examined whether there was a concomitant change in observable actin organization in association with increased EMP2 expression. ARPE-19 (FIG. 10A,C) and ARPE-19/EMP2 (FIG. 10B,D) cells were stained with Texas Red-X phalloidin primary antibody. Increasing EMP2 expression resulted in altered F-actin expression. F-actin was expressed along the periphery of the cell in the ARPE-19/EMPs cells whereas F-actin was expressed throughout the cell in ARPE-19 cells. We chose to examine actin fibers in actively growing cells, similar to those tested in the gel contraction assay. Additional studies could be done in the future looking at the arrangement in confluent cells.

Increased EMP2 Expression Resulted in Increased α-Smooth Muscle Actin Expression.

Increased EMP2 expression leads to increased FAK phosphorylation at Tyr-861 as well as Tyr-407, which have both been implicated as important sites in cellular EMT. A marker for EMT is the expression of α-sma. Levels of α-sma were measured by western blot analysis in ARPE-19 and ARPE-19/EMP2 cells in order to test whether increased EMP2 expression with its associated FAK phosphorylation has a functional effect on α-sma expression (FIG. 11A). Blots were then developed with ECL to visualize bound antibody and quantified using β-actin as an internal control (FIG. 11B). Increased EMP2 expression led to a significant increase in α-sma expression.

Increased EMP2 Levels Leads to Increased Cellular Adhesion to Collagen Types I and IV.

Figure 12:
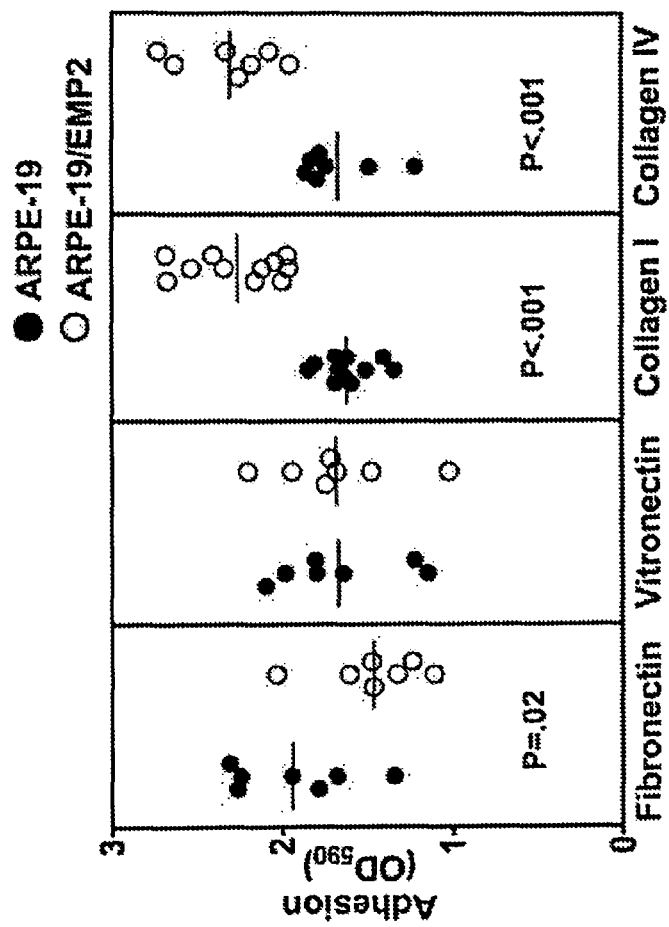
FIG. 12. Increased EMP2 levels leads to increased adhesion to collagen. ARPE-19 and ARPE-19/EMP2 cells were plated on plates coated with fibronectin, vitronectin, collagen I, and collagen IV. Bound cells were analyzed by crystal violet uptake and a quantitative evaluation of absorbance was measured by a microplate reader (at 590 nm). Increasing EMP2 expression resulted in increased adhesion to collagen I (P<0.001) and collagen IV (P<0.001). Adhesion to fibronectin was increased (P=0.02) in ARPE-19 cells as compared to ARPE-19/EMP2 cells. Altering EMP2 levels did not affect adhesion to vitronectin. The results are presented from one experiment with at least eight replicates, and at least three independent experiments were performed with comparable results. A Student's t-test (unpaired, one-tail) was used for statistical analysis.

ARPE-19/EMP2 cells showed a greater distribution of phosphorylated FAK throughout the cell as compared to AR-PE-19 cells. We hypothesized that the increased distribution of phosphorylated FAK represented functional focal adhesions, which would confer greater adhesive capacity to the ARPE-19/EMP2 cells. To test this hypothesis we plated ARPE-19 and ARPE-19/EMP2 cells onto plates precoated with fibronectin, vitronectin, collagen I, and collagen IV. Bound cells were analyzed for crystal violet uptake and by a Bio-Rad microplate reader 550. Increasing EMP2 expression resulted in a specific increase in the attachment phase of adhesion to collagen type I and N (P<0.001), deceased in attachment to fibronectin (P<0.02), and no affect in attachment to vitronectin and (FIG. 12).

Discussion

This study was guided by the hypothesis that EMP2, like other tetraspan family members (Hong I K et al., *J Biol Chem*, 281:24279-24292 (2006)), is a molecular adaptor between certain integrin isoforms and their associated signaling modules. Our previous study identified that activation of the FAK-Src pathway is critical in producing contraction of collagen gels in an in vitro model of PVR using the RPE cell line ARPE-19 (Morales S A et al., *Experimental Eye Research* (2007)). Furthermore, our studies demonstrated that EMP2 is able to control collagen gel contraction; through activation of FAK (γ-576/577) (Morales S A et al., *Invest Ophthalmol Vis Sci*, 9:9 (2008)). We previously demonstrated that EMP2 associates with integrin β1 (Wadehra M et al., *J Biol Chem*, 277:41094-41100 (2002)) and other groups have shown that FAK binds in vitro to the integrin β1 subunits (Schlaepfer D D et al., *Prog Biophys Mol Biol*, 71:435-478 (1999); Parsons J T et al., *Oncogene*, 19:5606-5613 (2000)). In this study, we provide evidence that EMP2 enhances FAK activation and physically associates with FAK, with functional downstream consequences affecting focal adhesion density, cellular adhesive capacity, F-actin conformation, and actin composition. Accordingly, EMP2 may act as a molecular adaptor for efficient integrin-mediated FAK activation and its consequences for FAK-associated cellular functions. Although the co-IP and co-localization studies support either a direct or indirect association via the formation of a multi protein complex additional biochemical studies would be required to define the specific details of this relationship.

An important mechanism for FAK activation is integrin receptor mediated clustering of FAK resulting in autophosphorylation, Src recruitment, and FAK phosphorylation at multiple sites. The activated FAK/Src complex subsequently acts as a molecular scaffold for a diverse array of proteins, such as Grb2, p130$^{Cas}$, paxillin, Talin, CAP, Graf, Src, and the p85 subunit of PI3-kinase, and may participate in numerous signaling pathways (Schlaepfer D D et al., *Prog Biophys Mol Biol*, 71:435-478 (1999); Parsons J T et al., *Oncogene*, 19:5606-5613 (2000); Cox B D et al., *J Cell Biochem*, 99:35-52 (2006)).

In this report we demonstrate that EMP2 associates with FAK leading to increased activation of FAK by enhancing focal adhesion formation and hypothesize that EMP2 may act as the molecular adaptor between integrin ligation and FAK activation. We previously examined the role of EMP2 in collagen gel contraction, an in vitro correlate of proliferative vitreoretinopathy (PVR). PVR is a complication following surgical repair of a rhegmatogenous retinal detachment in up to 10% of patients (Charteris D G et al., *Eye*, 16:369-374 (2002); Kirchhof B., *Graefes Arch Clin Exp Ophthalmol*, 242:699-703 (2004); Lewis G P et al., *Eye*, 16:375-387 (2002)). PVR represents the culmination of a complex migration of multiple cell types, including RPE, into the vitreous cavity (Baudouin C et al., *Ophthalmologica*, 203:38-46 (1991); Casaroli-Marano R P et al., *Invest Ophthalmol Vis Sci*, 40:2062-2072 (1999); Charteris D G et al., *Br J Ophthalmol*, 79:953-960 (1995); Vinores S A et al., *Invest Ophthalmol Vis Sci*, 31:2529-2545 (1990)). There is evidence for epithelial to mesenchymal transition (EMT) of RPE cells, resulting in migration, membrane formation, and an aberrant wound-healing strategy associated with contractile cellular forces leading to tractional retinal detachment. Using collagen gel contraction performed by ARPE-19 cells, we identified integrin receptor activation and signaling through FAK as a critically important process required for ARPE-19 mediated contraction (Morales S A et al., *Experimental Eye Research* (2007)). We recently observed that EMP2 expression levels positively correlated with collagen gel contraction, and that this phenotype was achieved through facilitating FAK activation (Morales S A et al., *Invest Ophthalmol Vis Sci*, 9:9 (2008)).

In the context of PVR pathogenesis, EMT is a key component. Phosphorylation of FAK at Tyr-407 and Tyr-861 is identified as important in EMT progression (Nakamura K et al., *Oncogene*, 20:2626-2635 (2001)). Overexpression of EMP2 leads to an increase in Tyr-407 and Tyr-861 phosphorylation and is thus predicted to lead towards EMT progression. One marker for EMT is up regulation of α-sma, which was observed in the EMP2 overexpressing cell line ARP-19/EMP2 cells. These changes in association with increased EMP2 and increased FAK activation are predicted to facilitate a greater contractile phenotype. Organization of F-actin may also affect the capacity of the cells to contract collagen gels. In the ARPE-19 cells, F-actin expression is observed throughout the cell, perhaps conferring a more rigid cellular structure, reducing the cells ability to contract collagen gels. In the ARPE-19/EMP2 cells the F-actin is only found along edges of the cell in a cortical distribution which may confer a more flexible conformation allowing for greater contractile capacity.

Tetraspan proteins have been shown to participate in the formation of a variety of complexes to form the 'tetraspan web' (Levy S and Shoham T, *Physiology (Bethesda)* 20:218-224 (2005); Levy S and Shoham T, *Nat Rev Immunol*, 5:136-148 (2005)), which is the creation of scaffolds and membrane domains that regulate signaling and sorting processes (Levy S and Shoham T, *Physiology (Bethesda)* 20:218-224 (2005); Hemler M E, *Nat Rev Mol Cell Biol*, 6:801-811 (2005)). These complexes can modulate the signaling, trafficking and structural characteristics of their membrane protein constituents. When tetraspans form complexes with integrin molecules they can modulate cell adhesion and mobility (Caplan M I et al., *Curr Opin Nephrol Hypertens*, 16:353-358 (2007)). Our report adds a piece to the tetraspan puzzle, demonstrating that EMP2 regulates FAK activation through a physical association leading towards an EMT phenotype with a greater cellular contractile capacity. The EMP2-FAK association represents a novel protein-protein interaction, not previously reported, that demonstrates significant functional cellular responses in the context of in vitro models of PVR.

Example 4

Introduction

The 4-transmembrane (tetraspan) protein EMP2 is expressed at discrete locations in the eye, lung, heart, thyroid, and uterus. (Wang C X et al., *Blood*, 97(12):3890-3895 (2001)) In the eye, EMP2 is localized to multiple epithelial layers including the cornea, ciliary body, and retinal pigment epithelium (RPE). (Wadehra M et al., *Exp Mol Pathol*, 74(2):106-112 (2003)) In multiple nonocular cell types, EMP2 plays a critical role in selective receptor trafficking, affecting molecules that are important in proliferation, invasion, adhesion, and metastasis. (Wadehra M et al., *Exp Mol Pathol*, 74(2):106-112 (2003); Wadehra M et al., *Dev Biol*, 287(2):336-345 (2005); Wadehra M et al., *Mol Biol Cell*, 15(5):2073-2083 (2004); Wadehra M et al., *J. Biol. Chem.*, 277(43):41094-41100 (2002); Wadehra M et al., *Cancer* 107(1):90-98 (2006); Wadehra M et al., *Clin Immunol*, 107(2):129-136 (2003)) These studies suggest a potential central role for EMP2 in coordinately controlling diverse and important cellular processes in cells of ocular origin.

PVR is observed after rhegmatogenous retinal detachment in up to 10% of patients and is a potentially blinding complication. (Charteris D G et al., *Eye*, 16(4):369-374 (2002); Kirchhof B., *Graefes Arch Clin Exp Ophthalmol*, 242(8):699-703 (2004); Lewis G P et al., *Eye*, 16(4):375-387 (2002)) The pathophysiology underlying PVR is complex and multiple cell types, including RPE, are believed to play a critical role in this disease. (Baudouin C et al., *Ophthalmologica*, 203(1):38-46 (1991); Casaroli-Marano R P et al., *Invest Ophthalmol V is Sci*, 40(9):2062-2072 (1999); Charteris D G., *Br J Ophthalmol*, 79(10):953-960 (1995); Vinores S A et al., *Invest Ophthalmol Vis Sci*, 31(12):2529-2545 (1990)) There is evidence of an epithelial-to-mesenchymal transition resulting in cell migration, membrane formation, and an aberrant wound-healing process associated with contractile cellular forces that may lead to tractional retinal detachment. New strategies for PVR prevention require enhanced understanding of the complex pathophysiology. One in vitro correlate of PVR is collagen gel contraction.

RPE from diverse species have been used in studies of collagen gel contraction, including primary human cells (Hunt R C et al., *Invest Ophthalmol Vis Sci*, 35(3):955-963 (1994)), human ARPE-19 cell (Bando H et al., *Exp Eye Res*, 82(3):529-537 (2006)), bovine (Ando A et al., *Br J Ophthalmol*, 84(11):1306-1311 (2000)), and rabbit (Zheng Y et al., *Invest Ophthalmol Vis Sci*, 45(2):668-674 (2004)). This study was designed to test how EMP2 controls collagen gel contraction through recombinantly altering the expression of EMP2 in the ARPE-19 cell line. Our prior work (Morales S A et al., *Exp Eye Res*, 85(6):790-798 (2007)) and that of others (Bando H et al., *Exp Eye Res*, 82(3):529-537 (2006); Carver W et al., *J Cell Physiol*, 165(2):425-437 (1995); Cooke M E et al., *J Cell Sci*, 113:2375-2383 (2000); Kieffer J D et al., *Biochem Biophys Res Commun*, 217(2):466-474 (1995); Langholz O et al., *J. Cell Biol.*, 131:1903-1915 (1995); Moulin V and Plamondon M., *Br J Dermatol*, 147(5):886-892 (2002); Robbins S G et al., *Invest Ophthalmol Vis Sci*, 35(9):3475-3485 (1994); Zhang Z G et al., *J Cell Sci*, 119:1886-1895 (2006)) identified specific integrin isoforms and found engagement to the collagen matrix to be critically important in collagen gel contraction. We previously identified activation of the FAK/Src pathway as essential in the ARPE-19 cell line in terms of collagen gel contraction in the presence or absence of exogenous proinflammatory stimulation. In the present study, EMP2 expression levels controlled collagen gel contraction, and increasing EMP2 was associated with enhanced FAK activation in the ARPE-19 cell line.

Methods

EMP2 Constructs:

Hammerhead ribozymes were created to cleave the human EMP2 transcripts as previously reported (Wadehra M et al., *Dev Biol*, 287(2):336-345 (2005)). The hRZ2 EMP2 hammerhead ribozyme, which is demonstrated to work well in transfection to reduce EMP2 expression, was used in this study. Briefly, the hRZ2 construct in pEGFP (BD-Clontech, Palo Alto, Calif.) was transfected into ARFE-19 and stable clones were selected (Wadehra M et al., *Dev Biol*, 287(2): 336-345 (2005)).

The full-length cDNA of human EMP2 was cloned into the retroviral vector pMSCV-IRES-GFP at the EcoRI site (Hawley R G et al., *Gene Ther*, 1(2):136-138 (1994)). Expression of EMP2 was driven by the 5' long terminal repeat (LTR). This vector also enables the expression of the green fluorescence protein (GFP) through an internal ribosome entry site. High-titer helper-free retrovirus stocks were prepared by transient cotransfection of 293T cells, as previously described (Pear W., In: Ausubel F M, Brent R, Lingston R E, et al., eds, *Current Protocols in Molecular Biology*, vol. 2. New York: John Wiley & Sons; 9.11-9.15 (1996)).

Cell Lines:

ARPE-19, a spontaneously arising retinal pigment epithelial (RPE) cell line that expresses the RPE-specific markers CRALBP and RPE-65, was obtained from the American Type Culture Collection (CRL-2302; ATCC, Manassas, Va.). ARPE-19 cells were cultured in DMEM-F12 medium, supplemented with 10% fetal bovine serum (FBS; ATCC) at 37° C. in a humidified chamber with 5% $CO_2$. The culture medium was replaced twice a week. After confluence, the cultures were passaged by dissociation in 0.05% (wt/vol) trypsin. Levels of EMP2 were increased in AFPE-19 cells through stable infection of an EMP-2-overexpressing retrovirus construct and selected by flow sorting of GFP-positive cells. These cells, stably infected to increase EMP2 expression are termed ARPE-19/EMP2. EMP2 levels were decreased by stable transfection of the ARPE-19 cells with 3.4 µg of pEGFP-hRZ2 ribozyme construct and transfection reagent (FuGENE 6; Roche, Basel, Switzerland). ARPE-19/Ribo cells were flow sorted for GFP-positive cells. Notably, the transfection reagent did not produce detectable toxicity to the ARPE-19 cells, as determined by trypan blue exclusion (data not shown).

EMP2 levels were decreased by transiently transfecting ARPE-19 cells with 75 picomoles EMP2 siRNA (L-016226-00; Dharmacon, Lafayette, Colo.) and lipophilic transfection reagent (Lipofectamine 2000; Invitrogen, Carlsbad, Calif.) and analyzed after 48 hours. As a negative control, the cells were transfected with 75 picomoles of scramble control siRNA (D-001206-13-05; Dharmacon). The EMP2 siRNA and control siRNA are a pool of four siRNAs targeting EMP2 or a pool of four nontargeting siRNAs, respectively. The level of EMP2 expression was quantified by Western blot.

Antibodies:

Monoclonal antibodies (mAbs) specific for human α1 (clone SR84), α2 (clone AK-7), and α3 (clone C3 II.1) Integrin isoforms were obtained from BD Biosciences (San Diego, Calif.). Rabbit antisera against human EMP2 was produced after immunization of animals with a multiple antigen peptide conjugated to the second extracellular loop of human EMP2 (EDIHDKNAKFYPVTREGSYG) (SEQ ID NO: 2) (Research Genetics, Huntsville, Ala.) (Wadehra M et al., *Exp Mol Pathol*, 74(2):106-112 (2003)). A rabbit antibody specific for human FAK (clone C-20) and pFAK (clone Tyr 576/577) was obtained from Santa Cruz Biotechnology (Santa Cruz, Calif.). A mouse antibody specific for human β-actin (clone 2A2.1) was obtained from US Biological (Swampscott, Mass.). Horseradish peroxidase-conjugated goat anti-rabbit antibody was purchased from Southern Biotech (Birmingham, Ala.). Horseradish peroxidase-conjugated goat anti-mouse and R-PE-conjugated antibodies specific for mouse IgG were from BD Biosciences.

Flow Cytometry:

The membrane expression of α1, α2, and α3 integrin subunits was assessed by flow cytometry. The cells were fixed, but not permeabilized, using 2% paraformaldehyde (wt/vol) in PBS for 20 minutes on ice and then incubated with primary antibody for 30 minutes on ice in PBS+2% FCS. They were washed two times and incubated with R-PE-conjugated anti-mouse IgG antibody for 30 minutes on ice (BD Biosciences). R-PE was used at 0.25 µg/million cells. As a negative control, cells were incubated with isotype control antibody alone. After two consecutive washes, cells were resuspended in PBS and analyzed with flow cytometry (FACScan; BD Biosciences). Integrin expression levels, calculated as mean fluorescent intensity (MFI), which is a reflection of expression in the population of cells, were determined in multiple independent experiments.

Collagen Gel Contraction:

Collagen gel contraction assays were performed as previously reported (Morales S A et al., *Exp Eye Res,* 85(6): 790-798 (2007)). Briefly, collagen gels were prepared by combining collagen type I (BD Biosciences) 10×DMEM, and DMEM/F12. The final concentration of the collagen type I mixture was 2.5 mg/mL. The collagen solution (500 µL) was added to each well of a 24-well plate and incubated at 37° C. in 5% $CO_2$ for 1 hour. Cultured ARPE-19 cell with modified EMP2 levels were harvested and resuspended in serum-free DMEM/F12 at a final concentration of $5 \times 10^5$/mL. ARPE-19 cells with modified EMP2 levels were seeded onto the collagen gel at a concentration of $2.5 \times 10^5$ cells per well and the percentage of contraction was measured at 24 hours. The area of the each gel was obtained by taking a picture of the gel using image capture (Gel Doc 2000; Bio-Rad, Hercules, Calif.) and quantified with NIH Image J (developed by Wayne Rasband, National Institutes of Health, Bethesda, Md.; available at http://rsb.info.nih.gov/ij/index.html). To measure the area of the gel, we used the oval measuring tool to outline each gel. The area of the gel at time 0 was compared to the area of the gel after 24 hours, generating a percentage of contraction for each sample. Each experiment included at least six replicates, and at least three independent experiments were performed with comparable results. A Student's t-test (unpaired, one-tail) was used; $P<0.05$ was judged to be statistically significant.

Proliferation Assay:

Cells were seeded on a 96-well plate and incubated overnight. The medium was removed and then replaced with either normal medium or medium that contained 25 mg/mL collagen I. The cells were then incubated for 48 hours, and proliferation was assessed by BrdU incorporation, as measured by BrdU cell proliferation assay from Calbiochem (San Diego, Calif.), which is a nonisotopic colorimetric immunoassay. The reaction product was quantified with a microplate reader (model 550; Bio-Rad) at a wavelength of 595 nm.

Migration Assay:

ARPE-19 and ARPE-19/EMP2 cells were seeded onto a 24-well plate and incubated for 3 days until cells reached confluence. The cells were washed with PBS, serum-free medium was added, and the cells were incubated overnight. A 10 µL pipette tip was used to make a scratch in the monolayer and the medium was removed and replaced with serum-free medium or serum-free medium that contained 50 ng/mL PDGF. Pictures of the wound were taken at various time points, and the percentage closure of the scratch was quantified with NIH Image J software. The area of the scratch was measured immediately after the wound was created. Over time, cells migrated into the cleared area; however, a gap was still visible after 24 hours. The gap size was measured and divided by the original scratch size, and this value was expressed as percentage closure.

Invasion Assay:

A cell invasion assay (QCM Collagen Cell Invasion Assay; Chemicon, Temecula, Calif.) was used for all invasion assays performed. ARPE-19 and ARPE-19/EMP2 cells were seeded on an invasion chamber insert containing an 8-µm pore size polycarbonate membrane coated with a thin layer of polymerized collagen. Cells that invade and migrate through the polymerized collagen layer cling to the bottom of the polycarbonate membrane. Invading cells on the bottom of the insert membrane are identified colorimetrically and quantitatively analyzed using detection at 560 nm with a microplate reader (model 550; Bio-Rad).

Collagen Productions:

ARPE-19 and ARPE-19/EMP2 cells were seeded onto a six-well plate at a concentration of $7 \times 10^5$ cells/mL in serum-free medium in the presence or absence of 10 ng/mL TCP-β. The medium was collected after 72 hours. Secreted collagen was measured (Sircol Collagen Assay; Accurate Chemical & Scientific, Westbury, N.Y.). The collagen assay is a colorimetric procedure. The reaction product was quantified with the microplate reader at a wavelength of 540 nm. Each experiment included at least six replicates, and at least three independent experiments were performed. A Student's t-test (unpaired, one-tail) was used. $P<0.05$ was judged to be statistically significant.

FAK/Src Inhibition:

Collagen gels were prepared with collagen type I (BD Biosciences) in DMEM/F12 at a final concentration of 2.5 mg/mL. Freshly prepared collagen solution was added to each well of a 24-well plate and incubated at 37° C. in 5% $CO_2$ for 1 hour. Cultured ARPE-19, ARPE-19/EMP2, and ARPE-19/EMP2 siRNA cells were harvested and resuspended in serum-free DMEM/F12 at a final concentration of $5 \times 10^5$/mL. Cells were pretreated for 1 hour with various concentrations of small-molecule inhibitors. Inhibitors PP2 (FAK/Src inhibitor), and SU6656 (Src inhibitor) were used diluted in DMSO (Calbiochem). The cells were treated with DMSO alone as a vehicle control. ARPE-19, ARPE-19/EMP2, and ARPE-19/EMP2 siRNA cells were seeded onto the collagen gels at a concentration of $2.5 \times 10^5$ cells per well and the percentage of contraction was measured at specific time intervals. At least three independent experiments were performed and, where indicated, the results were evaluated for statistical significance with a Student's t-test (unpaired, one tail). A level of $P<0.05$ was considered to be statistically significant.

Western Blot Analysis:

Western blot analysis was performed as previously described (Wadehra M et al. *Dev Biol,* 292(2):430-441 (2006)). Briefly, cell protein was isolated by using RIPA buffer containing protease and phosphatase inhibitors (Upstate, Charlottesville, Va.) and the protein concentration determined with a protein assay (BCA; Bio-Rad). A total of 10 µg protein was loaded in each lane and the proteins fractionated by 4% to 20% SDS-PAGE gradient gel in reducing conditions. Proteins were transferred to nitrocellulose membranes (GE Healthcare, Buckinghamshire, UK) and the adequacy of transfer confirmed by Ponceau S red staining (Sigma-Aldrich). The membrane was then blocked with nonfat milk in TBS Tween (TBST; Upstate). Blots were incubated for 1 hour with primary antibody at a dilution of 1:200 for FAK and p-FAK (Tyr 576/577), 1:1000 for EMP2, and 1:5000 for β-actin. Horseradish peroxidase-conjugated goat anti-rabbit or horseradish peroxidase-conjugated goat anti-mouse was exposed to the blots at a 1:2000 dilution. The blots were then developed with chemiluminescence to visualize bound antibody (ECL; Pierce, Rockford, Ill.) and quantified with β-actin as the internal control. The Western blot analyses were quantified with NIH Image J. The blots were digitized with a flatbed scanner, and the band density was measured by using Image J. To account for loading variability, β-actin was used to normalize each sample. At least three independent experiments were performed and, where indicated, the results were evaluated for statistical significance with a Student's t-test (unpaired, one-tall). A level of P<0.05 was considered to be statistically significant.

Results

Figure 13:
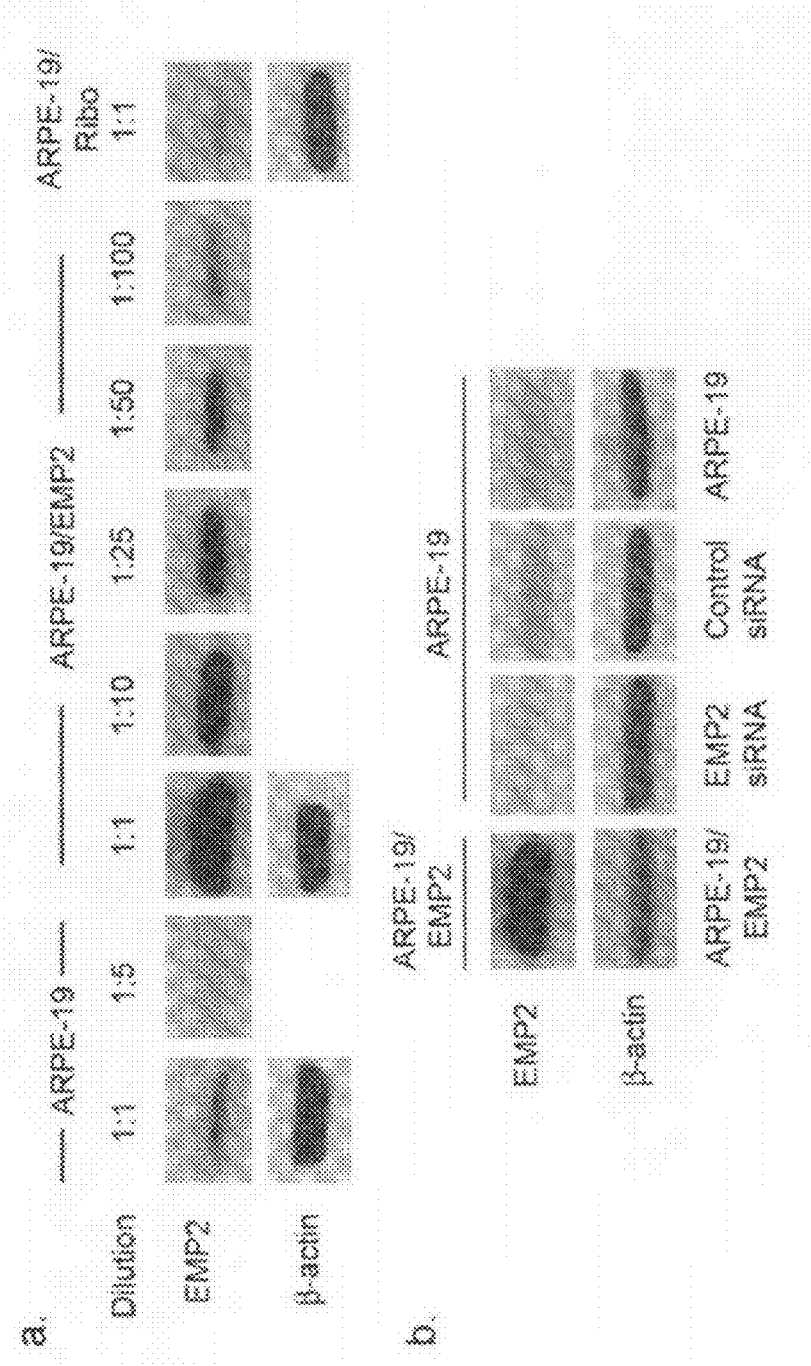
FIG. 13. Recombinant modification of LMP2 expression. A. Steady state protein levels of EMP2 were measured by Western blot analysis in ARPE-19 cells (control cells), ARPE-19/EMP2 cells (increased EMP2), and ARPE-19/Ribo cells (decreased EMP2). To measure the increase in EMP2 expression, various dilutions (1:10, 1:25, 1:50, and 1:100) of ARPE-19/EMP2 cell lysates were evaluated. B. ARPE-19 cells were transiently transfected with siRNA specific for EMP2 (ARPE-19/EMP2 siRNA) or with a control scramble siRNA (ARPE-19/control siRNA). Experiments were performed independently at least three times, with similar results.

Recombinant Modification of EMP2 Expression in ARPE-19 Cells:

EMP2 is highly expressed in retinal pigment epithelium cells, which are believed to be important in membrane formation and contraction of collagen gels. To study the affect of EMP2 on collagen gel contraction, EMP2 levels were modified in the ARPE-19 cell line to create two additional lines of ARPE-19: an overexpressing line, designated ARPE-19/EMP2, and a stable knockdown, designated ARPE-19/Ribo. Steady state protein levels of EMP2 were measured by Western blot analysis in ARPE-19 cells, ARPE-19/EMP2 cells, and ARPE-19/Ribo cells. Experiments were performed independently at least three times with similar results, and one representative experiment is shown in FIG. 13A. ARPE-19/EMP2 cells showed a 75- to 100-fold increase in EMP2 expression compared with wild-type cells when compared by using serial dilution. ARPE-19/Ribo cells showed a fivefold decrease in EMP2 expression compared with ARPE-19 cells.

An alternative method for decreasing EMP2 expression used ARPE-19 cells that were transiently transfected with siRNA specific for EMP2 (ARPE-19/EMP2 siRNA) or with a control scramble siRNA (ARPE-19/control siRNA). This technique using the specific siRNA, specifically reduced EMP2 expression to approximately 40% of the expression in control ARPE-19 (FIG. 13B). The scramble siRNA did not result in any change in EMP2 expression.

Figure 14:
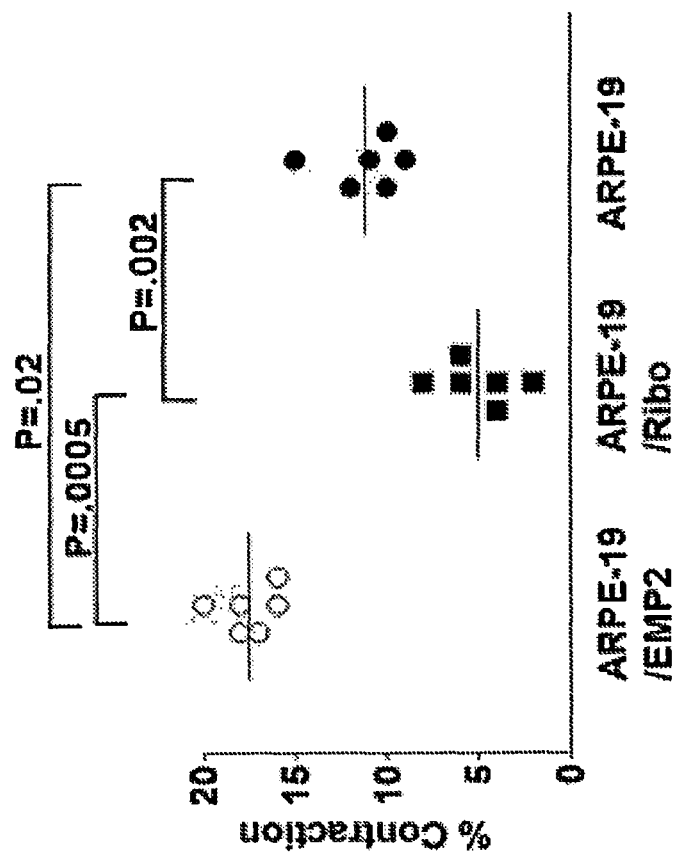
FIG. 14. EMP2 modification affected collagen gel contraction. A collagen gel contraction assay was performed in ARPE-19/EMP2, ARPE-19/Ribo, and ARPE-19 cells. Cell lines with elevated and decreased EMP2 expression resulted in a 57% increase and 55% decrease in gel contraction, respectively (P=0.002). Experiments were performed independently at least three times with similar results FIG. 15. Collagen binding integrins. Cell surface expression was measured by flow cytometry with monoclonal antibodies against α1, α2, or α3 integrin. A. Histograms of representative experiments are presented. The isotype control staining is shown as an open tracing, and the specific staining pattern is shaded. A numerical value for the mean fluorescence intensity is presented in the top right corner of each panel. B. The surface expression of each of these integrins was evaluated in three independent experiments and the results tabulated with the mean presented. Statistical comparison of expression of each integrin in the two cell lines was performed with Student's t-test (unpaired, one-tailed).

EMP2 Modification of Collagen Gel Contraction:

The collagen gel contraction assay of ARPE-19/EMP2 cells, ARPE19/Ribo cells, and ARPE-19 cells was preformed at least three separate times with six replicates per sample. Altering EMP2 levels significantly affected the cells' ability to contract the collagen gels. Increasing EMP2 expression significantly increased contraction compared with untreated wild-type cells (FIG. 14). Concordantly, decreased gel contraction was observed in the ARPE-19/Ribo cells. Additional control ARPE-19 cell lines, a retrovirally infected cell line without the EMP2 construct, and the transfected EGFP-N3 vector without ribozyme, did not alter contraction compared with the wild-type control ARPE-19 cell line (data not shown).

Effect of EMP2 on Contraction Through Changes in Integrins α1, α2, or α3:

The previous results indicated that increasing EMP2 expression results in increased collagen gel contraction. EMP2 is known to regulate intracellular trafficking and cell surface expression of specific integrin isoforms in various cell types including the mouse NIH3T3 and the human endometrial cancer line HEC1A (Wadehra M et al., *Dev Biol*, 287(2):336-345 (2005); Wadehra M et al., *J. Biol. Chem.*, 277(43):41094-41100 (2002)) We and others demonstrated the importance of α1, α2, and α3 integrin engagement as an important step in collagen gel contraction in the ARPE-19 cell line (Bando H et al., *Exp Eye Res*, 82(3):529-537 (2006); Morales S A et al., *Exp Eye Res*, 85(6):790-798 (2007); Carver W et al., *J Cell Physiol*, 165(2):425-437 (1995); Cooke M E et al., *J Cell Sci*, 113:2375-2383 (2000); Kieffer J D et al., *Biochem Biophys Res Commun*, 217(2): 466-474 (1995); Langholz O et al., *J. Cell Biol.*, 131:1903-1915 (1995); Moulin V and Plamondon M., *Br J Dermatol*, 147(5):886-892 (2002); Robbins S G et al., *Invest Ophthalmol Vis Sci*, 35(9):3475-3485 (1994); Zhang Z G et al., *J Cell Sci*, 119:1886-1895 (2006)) and thus hypothesized that EMP2 may increase the cell surface expression of one of these collagen-binding integrins.

Figure 15:
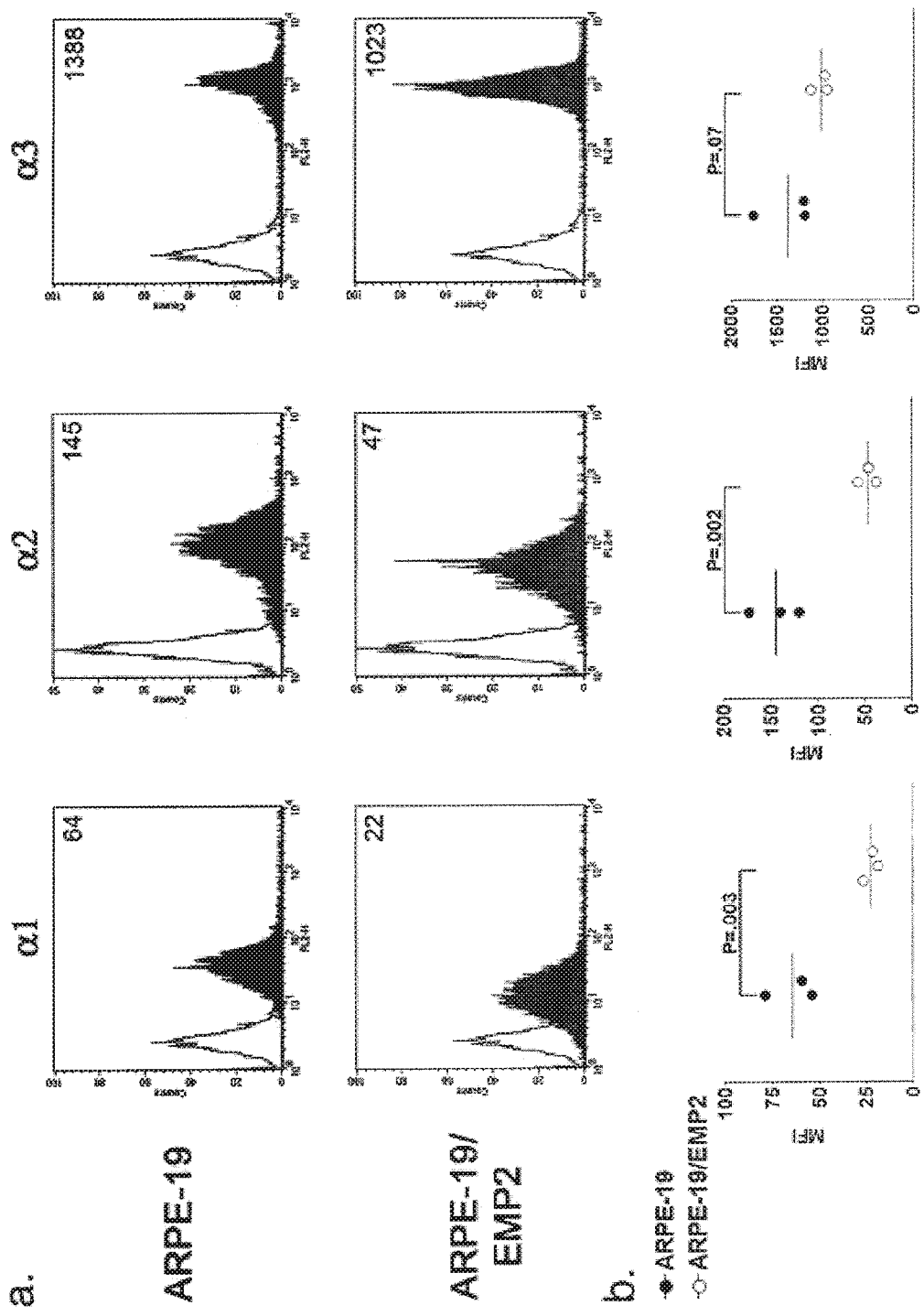

The cell lines with altered EMP2 expression were evaluated for surface expression of these integrin isoforms by flow cytometry (FIG. 15). In contrast to the predicted result, cells engineered to overexpress EMP2 actually exhibited decreased cell surface expression of integrin α1 (P=0.003) and α2 (P=0.002) by approximately 65%. There was a slight but not statistically significant decrease in integrin α3 expression in the ARPE-19/EMP2 cells (FIG. 15B). This result led us to investigate other mechanisms by which EMP2 could regulate collagen gel contraction in this cell line.

Figure 16:
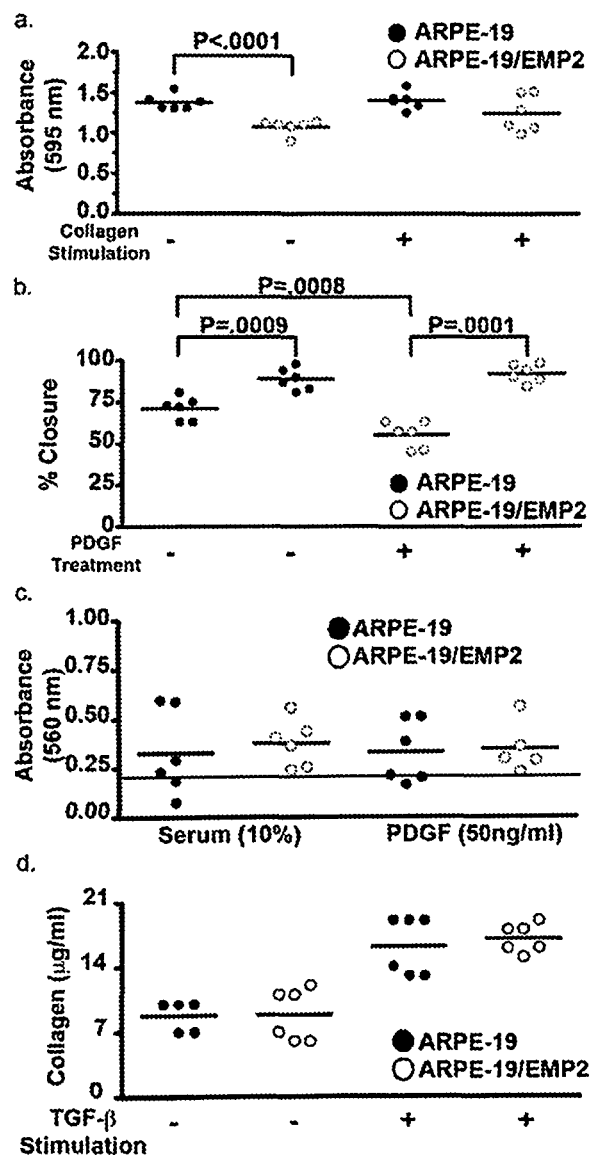
FIG. 16. Increased EMP levels decreased proliferation and migration but had no effect on invasion or collagen production. A. ARPE-19 and ARPE-19/EMP2 cells were treated with normal medium or 25 mg/mL collagen I and incubated for 48 hours, and proliferation was assessed by BrdU incorporation. B. The effect of EMP2 expression on cell migration. ARPE-19 and ARPE-19/EMP2 cells were plated in a 24-well plate, and once confluent, a scratch was made and migration was measured at various time points. ARPE-19 and ARPE-19/EMP2 cells were either left untreated or were treated with 50 ng/mL PDGF, and migration was measured after 24 hours. C. ARPE-19 and ARPE-19/EMP2 cells were seeded on an invasion chamber insert with 8-μm pore size polycarbonate membrane coated with a thin layer of polymerized collagen. Either 10% PBS or 50 ng/ml PDGF was used as a chemoattractant. Invasive cells migrated through the polymerized collagen layer, clung to the bottom of the polycarbonate membrane, and were detected by staining, extraction, and measurement by a microplate reader (560 nm). D. ARPE-19 and ARPE-19/ EMP2 cells were grown in serum-free medium in the presence or absence of 10 ng/mL TGF-β for 72 hours. The media were collected and collagen production was measured by ELISA. There was no statistically significant change in collagen production in the presence or absence of TGF-β. However, TGF-β increased collagen production in each cell line compared with the untreated condition. All studies were performed at least three separate times with six wells per sample. The results were evaluated for statistical significance with a Student's t-test (unpaired, one-tailed). P<0.05 was considered to be statistically significant.

Association of Changes in Proliferation, Migration, Invasion, and Collagen Production with the Effect of EMP2 on Contraction:

A potential mechanism by which EMP2 may regulate collagen contraction is by increasing cell proliferation leading to increased contraction. Proliferation, assayed by BrdU incorporation, was assessed in the ARPF-19 and ARPE-19/EMP2 cells in the absence or presence of collagen stimulation (FIG. 16A). In the absence of collagen, EMP2 overexpression resulted in a mild decrease in proliferation (20%). After collagen stimulation, there was no statistically significant difference in the proliferation of either cell line, thus refuting the hypothesis that increased proliferation may lead to enhanced collagen gel contraction by ARPE-19/EMP2 cells.

To investigate the possible effect of increased EMP2 expression on migration, we performed a wound-healing assay. ARPE-19 and ARPE-19/EMP2 cells were either left untreated or treated with 50 ng/mL PDGF, and the percentage of closure, as a surrogate evaluation of wound closure, was measured at 6, 12, and 24 hours. At the 6- and 12-hour time points, in the absence or presence of PDGF, there was no difference between the two cells lines (data not shown). At the 24-hour time point, in the absence of PDGF stimulation, the ARPE-19/EMP2 cells showed a 23% decrease in gap closure compared with the ARPE-19 cells. PDGF treatment abolished this effect, resulting in equivalent wound healing in the two cell lines (FIG. 16B). Both proliferation and migration are responsible for wound closure. Although the lower proliferative rate of the ARPE-19/EMP2 cells could be responsible for the decrease in wound closure, it is also possible that the EMP2-overexpressing cells exhibit less motility. PDGF treatment, known to promote the motile phenotype, both stimulated wound closure of the ARPE-19 cells and overcame the decreased wound closure of the ARPE-19/EMP2 cells. Increased collagen gel contraction by the ARPE-19/EMP2 cells cannot be explained by increases in migration due to altered EMP2 expression.

We examined an alternative mechanism, the possibility that EMP2 expression could influence the cells ability to invade the collagen matrix. ARFE-19 cells and ARPE-19/EMP2 cells were seeded onto polycarbonate membranes and either 10% FBS or 50 ng PDGF was used as a chemoattractant. Invasion was measured at 24 and 48 hours. There was no difference in invasion between the ARPE-19 and ARPE-19/EMP2 cells under either condition (FIG. 16C). EMP2-mediated enhancement of collagen gel contraction does not result from an altered invasive capacity.

An additional mechanism that we investigated was whether EMP2 levels affect collagen production. ARPE-19 and ARPE-19/EMP2 cells were grown in a 24-well plate for 72 hours. The medium was collected and collagen production was analyzed. There was no statistical difference in collagen production between the two cell lines (FIG. 16D). Increased cellular contractile capacity by ARPE-19/EMP2 cells cannot be explained by altered collagen production.

Figure 17:
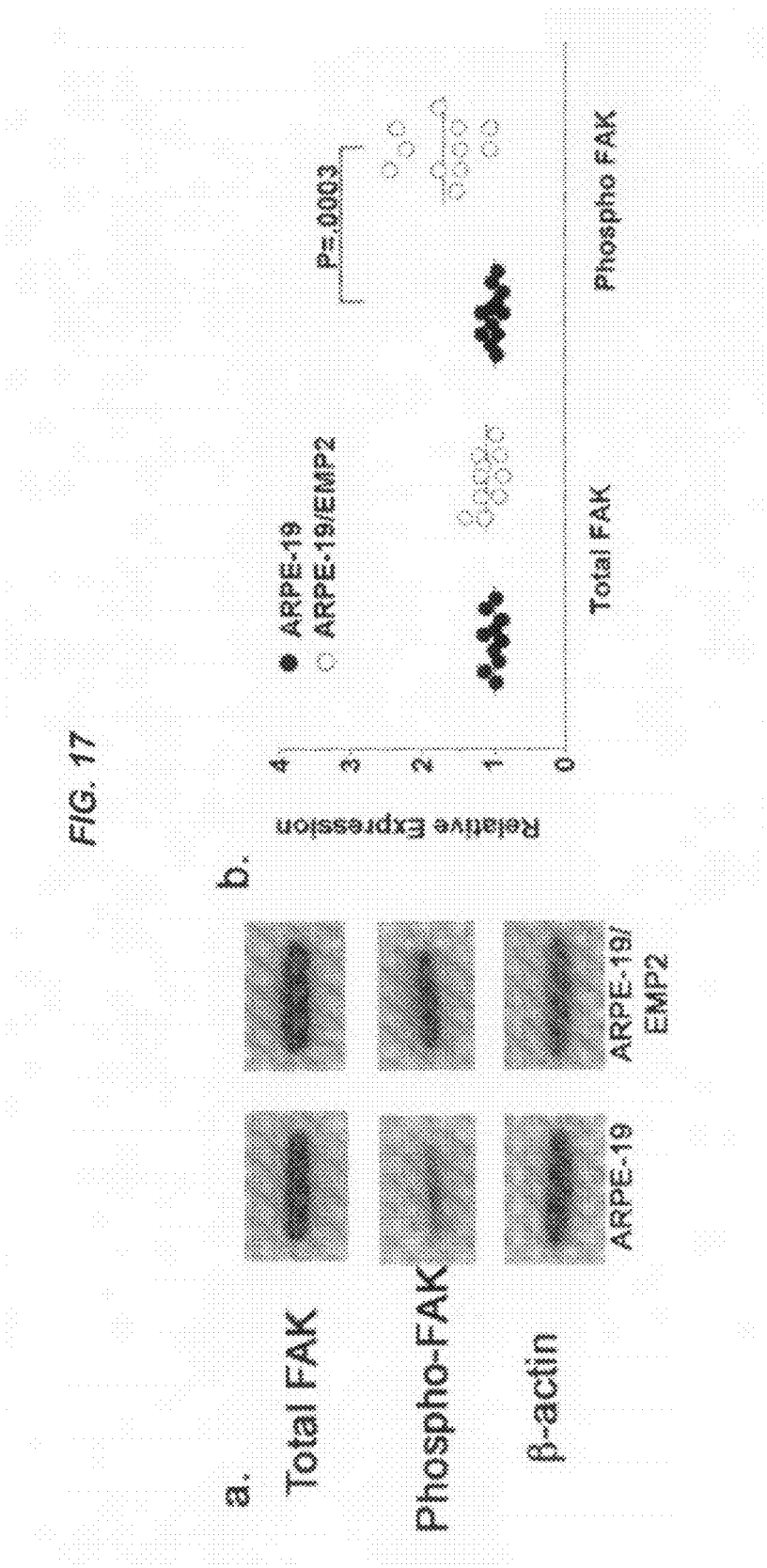
FIG. 17. EMP2 overexpression increased FAK activation. Cell extracts (10 μg protein) were fractionated by 4% to 20% SDS-PAGE gradient gel in reducing conditions, and Western immunoblots were probed with antibodies for FAK, pFAK, and β-actin. A: representative immunoblots; B: experiments were performed independently at least three times with similar results. Band density, normalized to the β-actin loading control, was quantitated. Experiments were performed independently at least three times with similar results.

EMP2 Control of FAK Activation and Collagen Gel Contraction in ARPE-19 Cells:

Changes in integrin expression, proliferation, migration, or invasion do not explain how increased EMP2 expression results in increased gel collagen contraction. Previously, we observed that integrin ligation and activation of FAK/Src complex are necessary for collagen gel contraction by ARPE-19 cells (Morales S A et al., *Exp Eye Res,* 85(6):790-798 (2007)). We investigated whether EMP2 overexpression in the ARPE-19 cells led to alteration in FAK/Src activity. Although total FAK levels were equivalent in, both the ARPE-19 and ARPE-19/EMP2 cells, the overexpressing ARP-19/EMP2 cells demonstrated an almost twofold increase in the level of activated FAK compared with the control ARPE-19 cells (FIG. 17A). Multiple evaluations, in which each activated FAK was normalized to its own β-actin loading control, showed a statistically significant correlation between increased EMP2 levels and FAK activation (FIG. 17B).

Figure 18:
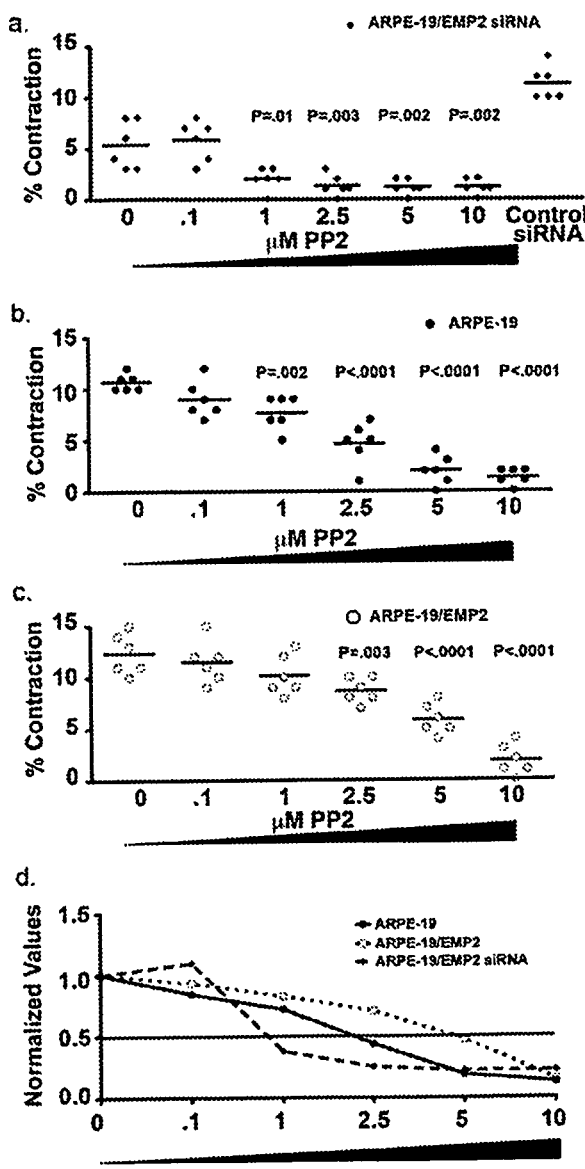
FIG. 18. EMP2 overexpression increased resistance to PP2. Cells were pretreated for 1 hour with various concentrations of the small-molecule inhibitor PP2 (FAK/Src inhibitor), and gel contraction was assessed. The experiment was preformed at least three separate times with six replicates per sample, and a representative experiment is presented (A-C). Statistical analysis was performed with Student's t-test for each concentration of inhibitor compared with the vehicle-only control. A. ARPE-19/EMP2 siRNA cells with decreased EMP2 expression. B. ARPE-19 cells. C. EMP2-overexpressing ARPE-19/EMP2 cells. D. Each point represents the average inhibition of contraction at each concentration for each cell line normalized to total contraction of the same cell line exposed to the vehicle control. Experiments were performed independently at least three times with similar results.
Figure 19:
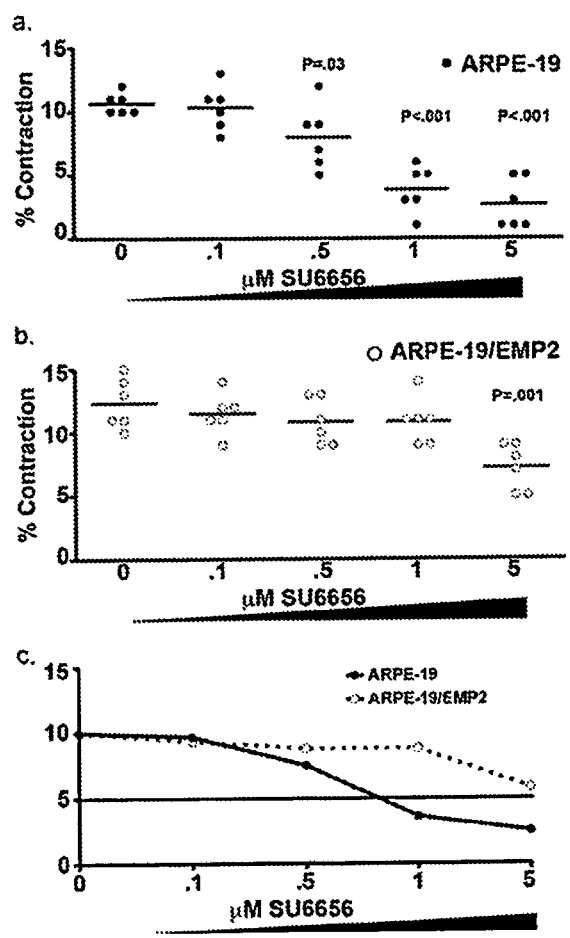
FIG. 19. EMP2 overexpression increased resistance to inhibition by SU6656. Cells were pretreated for 1 hour with various concentrations of the small-molecule inhibitor SU6656 (a FAK/Src inhibitor), and gel contraction was assessed. The experiment was preformed at least three separate times with six replicates per sample, and a representative experiment is presented. Statistical analysis was performed with a Student's t-test for each concentration of inhibitor compared with the vehicle-only control. A. ARPE-19/EMP2 cells. B. EMP2 overexpressing ARPE-19/EMP2 cells. C. Each point represents the average inhibition of contraction at each concentration for each cell line normalized to total contraction of the same cell line exposed to the vehicle control. Experiments were performed independently at least three times with similar results.

Effect of EMP2 Overexpression on Resistance to Inhibition of Collagen Gel Contraction by FAK/Src Inhibitors:

The observation that overexpression of EMP2 was associated with increased FAK activation prompted additional studies to test the functional significance of this observation in the context of gel contraction by using inhibitors of the FAK/Src pathway. If EMP2 effect was secondary to FAK activation, then the observed collagen gel contraction in the ARPE-19/EMP cells should show increased resistance to FAK/Src inhibition compared with the control ARPE-19 cells. To investigate this prediction, we used a range of concentrations of PP2 and SU6656, FAK/Src small-molecule inhibitors that have been demonstrated to prevent collagen gel contraction in ARPE-19 cells (Morales S A et al., *Exp Eye Res,* 85(6):790-798 (2007)) (FIGS. 18, 19). Reduction of EMP2 expression with an EMP2-specific siRNA showed deceased collagen gel contraction compared with control scramble siRNA. This result was concordant with the decreased collagen gel contraction observed in the ARPE-19/Ribo cell line (FIG. 18A). The sensitivity of the collagen gel contraction assay to the FAK inhibitor PP2 correlated inversely with the EMP2 levels, there was increased sensitivity in the EMP2 siRNA-treated cells and increased resistance in the EMP2-overexpressing cells (FIGS. 18A-C). The percentage inhibition of contraction, as normalized to the vehicle control, was determined for each cell line at the different concentrations of inhibitor. The concentrations of PP2 required to achieve 50% inhibition of the gel contraction were 2.5 µM for the ARPE-19 cells, less than 1 µM for the ARPE-19/EMP2 siRNA cells, and 5 µM for the overexpressing ARPE-19/EMP2 cells and were consistent with the changes in FAK activation observed in these cell lines (FIG. 18D). A second inhibitor of the FAK/Src pathway, SU6656, demonstrated similar results in the ARPE-19 and the ARPE-19/EMP2 cells, thus providing independent confirmation that the mechanism for EMP2 control of collagen gel contraction was through changes in the activation of FAK (FIG. 19).

Discussion

Collagen gel contraction, an in vitro correlate for PVR, is a cellular process dependent on FAK-mediated integrin signaling (Morales S A et al., *Exp Eye Res,* 85(6):790-798 (2007)). In this article, we demonstrate that EMP2 modulates collagen gel contraction in a process dependent on enhanced FAK activation. EMP2 regulation of FAK activation is a novel observation, but prior observations of tetraspanin-associated regulation of a variety of integrin signaling mechanisms suggests a potential shared function for this family of membrane-associated proteins.

The mechanisms by which tetraspanins regulate activation of FAK-dependent or other signaling pathways are not yet understood. Certain tetraspanins (CD9, CD53, CD81, CD82, and CD151) associate with each other or in heterocomplexes with additional membrane proteins, resulting in increased tyrosine phosphorylation (Boucheix C et al., *Cell Mol Life Sci,* 58(9):1189-1205 (2001); Hemler M E., *J Cell Biol,* 155(7):1103-1107 (2001); Hong I K et al., *J Biol Chem,* 281(34):24279-24292 (2006); Lagaudriere-Gesbert C et al., *Cell Immunol,* 182(2):105-112 (1997); Todd S C et al., *J Exp Med,* 184(5):2055-2060 (1996)). This implies that 4-transmembrane proteins act as molecular adaptors supporting the functional assembly of signaling complexes in the membrane (Hong I K et al., *J Biol Chem,* 281(34):24279-24292 (2006)).

Functional modulation of integrin and other cell surface receptors is a recurrently observed feature common to multiple proteins in the tetraspan families. Several tetraspanins (CD9, CD53, CD81, and CD82) participate in protein-protein interaction with integrins (α3β1, α43β1, and α63β1), leading to altered adhesion and cellular activation (Lagaudriere-Gesbert C et al., *Cell Immunol,* 182(2):105-112 (1997); Todd S C et al., *J Exp Med,* 184(5):2055-2060 (1996)). Multiple tetraspanins, including CD9, CD63, CD81, CD151, and A15/TALLA1, recruit PI-4 kinase to specific membrane locations and induce phosphoinositide-dependent signaling (Yauch R L and Hemler M E., *Biochem J,* 3:629-637 (2000)). In addition, cross-linking of CD81 with anti-CD81 antibody is costimulatory for signaling through the TCR/CD3 complex (Todd S C et al., *J Exp Med,* 184(5):2055-2060 (1996)). Other relationships between changes in expression levels or cross-linking of tetraspanins have been associated with activation of signal transduction including upregulated CD53 expression or ligation, which induces JNK activation (Yunta M et al., *Eur J Biochem,* 269(3):1012-1021 (2002)); CD9 control of adhesion, induced tyrosine phosphorylation of FAK in fibrosarcoma cells (Berditchevski F and Odintsova E, *J Cell Biol,* 146(2):477-492 (1999)); and homophilic CD151 interactions, which induce adhesion-dependent activation of FAK, Src, and c-Jun kinases in human melanoma cells (Hong I K et al., *J Biol Chem,* 281(34):24279-24292 (2006)). In addition, homophilic protein-protein interactions of CD151 regulate integrin-dependent signaling to c-Jun through a pathway involving FAK-Src and MAP kinases (Hong I K et al., *J Biol Chem,* 281(34):24279-24292 (2006)).

RPE-mediated collagen gel contraction involves the interplay of several receptors and signaling pathways (Bando H et al., *Exp Eye Res,* 82(3):529-537 (2006); Carver W et al., *J Cell Physiol,* 165(2):425-437 (1995); Cooke M E et al., *J Cell Sci,* 113:2375-2383 (2000); Kieffer J D et al., *Biochem Biophys Res Commun,* 217(2):466-474 (1995); Langholz O et al., *J. Cell Biol.*, 131:1903-1915 (1995); Moulin V and Plamondon M., *Br J Dermatol*, 147(5):886-892 (2002); Robbins S G et al., *Invest Ophthalmol Vis Sci*, 35(9):3475-3485 (1994); Zhang Z G et al., *J Cell Sci*, 119:1886-1895 (2006); Xia H et al., *J Biol Chem*, 279(31):33024-33034 (2004)). The results of this study support a role for EMP2 in facilitating the activation of the FAK/Src complex leading to collagen contraction.

Each publication, patent application, patent, and other reference cited herein is incorporated by reference in its entirety to the extent that it is not inconsistent with the present disclosure. In particular, all publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of reducing or inhibiting proliferative vitreoretinopathy or retinal detachment associated with traumatic injury, surgery or aberrant wound healing in a human subject, said method comprising administering an anti-EMP2 (Epithelial Membrane Protein-2) antibody that binds to EMP2 in the human subject, wherein the antibody comprises a heavy chain variable region comprising heavy chain three complementary-determining regions (CDR1-3) and a light chain variable region comprising three light chain complementary determining regions (CDR1-3), wherein:
  the sequence of heavy chain CDR1 of the antibody is SYAMH (SEQ ID NO: 12),
  the sequence of heavy chain CDR2 of the antibody is VISYDGSNKYYADSVKG (SEQ ID NO: 13),
  the sequence of heavy chain CDR3 of the antibody is DRRGRKSAGIDY (SEQ ID NO: 14),
  the sequence of light chain CDR1 of the antibody is QASQDISNYLN (SEQ ID NO: 15), the sequence of light chain CDR2 of the antibody is AASSLQS (SEQ ID NO: 16), and the sequence of light chain CDR3 of the antibody is LQDYNGWT (SEQ ID NO: 17), or the sequence of heavy chain CDR1 of the antibody is SYAMH (SEQ ID NO: 12), the sequence of heavy chain CDR2 of the antibody is VISYDGSNKYYADSVKG (SEQ ID NO: 13), the sequence of heavy chain CDR3 of the antibody is TVGATGAFDI (SEQ ID NO: 18), the sequence of light chain CDR1 of the antibody is RASQSIGKWLA (SEQ ID NO: 19), the sequence of light chain CDR2 of the antibody is KASSLEG (SEQ ID NO: 20), and the sequence of light chain CDR3 of the antibody is QQSHNFPPT (SEQ ID NO: 21);

wherein the anti-EMP2 antibody is a monoclonal antibody, a humanized antibody, or a chimeric antibody, a diabody, a minibody, a Fv fragment, a F(ab') fragment, or a F(ab')$_2$ fragment; and wherein the administering of the anti-EMP2 antibody reduces or inhibits proliferative vitreoretinopathy or retinal detachment associated with traumatic injury, surgery or aberrant wound healing in the subject.

2. The method of claim 1, wherein the anti-EMP2 agent is locally administered.

3. The method of claim 1, wherein the administration is directly to the eye.

4. The method of claim 1, wherein the anti-EMP2 antibody is administered intraocularly.

5. The method of claim 1, wherein the anti-EMP2 antibody is injected into the vitreous humor of the eye.

6. The method of claim 1, wherein the anti-EMP2 antibody specifically binds to an EMP2 polypeptide having the amino acid sequence selected from the group consisting of SEQ ID NO:1, SEQ ID NO:2, and SEQ ID NO:30.

7. The method of claim 1, wherein the antibody is a monoclonal antibody.

8. The method of claim 1, wherein the antibody is a humanized monoclonal antibody.

9. The method of claim 1, wherein the antibody is a diabody or a minibody.

10. The method of claim 1, wherein the antibody is a Fv, F(ab') or F(ab')2 fragment.

11. The method of claim 1, wherein the antibody is a chimeric antibody having a murine antigen-binding site and a humanized region that regulates effector function.

12. The method of claim 1, wherein the antibody is coupled to a cytotoxic agent.

13. The method of claim 1, wherein administration of the anti-EMP2 antibody reduces the risk of a retinal detachment.

14. The method of claim 1, wherein the anti-EMP2 antibody is formulated for injection into the eye.

15. The method of claim 1, wherein the anti-EMP2 antibody is formulated for local administration external to the eye.

16. The method of claim 1, wherein the vitreoretinopathy is rhegmatogenous vitreoretinopathy.

17. The method of claim 1, wherein prior to administration of the anti-EMP2 antibody, the eye suffered a traumatic injury or a surgery contributing to the risk of retinal detachment.

18. The method of claim 1 wherein:

the sequence of heavy chain CDR1 of the antibody is SYAMH (SEQ ID NO: 12), the sequence of heavy chain CDR2 of the antibody is VISYDGSNKYYADSVKG (SEQ ID NO: 13), the sequence of heavy chain CDR3 of the antibody is DRRGRKSAGIDY (SEQ ID NO: 14), the sequence of light chain CDR1 of the antibody is QASQDISNYLN (SEQ ID NO: 15), the sequence of light chain CDR2 of the antibody is AASSLQS (SEQ ID NO: 16), and the sequence of light chain CDR3 of the antibody is LQDYNGWT (SEQ ID NO: 17).

19. The method of claim 1 wherein:

the sequence of heavy chain CDR1 is SYAMH (SEQ ID NO: 12), the sequence of heavy chain CDR2 is VISYDGSNKYYADSVKG (SEQ ID NO: 13), the sequence of heavy chain CDR3 is TVGATGAFDI (SEQ ID NO: 18), the sequence of light chain CDR1 is RASQSIGKWLA (SEQ ID NO: 19), the sequence of light chain CDR2 is KASSLEG (SEQ ID NO: 20), and the sequence of light chain CDR3 is QQSHNFPPT (SEQ ID NO: 21).

20. A method of reducing or inhibiting proliferative vitreoretinopathy or retinal detachment associated with traumatic injury, surgery or aberrant wound healing in a human subject, said method comprising administering an anti-EMP2 (Epithelial Membrane Protein-2) antibody that binds to EMP2 in the human subject, wherein:

the sequence of heavy chain is the sequence of SEQ ID NO: 4, and the sequence of light chain is the sequence of SEQ ID NO: 5, or the sequence of heavy chain is the sequence of SEQ ID NO: 6, and the sequence of light chain is the sequence of SEQ ID NO: 7;

wherein the anti-EMP2 antibody is a monoclonal antibody, a humanized antibody, or a chimeric antibody, a diabody, a minibody, a Fv fragment, a F(ab') fragment, or a F(ab')$_2$ fragment; and wherein the administering of the anti-EMP2 antibody reduces or inhibits proliferative vitreoretinopathy or retinal detachment associated with traumatic injury, surgery or aberrant wound healing in the subject.

* * * * *

SEQUENCE LISTING

```
<160> NUMBER OF SEQ ID NOS: 32

<210> SEQ ID NO 1
<211> LENGTH: 167
<212> TYPE: PRT
<213> ORGANISM: Homo sapiens

<400> SEQUENCE: 1

Met Leu Val Leu Leu Ala Phe Ile Ile Ala Phe His Ile Thr Ser Ala
1               5                   10                  15

Ala Leu Leu Phe Ile Ala Thr Val Asp Asn Ala Trp Trp Val Gly Asp
                20                  25                  30

Glu Phe Phe Ala Asp Val Trp Arg Ile Cys Thr Asn Asn Thr Asn Cys
            35                  40                  45

Thr Val Ile Asn Asp Ser Phe Gln Glu Tyr Ser Thr Leu Gln Ala Val
        50                  55                  60

Gln Ala Thr Met Ile Leu Ser Thr Ile Leu Cys Cys Ile Ala Phe Phe
65                  70                  75                  80

Ile Phe Val Leu Gln Leu Phe Arg Leu Lys Gln Gly Glu Arg Phe Val
                85                  90                  95

Leu Thr Ser Ile Ile Gln Leu Met Ser Cys Leu Cys Val Met Ile Ala
                100                 105                 110

Ala Ser Ile Tyr Thr Asp Arg Arg Glu Asp Ile His Asp Lys Asn Ala
            115                 120                 125

Lys Phe Tyr Pro Val Thr Arg Glu Gly Ser Tyr Gly Tyr Ser Tyr Ile
        130                 135                 140

Leu Ala Trp Val Ala Phe Ala Cys Thr Phe Ile Ser Gly Met Met Tyr
145                 150                 155                 160

Leu Ile Leu Arg Lys Arg Lys
                165

<210> SEQ ID NO 2
<211> LENGTH: 20
<212> TYPE: PRT
<213> ORGANISM: Homo sapiens

<400> SEQUENCE: 2

Glu Asp Ile His Asp Lys Asn Ala Lys Phe Tyr Pro Val Thr Arg Glu
1               5                   10                  15

Gly Ser Tyr Gly
            20

<210> SEQ ID NO 3
<211> LENGTH: 1484
<212> TYPE: DNA
<213> ORGANISM: Homo sapiens
```

<400> SEQUENCE: 3

```
gaggggcccc gccgcctaga gggtggaggg agggcgcgca gtcccagccc agagcttcaa     60
aacagcccgg cggcctcgcc tcgcacccce agccagtccg tcgatccagc tgccagcgca    120
gccgccagcg ccggcacatc ccgctctggg ctttaaacgt gacccctcgc ctcgactcgc    180
cctgccctgt gaaatgttg gtgcttcttg ctttcatcat cgccttccac atcacctctg     240
cagccttgct gttcattgcc accgtcgaca atgcctggtg ggtaggagat gagttttttg    300
cagatgtctg gagaatatgt accaacaaca cgaattgcac agtcatcaat gacagctttc    360
aagagtactc cacgctgcag gcggtccagg ccaccatgat cctctccacc attctctgct    420
gcatcgcctt cttcatcttc gtgctccagc tcttccgcct gaagcaggga gagaggtttg    480
tcctaacctc catcatccag ctaatgtcat gtctgtgtgt catgattgcg gcctccattt    540
atacagacag gcgtgaagac attcacgaca aaaacgcgaa attctatccc gtgaccagag    600
aaggcagcta cggctactcc tacatcctgg cgtgggtggc cttcgcctgc accttcatca    660
gcggcatgat gtacctgata ctgaggaagc gcaaatagag ttccggagct gggttgcttc    720
tgctgcagta cagaatccac attcagataa ccattttgta tataatcatt attttttgag    780
gttttttctag caaacgtatt gtttccttta aagccaaaa aaaaaaaaaa aaaaaaaaa     840
aaaaaaaaaa aaaaaaaaa aatccaaaag agagaagagt ttttgcattc ttgagatcag    900
agaatagact atgaaggctg gtattcagaa ctgctgccca ctcaaaagtc tcaacaagac    960
acaagcaaaa atccagcaat gctcaaatcc aaaagcactc ggcaggacat ttcttaacca   1020
tgggggctgtg atgggaggag aggagaggct gggaaagccg ggtctctggg gacgtgcttc   1080
ctatgggttt cagctggccc aagcccctcc cgaatctctc tgctagtggt gggtggaaga   1140
gggtgaggtg gggtatagga gaagaatgac agcttcctga gaggtttcac ccaagttcca   1200
agtgagaagc aggtgtagtc cctggcattc tgtctgtatc caaaccagag cccagccatc   1260
cctccggtat tggggtgggt cagaaaaagt ctcacctcaa tttgccgaca gtgtcacctg   1320
cttgccttag gaatggtcat ccttaacctg cgtgccagat ttagactcgt ctttaggcaa   1380
aacctacagc gccccccct caccccagac ctacagaatc agagtcttca agggatgggg   1440
ccagggaatc tgcatttcta atgcgctccc tgggcaacgc ttca                    1484
```

<210> SEQ ID NO 4
<211> LENGTH: 122
<212> TYPE: PRT
<213> ORGANISM: Homo sapiens

<400> SEQUENCE: 4

```
Met Ala Gln Val Gln Leu Val Gln Ser Gly Gly Val Val Gln Pro
1               5                   10                  15

Gly Arg Ser Leu Arg Leu Ser Cys Ala Ala Ser Gly Phe Thr Phe Ser
                20                  25                  30

Ser Tyr Ala Met His Trp Val Arg Gln Ala Pro Gly Lys Gly Leu Glu
            35                  40                  45

Trp Val Ala Val Ile Ser Tyr Asp Gly Ser Asn Lys Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Ala Arg Asp Arg Arg Gly Arg Lys Ser Ala Gly Ile Asp Tyr
                100                 105                 110

Trp Gly Gln Gly Thr Leu Val Thr Val Ser
        115                 120

<210> SEQ ID NO 5
<211> LENGTH: 124
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Gly Trp Thr
                85                  90                  95

Phe Gly Gln Gly Thr Lys Val Asp Ile Lys Arg Ala Ala Ala Glu Gln
            100                 105                 110

Lys Leu Ile Ser Glu Glu Asp Leu Asn Gly Ala Ala
        115                 120

<210> SEQ ID NO 6
<211> LENGTH: 121
<212> TYPE: PRT
<213> ORGANISM: Homo sapiens

<400> SEQUENCE: 6

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Thr Val Gly Ala Thr Gly Ala Phe Asp Ile Trp Gly
            100                 105                 110

Gln Gly Thr Met Val Thr Val Ser Ser
        115                 120

<210> SEQ ID NO 7
<211> LENGTH: 125
<212> TYPE: PRT
<213> ORGANISM: Homo sapiens
```

-continued

<400> SEQUENCE: 7

```
Asp Ile Val Met Thr Gln Ser Pro Ser Thr Val Ser Ala Ser Val Gly
1               5                   10                  15

Asp Arg Val Ile Ile Pro Cys Arg Ala Ser Gln Ser Ile Gly Lys Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Gly Trp Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Ser Ala Thr Tyr Val Cys Gln Gln Ser His Asn Phe Pro Pro
                85                  90                  95

Thr Phe Gly Gly Gly Thr Lys Leu Glu Ile Lys Arg Ala Ala Ala Glu
            100                 105                 110

Gln Lys Leu Ile Ser Glu Glu Asp Leu Asn Gly Ala Ala
        115                 120                 125
```

<210> SEQ ID NO 8
<211> LENGTH: 119
<212> TYPE: PRT
<213> ORGANISM: Homo sapiens

<400> SEQUENCE: 8

```
Met Ala Gln Val Gln Leu Val Gln Ser Gly Gly Gly Leu Val Gln Pro
1               5                   10                  15

Gly Arg Ser Leu Arg Leu Ser Cys Ala Ala Ser Gly Phe Ser Phe Ser
            20                  25                  30

Glu Tyr Pro Met His Trp Val Arg Gln Ala Pro Gly Arg Gly Leu Glu
        35                  40                  45

Ser Val Ala Val Ile Ser Tyr Asp Gly Glu Tyr Gln Lys Tyr Ala Asp
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Pro Glu Asp Thr Ala Val Tyr
                85                  90                  95

Tyr Cys Ala Arg Thr Ile Asn Asn Gly Met Asp Val Trp Gly Gln Gly
            100                 105                 110

Thr Thr Val Thr Val Ser Ser
        115
```

<210> SEQ ID NO 9
<211> LENGTH: 124
<212> TYPE: PRT
<213> ORGANISM: Homo sapiens

<400> SEQUENCE: 9

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Glu Leu Leu Ile
        35                  40                  45

Tyr Gly Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Ser Ala Thr Tyr Tyr Cys Leu Gln Asp Tyr Asn Gly Trp Thr
                85                  90                  95

Phe Gly Gln Gly Thr Lys Leu Glu Ile Lys Arg Ala Ala Ala Glu Gln
            100                 105                 110

Lys Leu Ile Ser Glu Glu Asp Leu Asn Gly Ala Ala
        115                 120

<210> SEQ ID NO 10
<211> LENGTH: 119
<212> TYPE: PRT
<213> ORGANISM: Homo sapiens

<400> SEQUENCE: 10

Met Ala Gln Val Gln Leu Val Gln Ser Gly Gly Gly Leu Val Gln Pro
1               5                   10                  15

Gly Arg Ser Leu Arg Leu Ser Cys Ala Ala Ser Gly Phe Ser Phe Ser
            20                  25                  30

Glu Tyr Pro Met His Trp Val Arg Gln Ala Pro Gly Arg Gly Leu Glu
        35                  40                  45

Ser Val Ala Val Ile Ser Tyr Asp Gly Glu Tyr Gln Lys Tyr Ala Asp
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Pro Glu Asp Thr Ala Val Tyr
                85                  90                  95

Tyr Cys Ala Arg Thr Ile Asn Asn Gly Met Asp Val Trp Gly Gln Gly
            100                 105                 110

Thr Thr Val Thr Val Ser Ser
        115

<210> SEQ ID NO 11
<211> LENGTH: 124
<212> TYPE: PRT
<213> ORGANISM: Homo sapiens

<400> SEQUENCE: 11

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Glu Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Leu Gln Asp Tyr Asn Gly Trp Thr
                85                  90                  95

Phe Gly Gln Gly Thr Lys Leu Glu Ile Lys Arg Ala Ala Ala Glu Gln
            100                 105                 110

Lys Leu Ile Ser Glu Glu Asp Leu Asn Gly Ala Ala
        115                 120
```

```
<210> SEQ ID NO 12
<211> LENGTH: 5
<212> TYPE: PRT
<213> ORGANISM: Homo sapiens

<400> SEQUENCE: 12

Ser Tyr Ala Met His
1               5

<210> SEQ ID NO 13
<211> LENGTH: 17
<212> TYPE: PRT
<213> ORGANISM: Homo sapiens

<400> SEQUENCE: 13

Val Ile Ser Tyr Asp Gly Ser Asn Lys Tyr Tyr Ala Asp Ser Val Lys
1               5                   10                  15

Gly

<210> SEQ ID NO 14
<211> LENGTH: 12
<212> TYPE: PRT
<213> ORGANISM: Homo sapiens

<400> SEQUENCE: 14

Asp Arg Arg Gly Arg Lys Ser Ala Gly Ile Asp Tyr
1               5                   10

<210> SEQ ID NO 15
<211> LENGTH: 11
<212> TYPE: PRT
<213> ORGANISM: Homo sapiens

<400> SEQUENCE: 15

Gln Ala Ser Gln Asp Ile Ser Asn Tyr Leu Asn
1               5                   10

<210> SEQ ID NO 16
<211> LENGTH: 7
<212> TYPE: PRT
<213> ORGANISM: Homo sapiens

<400> SEQUENCE: 16

Ala Ala Ser Ser Leu Gln Ser
1               5

<210> SEQ ID NO 17
<211> LENGTH: 8
<212> TYPE: PRT
<213> ORGANISM: Homo sapiens

<400> SEQUENCE: 17

Leu Gln Asp Tyr Asn Gly Trp Thr
1               5

<210> SEQ ID NO 18
<211> LENGTH: 10
<212> TYPE: PRT
<213> ORGANISM: Homo sapiens

<400> SEQUENCE: 18

Thr Val Gly Ala Thr Gly Ala Phe Asp Ile
1               5                   10
```

```
<210> SEQ ID NO 19
<211> LENGTH: 11
<212> TYPE: PRT
<213> ORGANISM: Homo sapiens

<400> SEQUENCE: 19

Arg Ala Ser Gln Ser Ile Gly Lys Trp Leu Ala
1               5                   10

<210> SEQ ID NO 20
<211> LENGTH: 7
<212> TYPE: PRT
<213> ORGANISM: Homo sapiens

<400> SEQUENCE: 20

Lys Ala Ser Ser Leu Glu Gly
1               5

<210> SEQ ID NO 21
<211> LENGTH: 9
<212> TYPE: PRT
<213> ORGANISM: Homo sapiens

<400> SEQUENCE: 21

Gln Gln Ser His Asn Phe Pro Pro Thr
1               5

<210> SEQ ID NO 22
<211> LENGTH: 5
<212> TYPE: PRT
<213> ORGANISM: Homo sapiens

<400> SEQUENCE: 22

Glu Tyr Pro Met His
1               5

<210> SEQ ID NO 23
<211> LENGTH: 17
<212> TYPE: PRT
<213> ORGANISM: Homo sapiens

<400> SEQUENCE: 23

Val Ile Ser Tyr Asp Gly Glu Tyr Gln Lys Tyr Ala Asp Ser Val Lys
1               5                   10                  15

Gly

<210> SEQ ID NO 24
<211> LENGTH: 8
<212> TYPE: PRT
<213> ORGANISM: Homo sapiens

<400> SEQUENCE: 24

Thr Ile Asn Asn Gly Met Asp Val
1               5

<210> SEQ ID NO 25
<211> LENGTH: 11
<212> TYPE: PRT
<213> ORGANISM: Homo sapiens

<400> SEQUENCE: 25

Arg Ala Ser Gln Gly Ile Arg Asn Asp Leu Gly
1               5                   10
```

```
<210> SEQ ID NO 26
<211> LENGTH: 7
<212> TYPE: PRT
<213> ORGANISM: Homo sapiens

<400> SEQUENCE: 26

Gly Ala Ser Ser Leu Gln Ser
1               5

<210> SEQ ID NO 27
<211> LENGTH: 257
<212> TYPE: PRT
<213> ORGANISM: Homo sapiens

<400> SEQUENCE: 27

Met Ala Gln Val Gln Leu Val Gln Ser Gly Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Arg Gly Arg Lys Ser Ala Gly Ile Asp Tyr
            100                 105                 110

Trp Gly Gln Gly Thr Leu Val Thr Val Ser Ser Gly Gly Gly Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Gln Ala Ser Gln Asp Ile Ser Asn Tyr Leu
145                 150                 155                 160

Asn Trp Tyr Gln Gln Lys Pro Gly Lys Ala Pro Lys Leu Leu Ile Tyr
                165                 170                 175

Ala Ala Ser Ser Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Leu Gln Asp Tyr Asn Gly Trp Thr Phe
    210                 215                 220

Gly Gln Gly Thr Lys Val Asp Ile Lys Arg Ala Ala Ala Glu Gln Lys
225                 230                 235                 240

Leu Ile Ser Glu Glu Asp Leu Asn Gly Ala Ala His His His His His
                245                 250                 255

His

<210> SEQ ID NO 28
<211> LENGTH: 257
<212> TYPE: PRT
<213> ORGANISM: Homo sapiens
```

<400> SEQUENCE: 28

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Thr Val Gly Ala Thr Gly Ala Phe Asp Ile Trp Gly
            100                 105                 110

Gln Gly Thr Met Val Thr Val Ser Ser Gly Gly Gly Ser Asp Ile
        115                 120                 125

Val Met Thr Gln Ser Pro Ser Thr Val Ser Ala Ser Val Gly Asp Arg
130                 135                 140

Val Ile Ile Pro Cys Arg Ala Ser Gln Ser Ile Gly Lys Trp Leu Ala
145                 150                 155                 160

Trp Tyr Gln Gln Lys Pro Gly Lys Ala Pro Lys Leu Leu Ile Tyr Lys
                165                 170                 175

Ala Ser Ser Leu Glu Gly Trp Val Pro Ser Arg Phe Ser Gly Ser Gly
            180                 185                 190

Ser Gly Thr Glu Phe Ser Leu Thr Ile Ser Ser Leu Gln Pro Asp Asp
        195                 200                 205

Ser Ala Thr Tyr Val Cys Gln Gln Ser His Asn Phe Pro Pro Thr Phe
    210                 215                 220

Gly Gly Gly Thr Lys Leu Glu Ile Lys Arg Ala Ala Ala Glu Gln Lys
225                 230                 235                 240

Leu Ile Ser Glu Glu Asp Leu Asn Gly Ala Ala His His His His
                245                 250                 255

His

<210> SEQ ID NO 29
<211> LENGTH: 254
<212> TYPE: PRT
<213> ORGANISM: Homo sapiens

<400> SEQUENCE: 29

Met Ala Gln Val Gln Leu Val Glu Ser Gly Gly Gly Leu Val Gln Pro
1               5                   10                  15

Gly Arg Ser Leu Arg Leu Ser Cys Ala Ala Ser Gly Phe Ser Phe Ser
            20                  25                  30

Glu Tyr Pro Met His Trp Val Arg Gln Ala Pro Gly Arg Gly Leu Glu
        35                  40                  45

Ser Val Ala Val Ile Ser Tyr Asp Gly Glu Tyr Gln Lys Tyr Ala Asp
50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Pro Glu Asp Thr Ala Val Tyr
                85                  90                  95

```
Tyr Cys Ala Arg Thr Ile Asn Asn Gly Met Asp Val Trp Gly Gln Gly
            100                 105                 110

Thr Thr Val Thr Val Ser Ser Ser Gly Gly Gly Ser Asp Ile Val Met
        115                 120                 125

Thr Gln Ser Pro Ser Ser Leu Ser Ala Ser Val Gly Asp Arg Val Thr
    130                 135                 140

Ile Thr Cys Arg Ala Ser Gln Gly Ile Arg Asn Asp Leu Gly Trp Tyr
145                 150                 155                 160

Gln Gln Lys Pro Gly Lys Ala Pro Glu Leu Leu Ile Tyr Gly Ala Ser
                165                 170                 175

Ser Leu Gln Ser Gly Val Pro Ser Arg Phe Ser Gly Ser Gly Ser Gly
            180                 185                 190

Thr Asp Phe Thr Leu Thr Ile Ser Ser Leu Gln Pro Glu Asp Ser Ala
        195                 200                 205

Thr Tyr Tyr Cys Leu Gln Asp Tyr Asn Gly Trp Thr Phe Gly Gln Gly
    210                 215                 220

Thr Lys Leu Glu Ile Lys Arg Ala Ala Ala Glu Gln Lys Leu Ile Ser
225                 230                 235                 240

Glu Glu Asp Leu Asn Gly Ala Ala His His His His His His
                245                 250

<210> SEQ ID NO 30
<211> LENGTH: 44
<212> TYPE: PRT
<213> ORGANISM: Homo sapiens

<400> SEQUENCE: 30

Ser Thr Ile Asp Asn Ala Trp Thr Val Gly Asp Ser Ala Asp Leu Arg
1               5                   10                  15

Val Cys Thr Asn Ser Thr Asn Cys Thr Glu Ile Asn Glu Leu Thr Gly
            20                  25                  30

Pro Glu Ala Phe Glu Gly Tyr Ser Val Met Gln Ala
        35                  40

<210> SEQ ID NO 31
<211> LENGTH: 30
<212> TYPE: DNA
<213> ORGANISM: Homo sapiens

<400> SEQUENCE: 31
cgcggatcct ctaccattga caatgcctgg                                      30

<210> SEQ ID NO 32
<211> LENGTH: 33
<212> TYPE: DNA
<213> ORGANISM: Homo sapiens

<400> SEQUENCE: 32
ccggaattct tacgcctgca tcacagaata acc                                  33
```